(12) United States Patent
Masakari et al.

(10) Patent No.: US 11,499,143 B2
(45) Date of Patent: Nov. 15, 2022

(54) AMADORIASE HAVING ENHANCED DEHYDROGENASE ACTIVITY

(71) Applicant: Kikkoman Corporation, Noda (JP)

(72) Inventors: Yosuke Masakari, Noda (JP); Airi Komatsuzaki, Noda (JP); Atsushi Ichiyanagi, Noda (JP)

(73) Assignee: Kikkoman Corporation, Chiba (JP)

( * ) Notice: Subject to any disclaimer, the term of this patent is extended or adjusted under 35 U.S.C. 154(b) by 149 days.

(21) Appl. No.: 15/521,104

(22) PCT Filed: Oct. 23, 2015

(86) PCT No.: PCT/JP2015/080014
§ 371 (c)(1),
(2) Date: Apr. 21, 2017

(87) PCT Pub. No.: WO2016/063984
PCT Pub. Date: Apr. 28, 2016

(65) Prior Publication Data
US 2017/0355967 A1 Dec. 14, 2017

(30) Foreign Application Priority Data
Oct. 24, 2014 (JP) .............................. JP2014-217405

(51) Int. Cl.
| | | |
|---|---|---|
| *C12N 9/06* | (2006.01) | |
| *C12Q 1/26* | (2006.01) | |
| *C12Q 1/00* | (2006.01) | |
| *G01N 27/416* | (2006.01) | |
| *C12M 1/40* | (2006.01) | |
| *G01N 27/327* | (2006.01) | |

(52) U.S. Cl.
CPC ............ *C12N 9/0032* (2013.01); *C12M 1/40* (2013.01); *C12Q 1/004* (2013.01); *C12Q 1/005* (2013.01); *C12Q 1/26* (2013.01); *C12Y 105/03* (2013.01); *G01N 27/327* (2013.01); *G01N 27/3272* (2013.01); *G01N 27/3275* (2013.01); *G01N 27/416* (2013.01); *G01N 2333/805* (2013.01); *G01N 2333/90672* (2013.01)

(58) Field of Classification Search
CPC ............ C12N 9/0032; G01N 27/3275; G01N 27/3272; G01N 2333/90672; G01N 2333/805; G01N 27/416; G01N 27/327; C12Y 105/03; C12Q 1/005; C12Q 1/004; C12Q 1/26; C12M 1/40
See application file for complete search history.

(56) References Cited

U.S. PATENT DOCUMENTS

| | | | |
|---|---|---|---|
| 5,370,990 A | 12/1994 | Staniford et al. | |
| 7,070,948 B1 | 7/2006 | Sakaue et al. | |
| 8,497,083 B2 * | 7/2013 | Ikebukuro ............ | C12N 9/0022 435/25 |
| 2008/0113381 A1 | 5/2008 | Matsuoka et al. | |
| 2008/0233605 A1 | 9/2008 | Taniguchi et al. | |
| 2009/0239239 A1 | 9/2009 | Hirokawa et al. | |
| 2011/0003361 A1 | 1/2011 | Kurosawa et al. | |
| 2011/0195444 A1 | 8/2011 | Hirao et al. | |
| 2012/0003678 A1* | 1/2012 | Aisaka ................. | C07K 14/805 435/23 |
| 2013/0267007 A1* | 10/2013 | Ichiyanagi ........... | G01N 33/723 435/191 |
| 2014/0234886 A1 | 8/2014 | Aisaka et al. | |
| 2014/0356928 A1 | 12/2014 | Masakari et al. | |
| 2016/0138073 A1 | 5/2016 | Ogawa et al. | |

FOREIGN PATENT DOCUMENTS

| | | |
|---|---|---|
| JP | 05-033997 B2 | 5/1993 |
| JP | 11-127895 A | 5/1999 |
| JP | 2001-095598 A | 4/2001 |
| JP | 2003-235585 A | 8/2003 |
| JP | 2004-275013 A | 10/2004 |
| JP | 2004-275063 A | 10/2004 |
| JP | 2010-035469 A | 2/2010 |
| JP | 2010-057474 A | 3/2010 |
| JP | 2011-229526 A | 11/2011 |
| JP | 2013-500729 A | 1/2013 |
| WO | WO 97/13872 A1 | 4/1997 |
| WO | WO 2004/104203 A1 | 12/2004 |
| WO | WO 2005/049857 A1 | 6/2005 |

(Continued)

OTHER PUBLICATIONS

Witkowski et al., Biochemistry 38:11643-11650, 1999.*

(Continued)

*Primary Examiner* — Delia M Ramirez

(74) *Attorney, Agent, or Firm* — Foley & Lardner LLP

(57) ABSTRACT

Provided are an amadoriase that is less likely to be influenced by oxygen concentration and a method and a reagent kit for measurement of HbA1c using such amadoriase. Provided are an amadoriase that is obtained via substitution of one or more amino acid residues at a position or positions corresponding to the position(s) selected from the group consisting of positions 280, 267, 269, 54, and 241 of the amadoriase derived from the genus *Coniochaeta*, a method for measurement of HbA1c, a reagent kit for measurement, and a sensor using such amadoriase. The modified amadoriase according to the invention has a lowered oxidase activity and an enhanced dehydrogenase activity, and this enables the use of an electron mediator, and this reduces the influence of oxygen concentration. Thus, HbA1c can be measured with high sensitivity.

14 Claims, 10 Drawing Sheets

Specification includes a Sequence Listing.

(56) References Cited

FOREIGN PATENT DOCUMENTS

| WO | WO 2007/125779 A1 | | 11/2007 |
|---|---|---|---|
| WO | WO 2010/041419 A1 | | 4/2010 |
| WO | WO 2010/041715 A1 | | 4/2010 |
| WO | WO 2011/015325 A1 | | 2/2011 |
| WO | WO 2011/015326 A2 | | 2/2011 |
| WO | WO 2012/018094 | * | 2/2012 |
| WO | WO 2013/100006 A1 | | 7/2013 |
| WO | WO 2015/005258 A1 | | 1/2015 |

OTHER PUBLICATIONS

Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Guo et al., PNAS 101(25):9205-9210, 2004.*
International Search Report dated Dec. 10, 2015 in PCT/JP2015/080014.
Ferri et al., "Cloning and Expression of Fructosyl-amine oxidase from Marine Yeast *Pichia* Species N1-1," Mar. Biotechnol., 2004, 6:625-632.
Ferri et al., "Isolation and characterization of a fructosyl-amine oxidase from an *Arthrobacter* sp.," Biotechnology Letters, 2005, 27:27-32.
Fujiwara et al., "Alteration of Substrate Specificity of Fructosyl-Amino Acid Oxidase from *Ulocladium* sp. JS-103," Journal of Bioscience and Bioengineering, 2006, 102(3):241-243.
Fujiwara et al., "Alteration of substrate specificity of fructosyl-amino acid oxidase from *Fusarium oxysporum*," Appl. Microbiol. Biotechnol., 2007, 74:813-819.
Gan et al., "Structural basis of the substrate specificity of the FPOD/FAOD family revealed by fructosyl peptide oxidase from *Eupenicillium terrenum*," Acta Crystallog. F Struc. Biol. Commun., 2015, 71:381-387.
GenPept Accession ID Q4WIF5, 2005, 2 pages.
Gomi et al., "Development of novel fructosyl peptide oxidases and their applications for the clinical diagnosis for diabetes," Journal of the Society for Bioscience and Bioengineering, Japan, 2014, 92(2):62-68, with partial English translation.
Hirokawa et al., "Molecular cloning and expression of novel fructosyl peptide oxidases and their application for the measurement of glycated protein," Biochemical and Biophysical Research Communications, 2003, 311:104-111.
Hirokawa et al., "Recombinant *Agrobacterium* AgaE-like Protein with Fructosyl Amino Acid Oxidase Activity," Biosci. Biotechnol. Biochem., 2002, 66(11):2323-2329.
Jeong et al., "The veA gene is necessary for the inducible expression by fructosyl amines of the *Aspergillus nidulans* faoA gene encoding fructosyl amino acid oxidase (amadoriase, EC 1.5.3)," Arch. Microbiol., 2002, 178:344-350.
Kim et al., "Construction of engineered fructosyl peptidyl oxidase for enzyme sensor applications under normal atmospheric conditions," Biotechnol. Lett., 2012, 34:491-497.
Kim et al., "Motif-Based Search for a Novel Fructosyl Peptide Oxidase from Genome Databases," Biotechnology and Bioengineering, Jun. 15, 2010, 106(3):358-366.
Kojima et al., "Mutational analysis of the oxygen-binding site of cholesterol oxidase and its impact on dye-mediated dehydrogenase activity," Journal of Molecular Catalysis B: Enzymatic, 2013, 88:41-46.
Masakari et al., "Development of thermostable fructosyl peptide oxidase," Proceedings of the Annual Meeting of Japan Society for Bioscience, Biotechnology and Agrochemistry (online), 2D01A04, 2014, 2 pages, with partial English translation.
Nierman et al., "Genomic sequence of the pathogenic and allergenic filamentous fungus *Aspergillus fumigatus*," Nature, 2005, 438:1151-1156.
Sakai et al., "Purification and Properties of Fructosyl Lysine Oxidase from *Fusarium oxysporum* S-1F4," Biosci. Biotech. Biochem., 1995, 59(3):487-491.
Sakaue et al., "Cloning and Expression of Fructosyl-amino Acid Oxidase Gene from *Corynebacterium* sp. 2-4-1 in *Escherichia coli*," Biosci. Biotechnol. Biochem., 2002, 66(6):1256-1261.
Yoshida et al., "Primary structures of fungal fructosyl amino acid oxidases and their application to the measurement of glycated proteins," Eur. J. Biochem., 1996, 242:499-505.
Office Action dated Sep. 17, 2019, in JP 2016-555413.
Ferri et al., "Tuning Fructosyl Peptidyl Oxidase into Dehydrogenase and Its Application for the Construction of an Enzyme Electrode," ECS Transactions, 2011, 35(7):113-116.
Ferri et al., "Biomolecular Engineering of Biosensing Molecules—The Challenges in Creating Sensing Molecules for Glycated Protein Biosensing," Electrochemistry, May 5, 2012, 80:293-298.
Kim et al., "Engineering of dye-mediated dehydrogenase property of fructosyl amino acid oxidases by site-directed mutagenesis studies of its putative proton relay system," Biotechnol. Lett., Apr. 11, 2010 (online), 32:1123-1129.

* cited by examiner

| | | | | | | | | | | | |
|---|---|---|---|---|---|---|---|---|---|---|---|
| Co | 399 | EEMAYQ | WRWRPG | -GDAL | KSRRAA | PPKDLA | DMPGWK | HDPKL- | ----- | ----- | 437 |
| Et | 399 | QEMAGA | WRVRPG | -GDAL | RSRRGA | PAKDLA | EMPGWK | HDAHL- | ----- | ----- | 437 |
| Py | 397 | ADLAHA | WRWRPG | -GDAL | QSRRAA | PAKDLA | DMPGWN | HD-ESP | RAKL-- | ----- | 440 |
| Ar | 400 | DDLAQA | WRWRPG | QGDAL | KSRRAA | PAKDLA | DMPGWN | HDGDSG | NATSGT | SSE-- | 449 |
| Cc | 397 | EDLAHA | WRVRPG | TGDAL | KSRRAA | PAKDLA | DMPGWK | HD-DVV | KSKL-- | ----- | 440 |
| Nv | 399 | DDLAEA | WRWRPG | QGDAL | KSRRAS | PAKDLA | DLPGWN | HDQDSE | SR---- | ----- | 441 |
| Cn | 399 | EDLAHA | WRWRPG | SGDAL | ARKSRR | ARDLAA | DMPGWN | HDEPSD | DDMDVK | DVA-- | 448 |
| Pn | 395 | DDLAHA | WRWRPG | SGDPL | -LLLLL | PAKDLA | DMPGWN | HD-KPR | ANL--- | ----- | 437 |
| An | 399 | SVFKDA | WRWRPG | TGDAL | KSRRRA | PAKDLA | DMPGWR | NEAKM- | ----- | ----- | 438 |
| En | 399 | SVFKDA | WRWRPG | TGDAL | KSRRRA | PAKDLA | DMPGWR | NEAKM- | ----- | ----- | 438 |
| Ul | 397 | DDLAHA | WRWRPG | TGDAL | KSRRRA | PARDLA | DMPGWN | HDGEAP | RAKL-- | ----- | 441 |
| Pj | 399 | QDLAGA | WRWRPG | -GDAL | KSKRSA | PAKDLA | EMPGWK | HDAKL- | ----- | ----- | 437 |

| | | | | |
|---|---|---|---|---|
| Co | 437 | ------ | ------ | 437 (SEQ ID NO: 1) |
| Et | 437 | ------ | ------ | 437 (SEQ ID NO: 3) |
| Py | 440 | ------ | ------ | 440 (SEQ ID NO: 4) |
| Ar | 450 | HKL--- | ------ | 452 (SEQ ID NO: 5) |
| Cc | 440 | ------ | ------ | 440 (SEQ ID NO: 6) |
| Nv | 441 | ------ | ------ | 441 (SEQ ID NO: 7) |
| Cn | 449 | VSLASVKIGENIGEKVVEDGARVGVKVLA | | 477 (SEQ ID NO: 8) |
| Pn | 437 | ------ | ------ | 437 (SEQ ID NO: 9) |
| An | 438 | ------ | ------ | 438 (SEQ ID NO: 10) |
| En | 438 | ------ | ------ | 438 (SEQ ID NO: 11) |
| Ul | 441 | ------ | ------ | 441 (SEQ ID NO: 12) |
| Pj | 437 | ------ | ------ | 437 (SEQ ID NO: 13) |

AMADORIASE HAVING ENHANCED DEHYDROGENASE ACTIVITY

CROSS-REFERENCE TO RELATED APPLICATIONS

This application is a National Stage application of PCT/JP2015/080014, filed Oct. 23, 2015, which claims priority from Japanese application JP 2014-217405, filed Oct. 24, 2014.

SEQUENCE LISTING

The instant application contains a Sequence Listing which has been submitted electronically in ASCII format and is hereby incorporated by reference in its entirety. Said ASCII copy, created on Dec. 17, 2020, is named PH-6321-PCT SL.txt and is 81,920 bytes in size.

TECHNICAL FIELD

The present invention relates to an amadoriase having an enhanced dehydrogenase activity, an amadoriase having a lowered oxidase activity, an amadoriase having an enhanced dehydrogenase activity and a lowered oxidase activity, genes and recombinant DNAs thereof, and a method for producing such amadoriases. The present invention also relates to an amadoriase that can be effectively used as a diagnostic enzyme or a sensor for diabetes or an amadoriase that can be effectively used for a kit for measuring a diabetes marker.

BACKGROUND ART

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement. Examples of amino groups in proteins include α-amino groups of the amino terminus and side chain ε-amino groups of the lysine residue in proteins. Examples of known glycated proteins generated in vivo include glycated hemoglobin resulting from glycation of hemoglobin and glycated albumin resulting from glycation of albumin in the blood.

Among such glycated proteins generated in vivo, glycated hemoglobin (HbA1c) has drawn attention as a glycemic control marker significant for diagnosis of diabetic patients and control of conditions in the field of clinical diagnosis of diabetes mellitus. The blood HbA1c level reflects the average blood glucose level for a given period of time in the past, and the measured value thereof serves as a significant indicator for diagnosis and control of diabetes conditions.

As a method for rapidly and readily measuring HbA1c, an enzymatic method using an amadoriase has been proposed, in which HbA1c is decomposed with e.g., a protease, and α-fructosyl valyl histidine (hereinafter referred to as "αFVH") or α-fructosyl valine (hereinafter referred to as "αFV") released from a β chain amino terminus thereof is quantified (see, for example, Patent Literatures 1 to 7). In reality, the method of cleaving αFV from HbA1c is associated with the problem in that accurate measurement values may not be obtained since the effect of contaminants and the like is significant. To obtain more accurate measurement values, methods of measuring αFVH are mainly employed in particular at present.

An amadoriase catalyzes a reaction of oxidizing iminodiacetic acid or a derivative thereof (also referred to as an "Amadori compound") in the presence of oxygen to produce glyoxylic acid or α-ketoaldehyde, an amino acid or a peptide, and hydrogen peroxide.

Amadoriases have been found in bacteria, yeast, and fungi. For example, amadoriases having enzymatic activity on αFVH and/or αFV, which is particularly useful for measurement of HbA1c, and derived from the genera *Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium*, and *Arthrobacter* have been reported (e.g., Patent Documents 1 and 6 to 15 and Non-Patent Documents 1 to 11). In some of these documents, an amadoriase may also be referred to as, for example, ketoamine oxidase, fructosyl amino acid oxidase, fructosyl peptide oxidase, or fructosyl amine oxidase.

An amadoriase may be used in conjunction with a peroxidase and, by utilizing a colorimetric substrate, may be used for the assay of a glycated substrate in a sample. A conventional amadoriase is capable of transmitting electrons to oxygen molecules when oxidizing a glycated substrate. Such activity is referred to as an "oxidase activity." By lowering the oxidase activity of an enzyme and enhancing the dehydrogenase activity thereof, electron acceptors (i.e., electron mediators) can be used instead of oxygen molecules. Thus, an assay can be carried out without being affected by oxygen.

There is disclosure of enhanced dehydrogenase activity of an amadoriase in the literature. For example, substitution of asparagine at position 56 of fructosyl amino acid oxidase derived from *Phaeosphaeria nodorum* leads to an enhanced dehydrogenase activity ($V_{max}/K_m$ relative to αFV) by 2.3 times (Patent Document 16). However, the variant disclosed therein also has an enhanced oxidase activity ($V_{max}/K_m$ relative to αFV) by 1.2 times compared with the wild-type. Accordingly, it is believed that such variant remains susceptible to oxygen.

PRIOR ART DOCUMENTS

Patent Documents

Patent Document 1: WO 2004/104203
Patent Document 2: WO 2005/49857
Patent Document 3: JP 2001-95598 A
Patent Document 4: JP H05-33997 B (1993)
Patent Document 5: JP H11-127895 A (1999)
Patent Document 6: WO 97/13872
Patent Document 7: JP 2011-229526 A
Patent Document 8: JP 2003-235585 A
Patent Document 9: JP 2004-275013 A
Patent Document 10: JP 2004-275063 A
Patent Document 11: JP 2010-35469 A
Patent Document 12: JP 2010-57474 A
Patent Document 13: WO 2010/41715
Patent Document 14: WO 2010/41419
Patent Document 15: WO 2011/15325
Patent Document 16: JP 2013-500729 A Non-Patent Documents Non-Patent Document 1: Biochem. Biophys. Res. Commun., 311, 104-11, 2003
Non-Patent Document 2: Biotechnol. Bioeng., 106, 358-66, 2010

Non-Patent Document 3: J. Biosci. Bioeng., 102, 241-3, 2006
Non-Patent Document 4: Eur. J. Biochem., 242, 499-505, 1996
Non-Patent Document 5: Arch. Microbiol., 178, 344-50, 2002
Non-Patent Document 6: Mar. Biotechnol., 6, 625-32, 2004
Non-Patent Document 7: Biosci. Biotechnol. Biochem., 59, 487-91, 1995
Non-Patent Document 8: Appl. Microbiol. Biotechnol., 74, 813-819, 2007
Non-Patent Document 9: Biosci. Biotechnol. Biochem., 66, 1256-61, 2002
Non-Patent Document 10: Biosci. Biotechnol. Biochem., 66, 2323-29, 2002
Non-Patent Document 11: Biotechnol. Letters 27, 27-32, 2005

SUMMARY OF THE INVENTION

Objects to be Attained by the Invention

It is an object of the present invention to provide an amadoriase having lowered oxidase activity and enhanced dehydrogenase activity. It is also an object of the present invention to provide an amadoriase wherein the activity thereof is not substantially influenced by dissolved oxygen levels.

Means for Attaining the Objects

At present, substantially no information is available concerning lowering of the oxidase activity of an enzyme and enhancement of the dehydrogenase activity. Under such circumstances, the present inventors have conducted concentrate studies and as a result, discovered that the above objects can be attained by introducing substitution of a particular amino acid residue into an amadoriase derived from the genus *Coniochaeta*. This has led to the completion of the present invention.

The present invention encompasses the following.

[1] A modified amadoriase exhibiting a lower ratio of oxidase activity to dehydrogenase activity (OX/DH) compared to an amadoriase before modification selected from the group consisting of the following:

(i) an amadoriase comprising an amino acid sequence comprising, when aligned with the amino acid sequence as shown in SEQ ID NO: 1, substitution of one or more amino acids at positions corresponding to positions selected from the group consisting of positions 280, 267, 269, 54, and 241 of the amino acid sequence as shown in SEQ ID NO: 1 and having dehydrogenase activity;

(ii) the amadoriase as defined in (i) comprising an amino acid sequence resulting from substitution, deletion, or addition of one or several amino acids at positions other than those corresponding to positions 280, 267, 269, 54, and 241 of the amino acid sequence as shown in SEQ ID NO: 1 and having dehydrogenase activity;

(iii) the amadoriase as defined in (i) comprising an amino acid sequence having 70% or higher sequence identity with the amino acid sequence as shown in SEQ ID NO: 1, SEQ ID NO: 3, SEQ ID NO: 6, SEQ ID NO: 9, SEQ ID NO: 10, SEQ ID NO: 11, SEQ ID NO: 44, SEQ ID NO: 53, or SEQ ID NO: 67 over the full length and 90% or higher sequence identity between the amino acid sequence of a homologous region consisting of amino acids at positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of the amino acid sequence as shown in SEQ ID NO: 1 and the amino acid sequence of the homologous region of corresponding positions of the amadoriase and having dehydrogenase activity; or (iv) the amadoriase as defined in (i) comprising an amino acid sequence exhibiting 80% or higher sequence identity with the amino acid sequence as shown in SEQ ID NO: 1, SEQ ID NO: 3, SEQ ID NO: 6, SEQ ID NO: 9, SEQ ID NO: 10, SEQ ID NO: 11, SEQ ID NO: 44, SEQ ID NO: 53, or SEQ ID NO: 67 over the full length and having dehydrogenase activity.

[2] The amadoriase according to [1], wherein the amino acid at the position corresponding to position 280 of the amino acid sequence as shown in SEQ ID NO: 1 has been substituted with a polar amino acid selected from the group consisting of glutamine, serine, threonine, and asparagine, a charged amino acid selected from the group consisting of aspartic acid, glutamic acid, lysine, arginine, and histidine, or an amino acid selected from the group consisting of methionine, proline, phenylalanine, tyrosine, and tryptophane;

the amino acid at the position corresponding to position 267 of the amino acid sequence as shown in SEQ ID NO: 1 has been substituted with methionine, leucine, tyrosine, isoleucine, tryptophane, valine, or alanine;

the amino acid at the position corresponding to position 269 of the amino acid sequence as shown in SEQ ID NO: 1 has been substituted with methionine, leucine, tyrosine, isoleucine, tryptophane, valine, or alanine;

the amino acid at the position corresponding to position 54 of the amino acid sequence as shown in SEQ ID NO: 1 has been substituted with an amino acid selected from the group consisting of asparagine, alanine, glutamine, histidine, glycine, or valine; or the amino acid at the position corresponding to position 241 of the amino acid sequence as shown in SEQ ID NO: 1 has been substituted with an amino acid selected from the group consisting of glutamine, lysine, glutamic acid, asparagine, arginine, aspartic acid, and histidine.

[3] The amadoriase according to [2], wherein the amino acid at the position corresponding to position 280 of the amino acid sequence as shown in SEQ ID NO: 1 has been substituted with glutamine, serine, histidine, threonine, asparagine, aspartic acid, glutamic acid, lysine, arginine, or methionine;

the amino acid at the position corresponding to position 267 of the amino acid sequence as shown in SEQ ID NO: 1 has been substituted with methionine, leucine, tyrosine, isoleucine, or tryptophane;

the amino acid at the position corresponding to position 269 of the amino acid sequence as shown in SEQ ID NO: 1 has been substituted with methionine, leucine, tyrosine, isoleucine, or tryptophane;

the amino acid at the position corresponding to position 54 of the amino acid sequence as shown in SEQ ID NO: 1 has been substituted with asparagine or alanine; or the amino acid at the position corresponding to position 241 of the amino acid sequence as shown in SEQ ID NO: 1 has been substituted with glutamine, glutamic acid, or lysine.

[4] The amadoriase according to [3], wherein the amino acid at the position corresponding to position 280 of the amino acid sequence as shown in SEQ ID NO: 1 has been substituted with glutamine, serine, histidine, threonine, asparagine, aspartic acid, glutamic acid, lysine, arginine, or methionine;

the amino acid at the position corresponding to position 267 of the amino acid sequence as shown in SEQ ID NO: 1 has been substituted with methionine, leucine, or tyrosine;

the amino acid at the position corresponding to position 269 of the amino acid sequence as shown in SEQ ID NO: 1 has been substituted with methionine, leucine, or tyrosine;

the amino acid at the position corresponding to position 54 of the amino acid sequence as shown in SEQ ID NO: 1 has been substituted with asparagine or alanine; or the amino acid at the position corresponding to position 241 of the amino acid sequence as shown in SEQ ID NO: 1 has been substituted with glutamine, glutamic acid, or lysine.

[5] The amadoriase according to [3], wherein the amino acid at the position corresponding to position 280 of the amino acid sequence as shown in SEQ ID NO: 1 has been substituted with glutamine or serine;

the amino acid at the position corresponding to position 267 of the amino acid sequence as shown in SEQ ID NO: 1 has been substituted with methionine, leucine, or tyrosine;

the amino acid at the position corresponding to position 269 of the amino acid sequence as shown in SEQ ID NO: 1 has been substituted with methionine, leucine, or tyrosine; or the amino acid at the position corresponding to position 241 of the amino acid sequence as shown in SEQ ID NO: 1 has been substituted with glutamine.

[6] The amadoriase according to [3], wherein the amino acid at the position corresponding to position 280 of the amino acid sequence as shown in SEQ ID NO: 1 has been substituted with glutamine or histidine;

the amino acid at the position corresponding to position 267 of the amino acid sequence as shown in SEQ ID NO: 1 has been substituted with methionine or leucine; or the amino acid at the position corresponding to position 269 of the amino acid sequence as shown in SEQ ID NO: 1 has been substituted with methionine or leucine.

[7] The amadoriase according to [3], wherein the amino acid at the position corresponding to position 280 of the amino acid sequence as shown in SEQ ID NO: 1 has been substituted with glutamine;

the amino acid at the position corresponding to position 267 of the amino acid sequence as shown in SEQ ID NO: 1 has been substituted with methionine or leucine; or the amino acid at the position corresponding to position 269 of the amino acid sequence as shown in SEQ ID NO: 1 has been substituted with methionine or leucine.

[8] The amadoriase according to any of [1] to [7], wherein the ratio of oxidase activity to dehydrogenase activity (OX/DH) is reduced to less than 80% that of the amadoriase before modification (100%).

[9] The amadoriase according to any of [1] to [8], which is derived from the genus *Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Debaryomyces, Corynebacterium, Agrobacterium,* or *Arthrobacter.*

[10] The amadoriase according to any of [1] to [9], which has the amino acid sequence as shown in SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 44, SEQ ID NO: 53, or SEQ ID NO: 67 and has the amino acid substitution as defined in any of [1] to [7].

[11] The amadoriase according to any of [1] to [10] comprising an amino acid sequence comprising, when aligned with the amino acid sequence as shown in SEQ ID NO: 1, substitution or deletion of one or more amino acids at positions corresponding to the positions of the amino acid sequence as shown in SEQ ID NO: 1 selected from the group consisting of the following positions and having dehydrogenase activity:

(A) positions 62, 63, 102, 106, 110, 113, 355, 419, 68, and 356;

(B) positions 262, 257, 249, 253, 337, 340, 232, 129, 132, 133, 44, 256, 231, and 81, and (C) deletion of 3 amino acid residues at positions 435, 436, and 437 at the carboxyl terminus.

[12] The amadoriase according to [11], which comprises an amino acid sequence comprising, when aligned with the amino acid sequence as shown in SEQ ID NO: 1, substitution or deletion of one or more amino acids at positions corresponding to the positions of the amino acid sequence as shown in SEQ ID NO: 1 selected from the group consisting of the substitutions shown below and has a dehydrogenase activity:

(A) substitution of the amino acid at the position corresponding to arginine at position 62 with alanine, asparagine, or aspartic acid;

substitution of the amino acid at the position corresponding to leucine at position 63 with histidine or alanine;

substitution of the amino acid at the position corresponding to glutamic acid at position 102 with lysine;

substitution of the amino acid at the position corresponding to aspartic acid at position 106 with alanine, lysine, or arginine;

substitution of the amino acid at the position corresponding to glutamine at position 110 with leucine or tyrosine;

substitution of the amino acid at the position corresponding to alanine at position 113 with lysine or arginine;

substitution of the amino acid at the position corresponding to alanine at position 355 with serine;

substitution of the amino acid at the position corresponding to alanine at position 419 with lysine;

substitution of the amino acid at the position corresponding to aspartic acid at position 68 with asparagine; or substitution of the amino acid at the position corresponding to alanine at position 356 with threonine;

(B) substitution of the amino acid at the position corresponding to asparagine at position 262 with histidine;

substitution of the amino acid at the position corresponding to valine at position 257 with cysteine, serine, or threonine;

substitution of the amino acid at the position corresponding to glutamic acid at position 249 with lysine or arginine;

substitution of the amino acid at the position corresponding to glutamic acid at position 253 with lysine or arginine;

substitution of the amino acid at the position corresponding to glutamine at position 337 with lysine or arginine;

substitution of the amino acid at the position corresponding to glutamic acid at position 340 with proline;

substitution of the amino acid at the position corresponding to aspartic acid at position 232 with lysine or arginine;

substitution of the amino acid at the position corresponding to aspartic acid at position 129 with lysine or arginine;

substitution of the amino acid at the position corresponding to aspartic acid at position 132 with lysine or arginine;

substitution of the amino acid at the position corresponding to glutamic acid at position 133 with alanine, methionine, lysine, or arginine;

substitution of the amino acid at the position corresponding to glutamic acid at position 44 with proline;

substitution of the amino acid at the position corresponding to glycine at position 256 with lysine or arginine;

substitution of the amino acid at the position corresponding to glutamic acid at position 231 with lysine or arginine;

substitution of the amino acid at the position corresponding to glutamic acid at position 81 with lysine or arginine; and (C) deletion of 3 amino acids at the carboxyl terminus at positions corresponding to proline at position 435, lysine at position 436, and leucine at position 437.

[13] A reagent kit for measurement of HbA1c comprising the amadoriase according to any of [1] to [12].

[14] An enzyme electrode comprising the amadoriase according to any of [1] to [12].

[15] An enzyme sensor comprising the enzyme electrode according to [14] as a working electrode.

[16] A method for measurement of HbA1c involving the use of the amadoriase according to any of [1] to [12], the enzyme electrode according to [14], or the enzyme sensor according to [15] and an electron mediator.

This description includes part or all of the content as disclosed in the description and/or drawings of Japanese Patent Application No. 2014-217405, which is a priority document of the present application.

Effects of the Invention

The present invention can provide an amadoriase with excellent properties that is less susceptible to oxygen and can be used as a diagnostic enzyme for diabetes capable of measurement with high sensitivity and for a sensor for measurement of a diabetes marker and a gene encoding such enzyme. With the use of such amadoriase, glycated hemoglobin can be measured with higher accuracy even in the presence of oxygen.

BRIEF DESCRIPTION OF THE DRAWINGS

FIG. 1-1 shows examples of identical and similar amino acids in amino acid sequences of various known amadoriases. In addition to Co, Et, Py, Ar, Cc, and Nv, Cn, Pn, An, En, Ul, and Pj are aligned.

FIG. 1-2 is a continuation of FIG. 1-1.

FIG. 1-3 is a continuation of FIG. 1-2.

FIG. 1-4 is a continuation of FIG. 1-3.

FIG. 1-5 is a continuation of FIG. 1-4.

FIG. 2 shows oxidase activity and dehydrogenase activity of an amadoriase. FIG. 2 schematically illustrates an enzyme reaction, and properties, such as substrate specificity of the enzyme, are not limited.

FIG. 3-1 shows the results of electrochemical measurement of αFVH using the CFP-T7 amadoriase.

FIG. 3-2 is a continuation of FIG. 3-1.

FIG. 4-1 shows the results of electrochemical measurement of αFVH using the CFP-T7-280Q amadoriase.

FIG. 4-2 is a continuation of FIG. 4-1.

EMBODIMENTS FOR CARRYING OUT THE INVENTION

Figure 2:
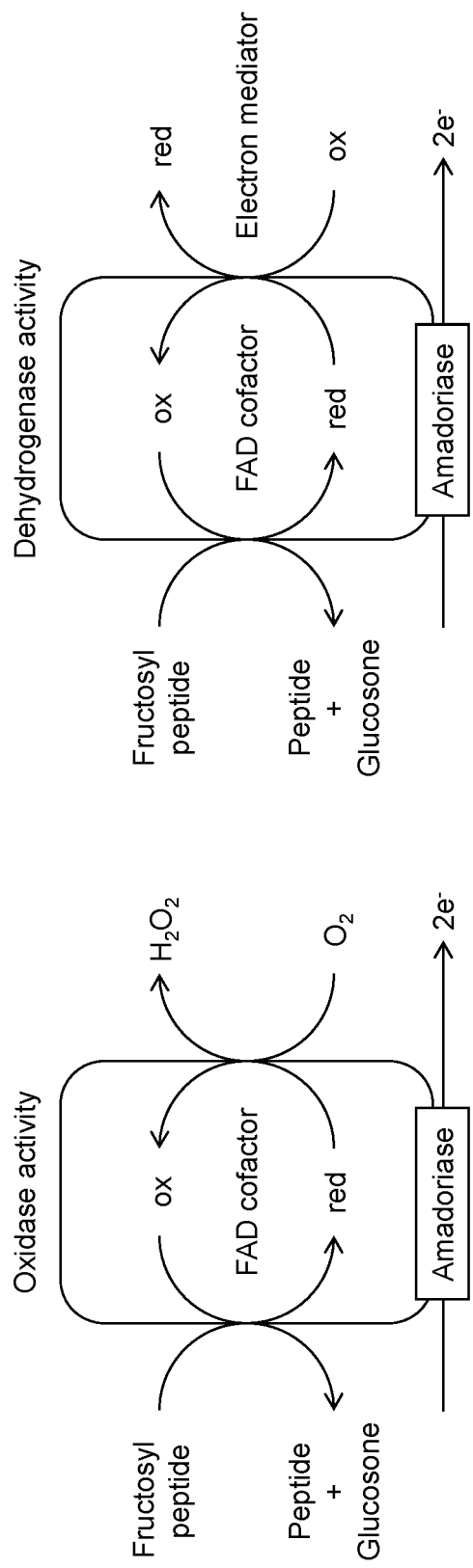

Hereafter, the present invention is described in detail.

The amadoriase according to the present invention can recognize a glycated protein or a glycated peptide as a substrate.

(Glycated Protein and Hemoglobin A1c)

The term "glycated protein" used herein refers to a protein glycated non-enzymatically. Glycated proteins exist in vivo and ex vivo. Examples of glycated proteins existing in vivo include glycated hemoglobin and glycated albumin in the blood. In particular, glycated hemoglobin comprising glycated valine at the β-chain amino terminus of hemoglobin is referred to as hemoglobin A1c (HbA1c). Examples of glycated proteins existing ex vivo include foods and drinks, such as liquid flavors, and infusion solutions in which a protein or peptide exists together with sugar.

(Glycated Peptide and Fructosyl Peptide)

The term "glycated peptide" used herein refers to a non-enzymatically-glycated peptide derived from a glycated protein. Peptides that are directly and non-enzymatically glycated, products of degradation of glycated proteins by a protease or the like, and products of glycation of (poly) peptides constituting glycated proteins are included in glycated peptides. A "glycated peptide" is also referred to as a "fructosyl peptide." Regarding glycated proteins, examples of amino groups in the glycated peptide side chain include an amino terminal α-amino group and a ε-amino group in the lysine side chain within a peptide. However, in the present invention, the glycated peptide is, more specifically, an α-glycated peptide (α-fructosyl peptide). An α-glycated peptide is released and formed from a glycated protein having a glycated N-terminal α-amino acid by an arbitrary means, such as limited degradation with a protease or the like. Where the glycated protein of interest is hemoglobin A1c (HbA1c), for example, the α-glycated peptide is a glycated peptide cleaved from the HbA1c β-chain having the glycated N terminus. The HbA1c β-chain composed of 146 amino acids also falls under an α-glycated peptide (αF146P).

According to an embodiment of the present invention, the target substance (i.e., the substrate) to which the amadoriase of the present invention acts on is HbA1c and more specifically is the β-chain of HbA1c. According to another embodiment, the target substance to which the amadoriase of the present invention acts on is α-glycated peptide cleaved from the β-chain of HbA1c, such as αFV to αF128P, αFV to αF64P, αFV to αF32P, or αFV to αF16P. More specifically, it is α-fructosyl-valyl-histidyl-leucyl-threonyl-prolyl-glutamic acid (αF6P). According to another embodiment, the target substance to which the amadoriase of the present invention acts on is αFVH (α-fructosyl-valyl-histidine) or αFV (α-fructosyl valine).

(Amadoriase)

An amadoriase is also referred to as ketoamine oxidase, fructosyl amino acid oxidase, fructosyl peptide oxidase, or fructosyl amine oxidase. An amadoriase is an enzyme that catalyzes the reaction which oxidizes iminodiacetic acid or a derivative thereof (Amadori compound) in the presence of oxygen to generate glyoxylic acid or α-ketoaldehyde, amino acid or peptide, and hydrogen peroxide. Amadoriases are widely distributed in nature and can be obtained by searching for enzymes from sources of microorganisms, animals, or plants. With regard to microorganisms, amadoriases can be obtained from, for example, filamentous fungi, yeast, or bacteria.

The amadoriase according to an embodiment of the present invention is a variant of an amadoriase having an enhanced dehydrogenase activity, which is prepared based on an amadoriase derived from the genus *Coniochaeta* having the amino acid sequence as shown in SEQ ID NO: 1 or an amadoriase derived from *Curvularia clavata* having the amino acid sequence as shown in SEQ ID NO: 6.

The amadoriase according to an embodiment of the present invention is a variant of an amadoriase having an enhanced dehydrogenase activity, which is prepared based on an amadoriase derived from *Eupenicillium terrenum* having the amino acid sequence as shown in SEQ ID NO: 3 or SEQ ID NO: 44.

The amadoriase according to an embodiment of the present invention is a variant of an amadoriase having an enhanced dehydrogenase activity, which is prepared based on an amadoriase derived from *Phaeosphaeria nodorum* having the amino acid sequence as shown in SEQ ID NO: 9.

The amadoriase according to an embodiment of the present invention is a variant of an amadoriase having an enhanced dehydrogenase activity, which is prepared based on fructosyl amino acid oxidase derived from *Aspergillus nidulans* having the amino acid sequence as shown in SEQ ID NO: 10 or SEQ ID NO: 53.

The amadoriase according to an embodiment of the present invention is a variant of an amadoriase having an enhanced dehydrogenase activity, which is prepared based on fructosyl peptide oxidase derived from *Emericella nidulans* having the amino acid sequence as shown in SEQ ID NO: 11 or SEQ ID NO: 67.

Examples of such variants include an amadoriase comprising an amino acid sequence exhibiting a high degree of sequence identity with SEQ ID NO: 1, SEQ ID NO: 3, SEQ ID NO: 6, SEQ ID NO: 9, SEQ ID NO: 10, SEQ ID NO: 11, SEQ ID NO: 44, SEQ ID NO: 53, or SEQ ID NO: 67 (e.g., 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher) and an amadoriase comprising an amino acid sequence derived from the amino acid sequence as shown in SEQ ID NO: 1, SEQ ID NO: 3, SEQ ID NO: 6, SEQ ID NO: 9, SEQ ID NO: 10, SEQ ID NO: 11, SEQ ID NO: 44, SEQ ID NO: 53, or SEQ ID NO: 67 by modification, mutation, deletion, substitution, addition, and/or insertion of 1 to several amino acids.

The amadoriase according to the present invention may be prepared from an amadoriase derived from an organism species belonging to, for example, the genus *Eupenicillium*, *Pyrenochaeta*, *Arthrinium*, *Curvularia*, *Neocosmospora*, *Cryptococcus*, *Phaeosphaeria*, *Aspergillus*, *Emericella*, *Ulocladium*, *Penicillium*, *Fusarium*, *Achaetomiella*, *Achaetomium*, *Thielavia*, *Chaetomium*, *Gelasinospora*, *Microascus*, *Leptosphaeria*, *Ophiobolus*, *Pleospora*, *Coniochaetidium*, *Pichia*, *Corynebacterium*, *Agrobacterium*, or *Arthrobacter*. In particular, an amadoriase having dehydrogenase activity and/or comprising an amino acid sequence exhibiting a high degree of sequence identity with the sequence as shown in SEQ ID NO: 1 as described above is preferable.

A variant of an amadoriase having a lowered oxidase activity and an enhanced dehydrogenase activity (a modified amadoriase) can be obtained by substitution, addition, or deletion of at least 1 amino acid residue in the amino acid sequence of the amadoriase.

(Substitution for Enhancing Dehydrogenase Activity or Lowering Oxidase Activity)

Examples of amino acid substitutions for enhancing dehydrogenase activity and/or lowering oxidase activity include substitutions of amino acids at positions corresponding to the positions of the amino acid sequence as shown in SEQ ID NO: 1 described below:

(1) substitution of cysteine at position 280 with, for example, a polar amino acid selected from the group consisting of glutamine, serine, threonine, and asparagine, a charged amino acid selected from the group consisting of aspartic acid, glutamic acid, lysine, arginine, and histidine, or an amino acid selected from the group consisting of methionine, proline, phenylalanine, tyrosine, and tryptophane;

(2) substitution of phenylalanine at position 267 with, for example, a hydrophobic amino acid residue selected from the group consisting of tyrosine, leucine, methionine, tryptophane, isoleucine, valine, or alanine;

(3) substitution of phenylalanine at position 269 with, for example, a hydrophobic amino acid residue selected from the group consisting of tyrosine, leucine, methionine, tryptophane, isoleucine, valine, and alanine;

(4) substitution of aspartic acid at position 54 with, for example, asparagine, alanine, glutamine, histidine, glycine, or valine; and (5) substitution of tyrosine at position 241 with, for example, glutamine, lysine, glutamic acid, asparagine, aspartic acid, arginine, or histidine.

For convenience of description, glutamine, serine, threonine, and asparagine may be referred to as "polar amino acids" herein. Further, aspartic acid, glutamic acid, lysine, arginine, and histidine may be referred to as "charged amino acids." Further, alanine, valine, isoleucine, leucine, methionine, phenylalanine, tyrosine, and tryptophane may be referred to as "hydrophobic amino acids." Furthermore, methionine, phenylalanine, tyrosine, tryptophane, and proline may be referred to as "bulky amino acids."

A variant of the amadoriase according to the present invention having an enhanced dehydrogenase activity and a lowered oxidase activity may comprise at least 1 or a plurality of the amino acid substitutions described above. For example, such variant comprises the amino acid substitution (1), (2), (3), (4), or (5) described above.

In particular, a variant comprising an amino acid substitution at a position corresponding to the amino acid position described below and having an enhanced dehydrogenase activity and a lowered oxidase activity is preferable:

(1) substitution of cysteine at position 280 with, for example, glutamine, serine, histidine, threonine, aspartic acid, glutamic acid, methionine, lysine, arginine, or asparagine;

(2) substitution of phenylalanine at position 267 with, for example, tyrosine, leucine, or methionine;

(3) substitution of phenylalanine at position 269 with, for example, tyrosine, leucine, or methionine;

(4) substitution of aspartic acid at position 54 with, for example, asparagine or alanine; or (5) substitution of tyrosine at position 241 with, for example, glutamine, lysine, or glutamic acid.

The amadoriase variant according to the present invention may comprise an amino acid substitution for enhancing dehydrogenase activity and/or lowering oxidase activity of the amino acid sequence as shown in SEQ ID NO: 1.

Further, the amadoriase variant according to the present invention may comprise deletion, insertion, addition, and/or substitution of one or several amino acids (e.g., 1 to 15, 1 to 10, preferably 1 to 5, further preferably 1 to 3, and particularly preferably 1 amino acid) at a position (or positions) other than the positions of the amino acid substitutions described above. Furthermore, the present invention encompasses an amadoriase variant comprising the amino acid substitution for enhancing dehydrogenase activity and/or lowering oxidase activity and an amino acid substitution for improving properties other than the dehydrogenase activity, such as substrate specificity, said variant having an amino acid sequence identity of 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher to a region of the amino acid sequence as shown in SEQ ID NO: 1 other than the amino acid substitution described above, having an amadoriase activity, and having a modified dehydrogenase activity.

An amadoriase having the amino acid sequence as shown in SEQ ID NO: 1 is an amadoriase (CFP-T7) derived from the genus *Coniochaeta* produced by *E. coli* carrying a recombinant plasmid referred to as "pKK223-3-CFP-T7" in WO 2007/125779 (Accession Number: FERM BP-10593), which is a modified amadoriase with excellent heat stability previously discovered by the present inventors. CFP-T7 is a triple variant obtained by successively introducing artificial mutations into positions 272, 302, and 388 of a naturally-occurring amadoriase derived from the genus *Coniochaeta*.

Concerning the amino acid substitutions described above, an amino acid position indicates a position in the amino acid sequence of an amadoriase derived from the genus *Coniochaeta* as shown in SEQ ID NO: 1. In the case of the amino acid sequence of an amadoriase derived from other organism species, an amino acid at a position corresponding to the position in the amino acid sequence as shown in SEQ ID NO: 1 is substituted. The meaning of the expression "a position corresponding to . . . " is described elsewhere.

(Additional Substitution)
(Amino Acid Substitution that Alters Substrate Specificity of Amadoriase)

Previously, the present inventors reported that substrate specificity of an amadoriase can be altered through substitution of amino acid residues thereof (see, for example, WO 2013/162035, incorporated herein by reference in its entirety). The amadoriase according to the present invention may optionally further comprise such amino acid substitution.

Examples of amino acid substitutions that alter substrate specificity of an amadoriase include substitutions of amino acids at positions corresponding to the amino acids at the positions of the amino acid sequence as shown in SEQ ID NO: 1 described below:
  (a) arginine at position 62;
  (b) leucine at position 63;
  (c) glutamic acid at position 102;
  (d) aspartic acid at position 106;
  (e) glutamine at position 110;
  (f) alanine at position 113;
  (g) alanine at position 355;
  (h) alanine at position 419;
  (i) aspartic acid at position 68; and
  (j) alanine at position 356.

Optionally, the amino acid at a position corresponding to arginine at position 62 may be substituted with alanine, asparagine, or aspartic acid.

Optionally, the amino acid at the position corresponding to (b) leucine at position 63 may be substituted with histidine or alanine.

Optionally, the amino acid at the position corresponding to (c) glutamic acid at position 102 may be substituted with lysine.

Optionally, the amino acid at the position corresponding to (d) aspartic acid at position 106 may be substituted with alanine, lysine, or arginine.

Optionally, the amino acid at the position corresponding to (e) glutamine at position 110 may be substituted with leucine or tyrosine.

Optionally, the amino acid at the position corresponding to (f) alanine at position 113 may be substituted with lysine or arginine.

Optionally, the amino acid at the position corresponding to (g) alanine at position 355 may be substituted with serine.

Optionally, the amino acid at the position corresponding to (h) alanine at position 419 may be substituted with lysine.

Optionally, the amino acid at the position corresponding to (i) aspartic acid at position 68 may be substituted with asparagine.

Optionally, the amino acid at the position corresponding to (j) alanine at position 356 may be substituted with threonine.

(Amino Acid Substitution that Enhances Surfactant Tolerance of Amadoriase)

The present inventors confirmed that surfactant tolerance of an amadoriase could be enhanced through substitution of amino acid residues thereof (see, for example, JP Patent Application No. 2013-221515 and PCT/JP2014/071036, incorporated herein by reference in their entirety).

Examples of amino acid substitutions that enhance surfactant tolerance of an amadoriase include substitutions of amino acids at positions corresponding to the amino acids at the positions of the amino acid sequence as shown in SEQ ID NO: 1 described below:
  (i) asparagine at position 262;
  (ii) valine at position 257;
  (iii) glutamic acid at position 249;
  (iv) glutamic acid at position 253;
  (v) glutamine at position 337;
  (vi) glutamic acid at position 340;
  (vii) aspartic acid at position 232;
  (viii) aspartic acid at position 129;
  (ix) aspartic acid at position 132;
  (x) glutamic acid at position 133;
  (xi) glutamic acid at position 44;
  (xii) glycine at position 256;
  (xiii) glutamic acid at position 231; and
  (xiv) glutamic acid at position 81.

Optionally, the amino acid at the position corresponding to asparagine at position 262 may be substituted with histidine.

Optionally, the amino acid at the position corresponding to valine at position 257 may be substituted with cysteine, serine, or threonine.

Optionally, the amino acid at the position corresponding to glutamic acid at position 249 may be substituted with lysine or arginine.

Optionally, the amino acid at the position corresponding to glutamic acid at position 253 may be substituted with lysine or arginine.

Optionally, the amino acid at the position corresponding to glutamine at position 337 may be substituted with lysine or arginine.

Optionally, the amino acid at the position corresponding to glutamic acid at position 340 may be substituted with proline.

Optionally, the amino acid at the position corresponding to aspartic acid at position 232 may be substituted with lysine or arginine.

Optionally, the amino acid at the position corresponding to aspartic acid at position 129 may be substituted with lysine or arginine.

Optionally, the amino acid at the position corresponding to aspartic acid at position 132 may be substituted with lysine or arginine.

Optionally, the amino acid at the position corresponding to glutamic acid at position 133 may be substituted with alanine, methionine, lysine, or arginine.

Optionally, the amino acid at the position corresponding to glutamic acid at position 44 may be substituted with proline.

Optionally, the amino acid at the position corresponding to glycine at position 256 may be substituted with lysine or arginine.

Optionally, the amino acid at the position corresponding to glutamic acid at position 231 may be substituted with lysine or arginine.

Optionally, the amino acid at the position corresponding to glutamic acid at position 81 may be substituted with lysine or arginine.

(Amino Acid Deletion Capable of Improving Heat Stability of the Amadoriase)

Previously, the present inventors reported that heat stability of an amadoriase can be improved by deletion of 3 amino acid residues from its carboxyl terminus (see WO 2013/100006, incorporated herein by reference in its entirety). In one embodiment, the amadoriase of the present invention may comprise a deletion of 3 amino acid residues from the carboxyl terminus thereof, in addition to the substitution described above. The term "deletion of 3 amino acid residues from the carboxyl terminus" used herein may be referred to as a deletion capable of improving heat stability.

(Obtaining a Gene Encoding an Amadoriase)

In order to obtain a gene encoding an amadoriase according to the present invention described above (hereinafter, also merely referred to as "amadoriase genes"), widely used gene cloning methods can be used. For example, chromosomal DNA or mRNA can be extracted from a microorganism fungus body or various cells having the ability to produce an amadoriase by conventional techniques, such as the method described in "Current Protocols in Molecular Biology" (WILEY Interscience, 1989). In addition, cDNA can be synthesized using mRNA as the template. A chromosomal DNA or cDNA library can be constructed using the chromosomal DNA or cDNA obtained in such a manner.

Subsequently, DNA including the entire sequence of a target amadoriase gene can be obtained by a method of synthesizing an appropriate probe DNA based on the amino acid sequence of the amadoriase mentioned above and selecting an amadoriase gene from a chromosomal DNA or cDNA library using the probe DNA. Alternatively, an appropriate primer DNA may be designed based on the amino acid sequence mentioned above, a DNA including the target gene fragment encoding the amadoriase gene may be amplified by using an appropriate polymerase chain reaction (PCR) technique, such as the 5' RACE or 3' RACE method, and the resulting DNA fragments may then be linked to obtain DNA comprising the entire length of the amadoriase gene of interest.

A preferable example of a gene encoding an amadoriase thus obtained includes an amadoriase gene derived from the genus *Coniochaeta* (JP 2003-235585 A).

The amadoriase genes are preferably linked to various vectors using conventional techniques from the perspective of handling. Examples include the recombinant plasmid pKK223-3-CFP (JP 2003-235585 A) prepared by inserting DNA encoding the amadoriase gene derived from the *Coniochaeta* sp. NISL 9330 strain into the pKK223-3 vector (GE Healthcare).

(Vector)

Vectors that can be used in the present invention are not limited to the plasmid vectors above. For example, any other vector known in the art, such as bacteriophage or cosmid vectors, can be used. In particular, for example, pBluescriptII SK+ (manufactured by Stratagene Corporation) is preferable.

(Mutation of Amadoriase Gene)

Mutation of an amadoriase gene can be performed by any known method depending on the intended form of mutation. More specifically, methods of bringing a chemical mutagen into contact with and allowing to act on an amadoriase gene or recombinant DNA comprising such gene integrated therein, ultraviolet irradiation methods, genetic engineering techniques, methods making extensive use of protein engineering techniques, or various other methods can be extensively used.

Examples of chemical mutagens used in the aforementioned mutation include hydroxylamine, N-methyl-N'-nitro-N-nitrosoguanidine, nitrous acid, sulfurous acid, hydrazine, formic acid, and 5-bromouracil.

Various conditions for the contact/reactions may be employed depending on the type of a drug to be used, and such conditions are not particularly limited where a desired mutation can be actually induced in an amadoriase gene. In general, the desired mutation can be induced by contact/reactions performed at 20° C. to 80° C. for 10 minutes or longer, and preferably 10 to 180 minutes, with the use of the drug mentioned above at concentrations of from 0.5 M to 12 M. The ultraviolet irradiation may also be performed according to conventional techniques as described above (Gendai Kagaku, pp. 24-30, June, 1989).

As the method making extensive use of protein engineering techniques a technique known as site-specific mutagenesis can, in general, be used. Examples include the Kramer method (Nucleic Acids Res., 12, 9441, 1984; Methods Enzymol., 154, 350, 1987; and Gene, 37, 73, 1985), the Eckstein method (Nucleic Acids Res., 13, 8749, 1985; Nucleic Acids Res., 13, 8765, 1985; and Nucleic Acids Res, 14, 9679, 1986), and the Kunkel method (Proc. Natl. Acid. Sci. U.S.A., 82, 488, 1985; and Methods Enzymol., 154, 367, 1987). Examples of a specific method of conversion of a nucleotide sequence in DNA include the use of a commercially available kit (Transformer Mutagenesis Kit, Clonetech; EXOIII/Mung Bean Deletion Kit, Stratagene; or Quick Change Site Directed Mutagenesis Kit, Stratagene).

The technique known as the general polymerization chain reaction (PCR) technique can also be used (Technique, 1, 11, 1989). In addition to the conventional genetic mutation techniques above, the modified amadoriase genes of interest can also be directly synthesized by an organic synthesis method or enzyme synthesis method.

The nucleotide sequences of DNA encoding the amadoriase genes obtained by the methods mentioned above may be determined or verified by, for example, using a multi-capillary DNA analysis system, CEQ2000 (Beckman Coulter Inc.).

(Transformation/Transduction)

The amadoriase genes obtained as described above may be integrated into a vector such as a bacteriophage vector, a cosmid vector, or a plasmid vector used in transformation of a prokaryotic or eukaryotic cell by a conventional technique, and a host corresponding to each vector can be transformed or transduced by conventional techniques. For example, a host of interest, such as a microorganism belonging to the genus *Escherichia*, which specifically may be a strain of *E. coli* K-12, preferably a strain of *E. coli* JM109, *E. coli* DH5a (manufactured by Takara Bio Inc.), a strain of *E. coli* B, or preferably a strain of *E. coli* BL21 (manufactured by NIP-PON GENE CO., LTD.) may be transformed using the obtained recombinant DNA, or such recombinant DNA may be transduced into the host cells, so as to obtain the resulting strain.

(Amino Acid Sequence Identity or Similarity)

The amino acid sequence identity or similarity can be computed by a program such as maximum matching or search homology of GENETYX Ver. 11 (manufactured by GENETYX) or a program such as maximum matching or multiple alignment of DNASIS Pro (manufactured by Hitachi Solutions, Ltd.). In order to compute amino acid sequence identity, two or more amadoriases may be aligned, and the positions of identical amino acids in such two or more amadoriases may be determined. The identical regions in amino acid sequences can be determined based on such information.

Further, positions having similar amino acids in two or more amadoriases may be examined. For example, a plurality of amino acid sequences can be subjected to alignment using CLUSTALW and, in such case, Blosum62 can be used as the algorithm and a plurality of amino acid sequences can be subjected to alignment and amino acids determined to be similar as a result of such alignment may be referred to as "similar amino acids." In the variant of the present invention, amino acid substitution can be carried out between such similar amino acids. By carrying out such alignments, it is possible to examine regions having identical amino acid sequences and positions being occupied by similar amino acids regarding a plurality of amino acid sequences. Based on such information, homologous regions (conserved regions) in the amino acid sequences can be determined.

Figures 1, 3:
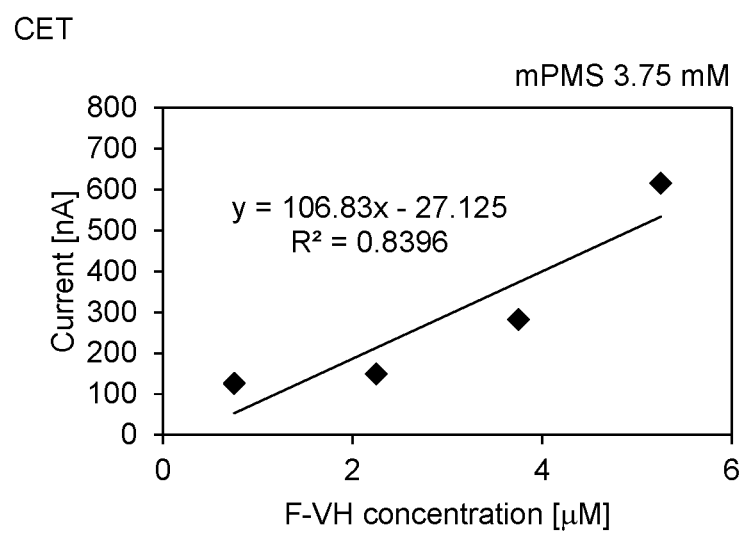
Figures 2, 3:
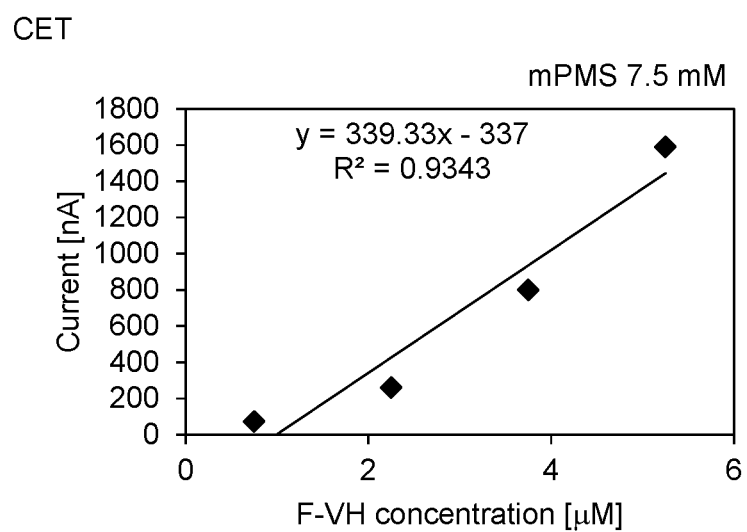

The term "homologous region(s)" used herein refers to region(s) consisting of identical or similar amino acids at corresponding positions in the reference amadoriase and in the comparative amadoriase, when two or more amadoriases are aligned, wherein said region(s) consist(s) of 3 or more, 4 or more, 5 or more, 6 or more, 7 or more, 8 or more, 9 or more, or 10 or more continuous amino acids. For example, FIG. 1 shows the alignment of amadoriases exhibiting 74% or higher sequence identity over the full-length amino acid sequences. In such sequences, the region of positions 10 to 32 with reference to the sequence of the amadoriase derived from *Coniochaeta* sp. as shown in SEQ ID NO: 1 consists of identical or similar amino acids, and, therefore, such region falls under a homologous region. Similarly, regions of positions 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 with reference to the sequence of the amadoriase derived from *Coniochaeta* sp. as shown in SEQ ID NO: 1 can be (can fall under) homologous regions.

Preferably, the homologous region of an amadoriase is the region consisting of amino acid sequences of positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410 with reference to the sequence of the amadoriase derived from *Coniochaeta* sp. as shown in SEQ ID NO: 1.

More preferably, the homologous region of an amadoriase is the region consisting of amino acid sequences of positions 11 to 18, 20 to 32, 50 to 52, 54 to 58, 266 to 268, 270 to 273, 277 to 286, and 370 to 383 with reference to the sequence of the amadoriase derived from *Coniochaeta* sp. as shown in SEQ ID NO: 1.

When the full-length amino acid sequence of the amadoriase variant of the present invention is aligned with that of the amadoriase comprising the amino acid sequence as shown in SEQ ID NO: 1, SEQ ID NO: 3, SEQ ID NO: 6, SEQ ID NO: 9, SEQ ID NO: 10, SEQ ID NO: 11, SEQ ID NO: 44, SEQ ID NO: 53, or SEQ ID NO: 67, the sequence identity is, for example, 50% or higher, 60% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher, and such amadoriase variant has a dehydrogenase activity. In addition, the amino acid sequence in the homologous region of the amadoriase variant according to the present invention exhibits, for example, 75% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher sequence identity with the amino acid sequence in the homologous region of SEQ ID NO: 1.

(Identification of Positions Corresponding to Amino Acids)

The term (the) "position corresponding to the amino acid" refers to the position in an amino acid sequence of an amadoriase derived from another organism species that corresponds to the amino acid at a particular position in the amino acid sequence of an amadoriase derived from the genus *Coniochaeta* as shown in SEQ ID NO: 1.

As an exemplary method of identifying the "position corresponding to the amino acid", amino acid sequences may be compared using a known algorithm such as the Lipman-Pearson method to assign maximum identity to conserved amino acid residues present in the amino acid sequence of each amadoriase. The positions of the homologous amino acid residues in each of the amadoriase sequences can be determined, regardless of insertion or deletion of amino acid residue(s) in the amino acid sequences by aligning the amino acid sequences of the amadoriases by such method. Homologous positions are considered to exist in the same positions in the three-dimensional structures, and amino acid residues at such homologous positions are expected to exert similar effects in terms of specificity of the amadoriase of interest.

FIGS. 1-1, 1-2, 1-3, 1-4, and 1-5 show sequences of amadoriases derived from various types of known organism species. The amino acid sequence as shown in SEQ ID NO:

1 is shown on the uppermost line. Various sequences shown in FIG. 1 each have 70% or higher sequence identity with the sequence as shown in SEQ ID NO: 1 and these sequences are aligned using a known algorithm. The sites of mutations in the variants according to the present invention are shown in the figures. Based on FIGS. 1-1, 1-2, 1-3, 1-4, and 1-5, the sites of mutations in the amino acid sequence of the amadoriase derived from other organism species corresponding to the amino acid at the particular position in the amino acid sequence of the amadoriase belonging to the genus *Coniochaeta* can be identified. FIGS. 1-1, 1-2, 1-3, 1-4, and 1-5 show amino acid sequences of the amadoriase derived from the genus *Coniochaeta* (SEQ ID NO: 1), the amadoriase derived from *Eupenicillium terrenum* (SEQ ID NO: 3), the ketoamine oxidase derived from *Pyrenochaeta* sp. (SEQ ID NO: 4), the ketoamine oxidase derived from *Arthrinium* sp. (SEQ ID NO: 5), the ketoamine oxidase derived from *Curvularia clavata* (SEQ ID NO: 6), the ketoamine oxidase derived from *Neocosmospora vasinfecta* (SEQ ID NO: 7), the fructosyl amino acid oxidase derived from *Cryptococcus neoformans* (SEQ ID NO: 8), the fructosyl peptide oxidase derived from *Phaeosphaeria nodorum* (SEQ ID NO: 9), the fructosyl amino acid oxidase derived from *Aspergillus nidulans* (SEQ ID NO: 10), the fructosyl peptide oxidase derived from *Emericella nidulans* (SEQ ID NO: 11), the fructosyl amino acid oxidase derived from *Ulocladium* sp. (SEQ ID NO: 12), and the fructosyl amino acid oxidase derived from *Penicillium janthinellum* (SEQ ID NO: 13).

(Positions Corresponding to Sites of Substitutions)

In the present invention, the amino acid at "the position corresponding to cysteine at position 280 in the amino acid sequence as shown in SEQ ID NO: 1" is the amino acid corresponding to cysteine at position 280 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid residue of interest can be identified based on FIG. 1-3 showing the amino acid sequences aligned using the method for identifying an "amino acid at a position corresponding (or equivalent) to (the amino acid of interest)" described above.

Specifically, the amino acid at "the position corresponding to cysteine at position 280 in the amino acid sequence as shown in SEQ ID NO: 1" is cysteine at position 280 in the case of the amadoriase derived from *Eupenicillium terrenum*, cysteine at position 278 in the case of the ketoamine oxidase derived from *Pyrenochaeta* sp., cysteine at position 280 in the case of the ketoamine oxidase derived from *Arthrinium* sp., cysteine at position 278 in the case of the ketoamine oxidase derived from *Curvularia clavata*, cysteine at position 280 in the case of the ketoamine oxidase derived from *Neocosmospora vasinfecta*, cysteine at position 280 in the case of the fructosyl amino acid oxidase derived from *Cryptococcus neoformans*, cysteine at position 276 in the case of the fructosyl peptide oxidase derived from *Phaeosphaeria nodorum*, cysteine at position 280 in the case of the fructosyl amino acid oxidase derived from *Aspergillus nidulans*, cysteine at position 280 in the case of the fructosyl peptide oxidase derived from *Emericella nidulans*, cysteine at position 278 in the case of the fructosyl amino acid oxidase derived from *Ulocladium* sp., and cysteine at position 280 in the case of the fructosyl amino acid oxidase derived from *Penicillium janthinellum*.

The amino acid at "the position corresponding to phenylalanine at position 267 in the amino acid sequence as shown in SEQ ID NO: 1" is the amino acid corresponding to phenylalanine at position 267 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1-3 showing the amino acid sequences aligned using the method described above.

Specifically, the amino acid at "the position corresponding to phenylalanine at position 267 in the amino acid sequence as shown in SEQ ID NO: 1" is phenylalanine at position 267 in the case of the amadoriase derived from *Eupenicillium terrenum*, phenylalanine at position 265 in the case of the ketoamine oxidase derived from *Pyrenochaeta* sp., phenylalanine at position 267 in the case of the ketoamine oxidase derived from *Arthrinium* sp., phenylalanine at position 265 in the case of the ketoamine oxidase derived from *Curvularia clavata*, phenylalanine at position 267 in the case of the ketoamine oxidase derived from *Neocosmospora vasinfecta*, phenylalanine at position 267 in the case of the fructosyl amino acid oxidase derived from *Cryptococcus neoformans*, phenylalanine at position 263 in the case of the fructosyl peptide oxidase derived from *Phaeosphaeria nodorum*, phenylalanine at position 267 in the case of the fructosyl amino acid oxidase derived from *Aspergillus nidulans*, phenylalanine at position 267 in the case of the fructosyl peptide oxidase derived from *Emericella nidulans*, phenylalanine at position 265 in the case of the fructosyl amino acid oxidase derived from *Ulocladium* sp., and phenylalanine at position 267 in the case of the fructosyl amino acid oxidase derived from *Penicillium janthinellum*.

The amino acid at "the position corresponding to phenylalanine at position 269 in the amino acid sequence as shown in SEQ ID NO: 1" is the amino acid corresponding to phenylalanine at position 269 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1-3 showing the amino acid sequences aligned using the method described above.

Specifically, the amino acid at "the position corresponding to phenylalanine at position 269 in the amino acid sequence as shown in SEQ ID NO: 1" is phenylalanine at position 269 in the case of the amadoriase derived from *Eupenicillium terrenum*, phenylalanine at position 267 in the case of the ketoamine oxidase derived from *Pyrenochaeta* sp., phenylalanine at position 269 in the case of the ketoamine oxidase derived from *Arthrinium* sp., phenylalanine at position 267 in the case of the ketoamine oxidase derived from *Curvularia clavata*, phenylalanine at position 269 in the case of the ketoamine oxidase derived from *Neocosmospora vasinfecta*, phenylalanine at position 269 in the case of the fructosyl amino acid oxidase derived from *Cryptococcus neoformans*, phenylalanine at position 265 in the case of the fructosyl peptide oxidase derived from *Phaeosphaeria nodorum*, phenylalanine at position 269 in the case of the fructosyl amino acid oxidase derived from *Aspergillus nidulans*, isoleucine at position 269 in the case of the fructosyl peptide oxidase derived from *Emericella nidulans*, phenylalanine at position 267 in the case of the fructosyl amino acid oxidase derived from *Ulocladium* sp., and phenylalanine at position 269 in the case of the fructosyl amino acid oxidase derived from *Penicillium janthinellum*.

The amino acid at "the position corresponding to aspartic acid at position 54 in the amino acid sequence as shown in SEQ ID NO: 1" is the amino acid corresponding to aspartic acid at position 54 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1-1 showing the amino acid sequences aligned using the method described above.

Specifically, the amino acid at "the position corresponding to aspartic acid at position 54 in the amino acid sequence as shown in SEQ ID NO: 1" is aspartic acid at position 54 in the case of the amadoriase derived from *Eupenicillium terrenum*, aspartic acid at position 54 in the case of the ketoamine oxidase derived from *Pyrenochaeta* sp., aspartic acid at position 54 in the case of the ketoamine oxidase derived from *Arthrinium* sp., aspartic acid at position 54 in the case of the ketoamine oxidase derived from *Curvularia clavata*, aspartic acid at position 54 in the case of the ketoamine oxidase derived from *Neocosmospora vasinfecta*, aspartic acid at position 54 in the case of the fructosyl amino acid oxidase derived from *Cryptococcus neoformans*, aspartic acid at position 54 in the case of the fructosyl peptide oxidase derived from *Phaeosphaeria nodorum*, aspartic acid at position 53 in the case of the fructosyl amino acid oxidase derived from *Aspergillus nidulans*, aspartic acid at position 53 in the case of the fructosyl peptide oxidase derived from *Emericella nidulans*, aspartic acid at position 54 in the case of the fructosyl amino acid oxidase derived from *Ulocladium* sp., and aspartic acid at position 54 in the case of the fructosyl amino acid oxidase derived from *Penicillium janthinellum*.

The amino acid at "the position corresponding to tyrosine at position 241 in the amino acid sequence as shown in SEQ ID NO: 1" is the amino acid corresponding to tyrosine at position 241 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1-3 showing the amino acid sequences aligned using the method described above.

Specifically, the amino acid at "the position corresponding to tyrosine at position 241 in the amino acid sequence as shown in SEQ ID NO: 1" is phenylalanine at position 241 in the case of the amadoriase derived from *Eupenicillium terrenum*, tyrosine at position 239 in the case of the ketoamine oxidase derived from *Pyrenochaeta* sp., tyrosine at position 241 in the case of the ketoamine oxidase derived from *Arthrinium* sp., tyrosine at position 239 in the case of the ketoamine oxidase derived from *Curvularia clavata*, tyrosine at position 241 in the case of the ketoamine oxidase derived from *Neocosmospora vasinfecta*, tyrosine at position 241 in the case of the fructosyl amino acid oxidase derived from *Cryptococcus neoformans*, tyrosine at position 237 in the case of the fructosyl peptide oxidase derived from *Phaeosphaeria nodorum*, phenylalanine at position 241 in the case of the fructosyl amino acid oxidase derived from *Aspergillus nidulans*, phenylalanine at position 241 in the case of the fructosyl peptide oxidase derived from *Emericella nidulans*, tyrosine at position 239 in the case of the fructosyl amino acid oxidase derived from *Ulocladium* sp., and phenylalanine at position 241 in the case of the fructosyl amino acid oxidase derived from *Penicillium janthinellum*.

(Positions Corresponding to Mutation for Modification of Substrate Specificity)

The amino acid at "the position corresponding to arginine at position 62 in the amino acid sequence as shown in SEQ ID NO: 1" is the amino acid corresponding to arginine at position 62 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid residue of interest can be identified through alignment of amino acid sequences by the method for identifying the "amino acid at the position corresponding to (the amino acid of interest)" described above.

Specifically, the amino acid at "the position corresponding to arginine at position 62 in the amino acid sequence as shown in SEQ ID NO: 1" is arginine at position 62 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl amino acid oxidase derived from *Cryptococcus neoformans*, the fructosyl amino acid oxidase derived from *Ulocladium* sp., and the fructosyl amino acid oxidase derived from *Penicillium janthinellum*, serine at position 62 in the case of the fructosyl peptide oxidase derived from *Phaeosphaeria nodorum*, arginine at position 61 in the case of the fructosyl peptide oxidase derived from *Emericella nidulans*, and arginine at position 61 in the case of the fructosyl amino acid oxidase derived from *Aspergillus nidulans*.

In the present invention, the amino acid at "the position corresponding to leucine at position 63 in the amino acid sequence as shown in SEQ ID NO: 1" is the amino acid corresponding to leucine at position 63 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and the amino acid of interest can be identified by the method for identifying the "amino acid at the position corresponding to (the amino acid of interest)" described above.

Specifically, the amino acid at "the position corresponding to leucine at position 63 in the amino acid sequence as shown in SEQ ID NO: 1" is leucine at position 63 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl peptide oxidase derived from *Phaeosphaeria nodorum*, the fructosyl amino acid oxidase derived from *Ulocladium* sp., and the fructosyl amino acid oxidase derived from *Penicillium janthinellum*, isoleucine at position 63 in the case of the fructosyl amino acid oxidase derived from *Cryptococcus neoformans*, and leucine at position 62 in the case of the fructosyl amino acid oxidase derived from *Aspergillus nidulans* and the fructosyl peptide oxidase derived from *Emericella nidulans*.

In the present invention, the amino acid at "the position corresponding to glutamic acid at position 102 in the amino acid sequence as shown in SEQ ID NO: 1" is the amino acid corresponding to glutamic acid at position 102 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and the amino acid of interest can be identified by the method for identifying the "amino acid at the position corresponding to (the amino acid of interest)" described above.

Specifically, the amino acid at "the position corresponding to glutamic acid at position 102 in the amino acid sequence as shown in SEQ ID NO: 1" is glutamic acid at position 102 in the case of the amadoriase derived from *Eupenicillium terrenum*, the ketoamine oxidase derived from *Curvularia clavata*, the ketoamine oxidase derived from *Neocosmospora vasinfecta*, the fructosyl amino acid oxidase derived from *Cryptococcus neoformans*, and the fructosyl amino acid oxidase derived from *Penicillium janthinellum*, lysine at position 102 in the case of the ketoamine oxidase derived from *Pyrenochaeta* sp., the ketoamine oxidase derived from *Arthrinium* sp., the fructosyl peptide oxidase derived from *Phaeosphaeria nodorum*, and the fructosyl amino acid oxidase derived from *Ulocladium* sp., and glutamic acid at position 101 in the case of the fructosyl peptide oxidase derived from *Emericella nidulans* and the fructosyl amino acid oxidase derived from *Aspergillus nidulans*.

In the present invention, the amino acid at "the position corresponding to aspartic acid at position 106 in the amino acid sequence as shown in SEQ ID NO: 1" is the amino acid corresponding to aspartic acid at position 106 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and the amino acid of interest can be identified by the method for identifying the "amino acid at the position corresponding to (the amino acid of interest)" described above.

Specifically, the amino acid at "the position corresponding to aspartic acid at position 106 in the amino acid sequence as shown in SEQ ID NO: 1" is asparagine at position 106 in the case of the amadoriase derived from *Eupenicillium terrenum*, aspartic acid at position 106 in the case of the ketoamine oxidase derived from *Pyrenochaeta* sp., the ketoamine oxidase derived from *Curvularia clavata*, the fructosyl peptide oxidase derived from *Phaeosphaeria nodorum*, and the fructosyl amino acid oxidase derived from *Ulocladium* sp., alanine at position 106 in the case of the ketoamine oxidase derived from *Arthrinium* sp., glycine at position 106 in the case of the ketoamine oxidase derived from *Neocosmospora vasinfecta*, serine at position 106 in the case of the fructosyl amino acid oxidase derived from *Cryptococcus neoformans* and the fructosyl amino acid oxidase derived from *Penicillium janthinellum*, lysine at position 105 in the case of the fructosyl peptide oxidase derived from *Emericella nidulans*, and glycine at position 105 in the case of the fructosyl amino acid oxidase derived from *Aspergillus nidulans*.

In the present invention, the amino acid at "the position corresponding to glutamine at position 110 in the amino acid sequence as shown in SEQ ID NO: 1" is the amino acid corresponding to glutamine at position 110 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and the amino acid of interest can be identified by the method for identifying the "amino acid at the position corresponding to (the amino acid of interest)" described above.

Specifically, the amino acid at "the position corresponding to glutamine at position 110 in the amino acid sequence as shown in SEQ ID NO: 1" is lysine at position 110 in the case of the amadoriase derived from *Eupenicillium terrenum* and the fructosyl amino acid oxidase derived from *Penicillium janthinellum*, alanine at position 110 in the case of the ketoamine oxidase derived from *Pyrenochaeta* sp., the ketoamine oxidase derived from *Curvularia clavata*, and the fructosyl amino acid oxidase derived from *Ulocladium* sp., glutamine at position 110 in the case of the ketoamine oxidase derived from *Arthrinium* sp., glutamic acid at position 110 in the case of the ketoamine oxidase derived from *Neocosmospora vasinfecta*, serine at position 110 in the case of the fructosyl amino acid oxidase derived from *Cryptococcus neoformans*, glycine at position 110 in the case of the fructosyl peptide oxidase derived from *Phaeosphaeria nodorum*, arginine at position 109 in the case of the fructosyl peptide oxidase derived from *Emericella nidulans*, and lysine at position 109 in the case of the fructosyl amino acid oxidase derived from *Aspergillus nidulans*.

In the present invention, the amino acid at "the position corresponding to alanine at position 113 in the amino acid sequence as shown in SEQ ID NO: 1" is the amino acid corresponding to alanine at position 113 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and the amino acid of interest can be identified by the method for identifying the "amino acid at the position corresponding to (the amino acid of interest)" described above.

Specifically, the amino acid at "the position corresponding to alanine at position 113 in the amino acid sequence as shown in SEQ ID NO: 1" is threonine at position 113 in the case of the amadoriase derived from *Eupenicillium terrenum*, the ketoamine oxidase derived from *Pyrenochaeta* sp., and the ketoamine oxidase derived from *Arthrinium* sp., alanine at position 113 in the case of the ketoamine oxidase derived from *Curvularia clavata*, the fructosyl amino acid oxidase derived from *Cryptococcus neoformans*, the fructosyl peptide oxidase derived from *Phaeosphaeria nodorum*, and the fructosyl amino acid oxidase derived from *Ulocladium* sp., lysine at position 113 in the case of the ketoamine oxidase derived from *Neocosmospora vasinfecta*, serine at position 112 in the case of the fructosyl amino acid oxidase derived from *Aspergillus nidulans* and the fructosyl peptide oxidase derived from *Emericella nidulans*, and aspartic acid at position 113 in the case of the fructosyl amino acid oxidase derived from *Penicillium janthinellum*.

In the present invention, the amino acid at "the position corresponding to alanine at position 355 in the amino acid sequence as shown in SEQ ID NO: 1" is the amino acid corresponding to alanine at position 355 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and the amino acid of interest can be identified by the method for identifying the "amino acid at the position corresponding to (the amino acid of interest)" described above.

Specifically, the amino acid at "the position corresponding to alanine at position 355 in the amino acid sequence as shown in SEQ ID NO: 1" is alanine at position 355 in the case of the amadoriase derived from *Eupenicillium terrenum*, the fructosyl amino acid oxidase derived from *Cryptococcus neoformans*, the fructosyl amino acid oxidase derived from *Aspergillus nidulans*, the fructosyl peptide oxidase derived from *Emericella nidulans*, and the fructosyl amino acid oxidase derived from *Penicillium janthinellum*, alanine at position 353 in the case of the ketoamine oxidase derived from *Pyrenochaeta* sp., the ketoamine oxidase derived from *Curvularia clavata*, and the fructosyl amino acid oxidase derived from *Ulocladium* sp., alanine at position 356 in the case of the ketoamine oxidase derived from *Arthrinium* sp., serine at position 355 in the case of the ketoamine oxidase derived from *Neocosmospora vasinfecta*, and alanine at position 351 in the case of the fructosyl peptide oxidase derived from *Phaeosphaeria nodorum*.

In the present invention, the amino acid at "the position corresponding to alanine at position 419 in the amino acid sequence as shown in SEQ ID NO: 1" is the amino acid corresponding to alanine at position 419 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and the amino acid of interest can be identified by the method for identifying the "amino acid at the position corresponding to (the amino acid of interest)" described above.

Specifically, the amino acid at "the position corresponding to alanine at position 419 in the amino acid sequence as shown in SEQ ID NO: 1" is glycine at position 419 in the case of the amadoriase derived from *Eupenicillium terrenum*, alanine at position 418 in the case of the ketoamine oxidase derived from *Pyrenochaeta* sp., the ketoamine oxidase derived from *Curvularia clavata*, and the fructosyl amino acid oxidase derived from *Ulocladium* sp., alanine at position 421 in the case of the ketoamine oxidase derived from *Arthrinium* sp., alanine at position 420 in the case of the ketoamine oxidase derived from *Neocosmospora vasinfecta*, the fructosyl amino acid oxidase derived from *Cryptococcus neoformans*, and the fructosyl peptide oxidase derived from *Emericella nidulans*, serine at position 416 in the case of the fructosyl peptide oxidase derived from *Phaeosphaeria nodorum*, serine at position 419 in the case of the fructosyl amino acid oxidase derived from *Penicillium janthinellum*, and alanine at position 420 in the case of the fructosyl amino acid oxidase derived from *Aspergillus nidulans*.

In the present invention, the amino acid at "the position corresponding to aspartic acid at position 68 in the amino acid sequence as shown in SEQ ID NO: 1" is the amino acid corresponding to aspartic acid at position 68 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and the amino acid of interest can be identified by the method for identifying the "amino acid at the position corresponding to (the amino acid of interest)" described above.

Specifically, the amino acid at "the position corresponding to aspartic acid at position 68 in the amino acid sequence as shown in SEQ ID NO: 1" is aspartic acid at position 68 in the case of the amadoriase derived from *Eupenicillium terrenum*, the ketoamine oxidase derived from *Pyrenochaeta* sp., the ketoamine oxidase derived from *Arthrinium* sp., the ketoamine oxidase derived from *Curvularia clavata*, the ketoamine oxidase derived from *Neocosmospora vasinfecta*, the fructosyl amino acid oxidase derived from *Cryptococcus neoformans*, the fructosyl peptide oxidase derived from *Phaeosphaeria nodorum*, the fructosyl amino acid oxidase derived from *Ulocladium* sp., and the fructosyl amino acid oxidase derived from *Penicillium janthinellum* and aspartic acid at position 67 in the case of the fructosyl peptide oxidase derived from *Emericella nidulans*, and the fructosyl amino acid oxidase derived from *Aspergillus nidulans*.

In the present invention, the amino acid at "the position corresponding to alanine at position 356 in the amino acid sequence as shown in SEQ ID NO: 1" is the amino acid corresponding to alanine at position 356 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and the amino acid of interest can be identified by the method for identifying the "amino acid at the position corresponding to (the amino acid of interest)" described above.

Specifically, the amino acid at "the position corresponding to alanine at position 356 in the amino acid sequence as shown in SEQ ID NO: 1" is asparagine at position 356 in the case of the amadoriase derived from *Eupenicillium terrenum*, alanine at position 354 in the case of the ketoamine oxidase derived from *Pyrenochaeta* sp., alanine at position 357 in the case of the ketoamine oxidase derived from *Arthrinium* sp., alanine at position 354 in the case of the ketoamine oxidase derived from *Curvularia clavata*, alanine at position 356 in the case of the ketoamine oxidase derived from *Neocosmospora vasinfecta*, asparagine at position 356 in the case of the fructosyl amino acid oxidase derived from *Cryptococcus neoformans*, alanine at position 352 in the case of the fructosyl peptide oxidase derived from *Phaeosphaeria nodorum*, asparagine at position 356 in the case of the fructosyl amino acid oxidase derived from *Aspergillus nidulans*, asparagine at position 356 in the case of the fructosyl peptide oxidase derived from *Emericella nidulans*, alanine at position 354 in the case of the fructosyl amino acid oxidase derived from *Ulocladium* sp., and asparagine at position 356 in the case of the fructosyl amino acid oxidase derived from *Penicillium janthinellum*.

(Corresponding Positions of Mutations for Improvement of Surfactant Tolerance)

In the present invention, the amino acid at "the position corresponding to glutamic acid at position 44 in the amino acid sequence as shown in SEQ ID NO: 1" is the amino acid corresponding to glutamic acid at position 44 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid of interest can be identified based on FIG. 1 showing the amino acid sequences aligned using the method for identifying the "amino acid at the position corresponding to (an amino acid of interest)."

Specifically, the amino acid at "the position corresponding to glutamic acid at position 44 in the amino acid sequence as shown in SEQ ID NO: 1" is lysine at position 44 in the case of the amadoriase derived from *Eupenicillium terrenum*, proline at position 44 in the case of the ketoamine oxidase derived from *Pyrenochaeta* sp., proline at position 44 in the case of the ketoamine oxidase derived from *Arthrinium* sp., proline at position 44 in the case of the ketoamine oxidase derived from *Curvularia clavata*, proline at position 44 in the case of the ketoamine oxidase derived from *Neocosmospora vasinfecta*, leucine at position 44 in the case of the fructosyl amino acid oxidase derived from *Cryptococcus neoformans*, proline at position 44 in the case of the fructosyl peptide oxidase derived from *Phaeosphaeria nodorum*, proline at position 43 in the case of the fructosyl amino acid oxidase derived from *Aspergillus nidulans*, proline at position 43 in the case of the fructosyl peptide oxidase derived from *Emericella nidulans*, proline at position 44 in the case of the fructosyl amino acid oxidase derived from *Ulocladium* sp., and proline at position 44 in the case of the fructosyl amino acid oxidase derived from *Penicillium janthinellum*.

The amino acid at "the position corresponding to glutamic acid at position 81 in the amino acid sequence as shown in SEQ ID NO: 1" is the amino acid corresponding to glutamic acid at position 81 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to glutamic acid at position 81 in the amino acid sequence as shown in SEQ ID NO: 1" is asparagine at position 81 in the case of the amadoriase derived from *Eupenicillium terrenum*, glutamic acid at position 81 in the case of the ketoamine oxidase derived from *Pyrenochaeta* sp., histidine at position 81 in the case of the ketoamine oxidase derived from *Arthrinium* sp., glutamic acid at position 81 in the case of the ketoamine oxidase derived from *Curvularia clavata*, asparagine at position 81 in the case of the ketoamine oxidase derived from *Neocosmospora vasinfecta*, asparagine at position 81 in the case of the fructosyl amino acid oxidase derived from *Cryptococcus neoformans*, glutamic acid at position 81 in the case of the fructosyl peptide oxidase derived from *Phaeosphaeria nodorum*, asparagine at position 80 in the case of the fructosyl amino acid oxidase derived from *Aspergillus nidulans*, asparagine at position 80 in the case of the fructosyl peptide oxidase derived from *Emericella nidulans*, glutamic acid at position 81 in the case of the fructosyl amino acid oxidase derived from *Ulocladium* sp., and asparagine at position 81 in the case of the fructosyl amino acid oxidase derived from *Penicillium janthinellum*.

The amino acid at "the position corresponding to glutamic acid at position 133 in the amino acid sequence as shown in SEQ ID NO: 1" is the amino acid corresponding to glutamic acid at position 133 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to glutamic acid at position 133 in the amino acid sequence as shown in SEQ ID NO: 1" is glutamic acid at position 133 in the case of the amadoriase derived from *Eupenicillium terrenum*, glutamic acid at position 133 in the case of the ketoamine oxidase derived from *Pyrenochaeta* sp., alanine at position 133 in the case of the ketoamine oxidase derived from *Arthrinium* sp., glutamic acid at position 133 in the case of the ketoamine oxidase derived from *Curvularia clavata*, alanine at position 133 in the case of the ketoamine oxidase derived from *Neocosmospora vasinfecta*, glutamic acid at position 133 in the case of the fructosyl amino acid oxidase derived from *Cryptococcus neoformans*, glutamic acid at position 131 in the case of the fructosyl peptide oxidase derived from *Phaeosphaeria nodorum*, glutamic acid at position 132 in the case of the fructosyl amino acid oxidase derived from *Aspergillus nidulans*, glutamic acid at position 132 in the case of the fructosyl peptide oxidase derived from *Emericella nidulans*, lysine at position 133 in the case of the fructosyl amino acid oxidase derived from *Ulocladium* sp., and aspartic acid at position 133 in the case of the fructosyl amino acid oxidase derived from *Penicillium janthinellum*.

The amino acid at "the position corresponding to glutamic acid at position 253 in the amino acid sequence as shown in SEQ ID NO: 1" is the amino acid corresponding to glutamic acid at position 253 in the amino acid sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to glutamic acid at position 253 in the amino acid sequence as shown in SEQ ID NO: 1" is alanine at position 253 in the case of the amadoriase derived from *Eupenicillium terrenum*, alanine at position 251 in the case of the ketoamine oxidase derived from *Pyrenochaeta* sp., glutamic acid at position 253 in the case of the ketoamine oxidase derived from *Arthrinium* sp., glutamic acid at position 251 in the case of the ketoamine oxidase derived from *Curvularia clavata*, valine at position 253 in the case of the ketoamine oxidase derived from *Neocosmospora vasinfecta*, glutamic acid at position 253 in the case of the fructosyl amino acid oxidase derived from *Cryptococcus neoformans*, arginine at position 249 in the case of the fructosyl peptide oxidase derived from *Phaeosphaeria nodorum*, alanine at position 253 in the case of the fructosyl amino acid oxidase derived from *Aspergillus nidulans*, alanine at position 253 in the case of the fructosyl peptide oxidase derived from *Emericella nidulans*, glutamic acid at position 251 in the case of the fructosyl amino acid oxidase derived from *Ulocladium* sp., and glutamine at position 253 in the case of the fructosyl amino acid oxidase derived from *Penicillium janthinellum*.

The amino acid at "the position corresponding to glycine at position 256 in the amino acid sequence as shown in SEQ ID NO: 1" is the amino acid corresponding to glycine at position 256 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to glycine at position 256 in the amino acid sequence as shown in SEQ ID NO: 1" is asparagine at position 256 in the case of the amadoriase derived from *Eupenicillium terrenum*, aspartic acid at position 254 in the case of the ketoamine oxidase derived from *Pyrenochaeta* sp., glycine at position 256 in the case of the ketoamine oxidase derived from *Arthrinium* sp., asparagine at position 254 in the case of the ketoamine oxidase derived from *Curvularia clavata*, glycine at position 256 in the case of the ketoamine oxidase derived from *Neocosmospora vasinfecta*, glutamic acid at position 256 in the case of the fructosyl amino acid oxidase derived from *Cryptococcus neoformans*, asparagine at position 252 in the case of the fructosyl peptide oxidase derived from *Phaeosphaeria nodorum*, asparagine at position 256 in the case of the fructosyl amino acid oxidase derived from *Aspergillus nidulans*, asparagine at position 256 in the case of the fructosyl peptide oxidase derived from *Emericella nidulans*, asparagine at position 254 in the case of the fructosyl amino acid oxidase derived from *Ulocladium* sp., and aspartic acid at position 256 in the case of the fructosyl amino acid oxidase derived from *Penicillium janthinellum*.

The amino acid at "the position corresponding to valine at position 257 in the amino acid sequence as shown in SEQ ID NO: 1" is the amino acid corresponding to valine at position 257 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to valine at position 257 in the amino acid sequence as shown in SEQ ID NO: 1" is valine at position 257 in the case of the amadoriase derived from *Eupenicillium terrenum*, threonine at position 255 in the case of the ketoamine oxidase derived from *Pyrenochaeta* sp., cysteine at position 257 in the case of the ketoamine oxidase derived from *Arthrinium* sp., valine at position 255 in the case of the ketoamine oxidase derived from *Curvularia clavata*, cysteine at position 257 in the case of the ketoamine oxidase derived from *Neocosmospora vasinfecta*, cysteine at position 257 in the case of the fructosyl amino acid oxidase derived from *Cryptococcus neoformans*, serine at position 253 in the case of the fructosyl peptide oxidase derived from *Phaeosphaeria nodorum*, threonine at position 257 in the case of the fructosyl amino acid oxidase derived from *Aspergillus nidulans*, threonine at position 257 in the case of the fructosyl peptide oxidase derived from *Emericella nidulans*, valine at position 255 in the case of the fructosyl amino acid oxidase derived from *Ulocladium* sp., and valine at position 257 in the case of the fructosyl amino acid oxidase derived from *Penicillium janthinellum*.

The amino acid at "the position corresponding to asparagine at position 262 in the amino acid sequence as shown in SEQ ID NO: 1" is the amino acid corresponding to asparagine at position 262 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to asparagine at position 262 in the amino acid sequence as shown in SEQ ID NO: 1" is aspartic acid at position 262 in the case of the amadoriase derived from *Eupenicillium terrenum*, asparagine at position 260 in the case of the ketoamine oxidase derived from *Pyrenochaeta* sp., histidine at position 262 in the case of the ketoamine oxidase derived from *Arthrinium* sp., asparagine at position 260 in the case of the ketoamine oxidase derived from *Curvularia clavata*, histidine at position 262 in the case of the ketoamine oxidase derived from *Neocosmospora vasinfecta*, asparagine at position 262 in the case of the fructosyl amino acid oxidase derived from *Cryptococcus neoformans*, asparagine at position 258 in the case of the fructosyl peptide oxidase derived from *Phaeosphaeria nodorum*, aspartic acid at position 262 in the case of the fructosyl amino acid oxidase derived from *Aspergillus nidulans*, aspartic acid at position 262 in the case of the fructosyl peptide oxidase derived from *Emericella nidulans*, asparagine at position 260 in the case of the fructosyl amino acid oxidase derived from *Ulocladium* sp., and aspartic acid at position 262 in the case of the fructosyl amino acid oxidase derived from *Penicillium janthinellum*.

The amino acid at "the position corresponding to glutamine at position 337 in the amino acid sequence as shown in SEQ ID NO: 1" is the amino acid corresponding to glutamine at position 337 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to glutamine at position 337 in the amino acid sequence as shown in SEQ ID NO: 1" is lysine at position 337 in the case of the amadoriase derived from *Eupenicillium terrenum*, lysine at position 335 in the case of the ketoamine oxidase derived from *Pyrenochaeta* sp., glutamine at position 338 in the case of the ketoamine oxidase derived from *Arthrinium* sp., threonine at position 335 in the case of the ketoamine oxidase derived from *Curvularia clavata*, lysine at position 337 in the case of the ketoamine oxidase derived from *Neocosmospora vasinfecta*, lysine at position 337 in the case of the fructosyl amino acid oxidase derived from *Cryptococcus neoformans*, lysine at position 333 in the case of the fructosyl peptide oxidase derived from *Phaeosphaeria nodorum*, asparagine at position 337 in the case of the fructosyl amino acid oxidase derived from *Aspergillus nidulans*, asparagine at position 337 in the case of the fructosyl peptide oxidase derived from *Emericella nidulans*, threonine at position 335 in the case of the fructosyl amino acid oxidase derived from *Ulocladium* sp., and lysine at position 337 in the case of the fructosyl amino acid oxidase derived from *Penicillium janthinellum*.

The amino acid at "the position corresponding to glutamic acid at position 340 in the amino acid sequence as shown in SEQ ID NO: 1" is the amino acid corresponding to glutamic acid at position 340 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to glutamic acid at position 340 in the amino acid sequence as shown in SEQ ID NO: 1" is glutamic acid at position 340 in the case of the amadoriase derived from *Eupenicillium terrenum*, glutamic acid at position 338 in the case of the ketoamine oxidase derived from *Pyrenochaeta* sp., glutamic acid at position 341 in the case of the ketoamine oxidase derived from *Arthrinium* sp., glutamic acid at position 338 in the case of the ketoamine oxidase derived from *Curvularia clavata*, proline at position 340 in the case of the ketoamine oxidase derived from *Neocosmospora vasinfecta*, glutamic acid at position 340 in the case of the fructosyl amino acid oxidase derived from *Cryptococcus neoformans*, lysine at position 336 in the case of the fructosyl peptide oxidase derived from *Phaeosphaeria nodorum*, glutamic acid at position 340 in the case of the fructosyl amino acid oxidase derived from *Aspergillus nidulans*, glutamic acid at position 340 in the case of the fructosyl peptide oxidase derived from *Emericella nidulans*, glutamic acid at position 338 in the case of the fructosyl amino acid oxidase derived from *Ulocladium* sp., and glutamic acid at position 340 in the case of the fructosyl amino acid oxidase derived from *Penicillium janthinellum*.

The amino acid at "the position corresponding to aspartic acid at position 129 in the amino acid sequence as shown in SEQ ID NO: 1" is the amino acid corresponding to aspartic acid at position 129 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to aspartic acid at position 129 in the amino acid sequence as shown in SEQ ID NO: 1" is glutamic acid at position 129 in the case of the amadoriase derived from *Eupenicillium terrenum*, aspartic acid at position 129 in the case of the ketoamine oxidase derived from *Pyrenochaeta* sp., aspartic acid at position 129 in the case of the ketoamine oxidase derived from *Arthrinium* sp., aspartic acid at position 129 in the case of the ketoamine oxidase derived from *Curvularia clavata*, aspartic acid at position 129 in the case of the ketoamine oxidase derived from *Neocosmospora vasinfecta*, serine at position 129 in the case of the fructosyl amino acid oxidase derived from *Cryptococcus neoformans*, aspartic acid at position 127 in the case of the fructosyl peptide oxidase derived from *Phaeosphaeria nodorum*, glutamic acid at position 128 in the case of the fructosyl amino acid oxidase derived from *Aspergillus nidulans*, glutamic acid at position 128 in the case of the fructosyl peptide oxidase derived from *Emericella nidulans*, aspartic acid at position 129 in the case of the fructosyl amino acid oxidase derived from *Ulocladium* sp., and glutamic acid at position 129 in the case of the fructosyl amino acid oxidase derived from *Penicillium janthinellum*.

The amino acid at "the position corresponding to aspartic acid at position 132 in the amino acid sequence as shown in SEQ ID NO: 1" is the amino acid corresponding to aspartic acid at position 132 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to aspartic acid at position 132 in the amino acid sequence as shown in SEQ ID NO: 1" is aspartic acid at position 132 in the case of the amadoriase derived from *Eupenicillium terrenum*, aspartic acid at position 132 in the case of the ketoamine oxidase derived from *Pyrenochaeta* sp., aspartic acid at position 132 in the case of the ketoamine oxidase derived from *Arthrinium* sp., aspartic acid at position 132 in the case of the ketoamine oxidase derived from *Curvularia clavata*, glutamic acid at position 132 in the case of the ketoamine oxidase derived from *Neocosmospora vasinfecta*, aspartic acid at position 132 in the case of the fructosyl amino acid oxidase derived from *Cryptococcus neoformans*, aspartic acid at position 130 in the case of the fructosyl peptide oxidase derived from *Phaeosphaeria nodorum*, aspartic acid at position 131 in the case of the fructosyl amino acid oxidase derived from *Aspergillus nidulans*, aspartic acid at position 131 in the case of the fructosyl peptide oxidase derived from *Emericella nidulans*, aspartic acid at position 132 in the case of the fructosyl amino acid oxidase derived from *Ulocladium* sp., and aspartic acid at position 132 in the case of the fructosyl amino acid oxidase derived from *Penicillium janthinellum*.

The amino acid at "the position corresponding to glutamic acid at position 231 in the amino acid sequence as shown in SEQ ID NO: 1" is the amino acid corresponding to glutamic acid at position 231 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to glutamic acid at position 231 in the amino acid sequence as shown in SEQ ID NO: 1" is glutamic acid at position 231 in the case of the amadoriase derived from *Eupenicillium terrenum*, glutamic acid at position 229 in the case of the ketoamine oxidase derived from *Pyrenochaeta* sp., glutamic acid at position 231 in the case of the ketoamine oxidase derived from *Arthrinium* sp., glutamic acid at position 229 in the case of the ketoamine oxidase derived from *Curvularia clavata*, glutamic acid at position 231 in the case of the ketoamine oxidase derived from *Neocosmospora vasinfecta*, glutamic acid at position 231 in the case of the fructosyl amino acid oxidase derived from *Cryptococcus neoformans*, histidine at position 227 in the case of the fructosyl peptide oxidase derived from *Phaeosphaeria nodorum*, glutamic acid at position 231 in the case of the fructosyl amino acid oxidase derived from *Aspergillus nidulans*, glutamic acid at position 231 in the case of the fructosyl peptide oxidase derived from *Emericella nidulans*, glutamine at position 229 in the case of the fructosyl amino acid oxidase derived from *Ulocladium* sp., and glutamic acid at position 231 in the case of the fructosyl amino acid oxidase derived from *Penicillium janthinellum*.

The amino acid at "the position corresponding to aspartic acid at position 232 in the amino acid sequence as shown in SEQ ID NO: 1" is the amino acid corresponding to aspartic acid at position 232 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to aspartic acid at position 232 in the amino acid sequence as shown in SEQ ID NO: 1" is aspartic acid at position 232 in the case of the amadoriase derived from *Eupenicillium terrenum*, aspartic acid at position 230 in the case of the ketoamine oxidase derived from *Pyrenochaeta* sp., glutamic acid at position 232 in the case of the ketoamine oxidase derived from *Arthrinium* sp., aspartic acid at position 230 in the case of the ketoamine oxidase derived from *Curvularia clavata*, glutamic acid at position 232 in the case of the ketoamine oxidase derived from *Neocosmospora vasinfecta*, glycine at position 232 in the case of the fructosyl amino acid oxidase derived from *Cryptococcus neoformans*, glutamic acid at position 228 in the case of the fructosyl peptide oxidase derived from *Phaeosphaeria nodorum*, glutamic acid at position 232 in the case of the fructosyl amino acid oxidase derived from *Aspergillus nidulans*, glutamic acid at position 232 in the case of the fructosyl peptide oxidase derived from *Emericella nidulans*, aspartic acid at position 230 in the case of the fructosyl amino acid oxidase derived from *Ulocladium* sp., and aspartic acid at position 232 in the case of the fructosyl amino acid oxidase derived from *Penicillium janthinellum*.

The amino acid at "the position corresponding to glutamic acid at position 249 in the amino acid sequence as shown in SEQ ID NO: 1" is the amino acid corresponding to glutamic acid at position 249 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. This can also be identified based on FIG. 1 showing the amino acid sequences aligned using the method described above.

Specifically, the amino acid at "the position corresponding to glutamic acid at position 249 in the amino acid sequence as shown in SEQ ID NO: 1" is lysine at position 249 in the case of the amadoriase derived from *Eupenicillium terrenum*, lysine at position 247 in the case of the ketoamine oxidase derived from *Pyrenochaeta* sp., histidine at position 249 in the case of the ketoamine oxidase derived from *Arthrinium* sp., glutamic acid at position 247 in the case of the ketoamine oxidase derived from *Curvularia clavata*, glutamic acid at position 249 in the case of the ketoamine oxidase derived from *Neocosmospora vasinfecta*, glutamic acid at position 249 in the case of the fructosyl amino acid oxidase derived from *Cryptococcus neoformans*, glutamic acid at position 245 in the case of the fructosyl peptide oxidase derived from *Phaeosphaeria nodorum*, alanine at position 249 in the case of the fructosyl amino acid oxidase derived from *Aspergillus nidulans*, alanine at position 249 in the case of the fructosyl peptide oxidase derived from *Emericella nidulans*, serine at position 247 in the case of the fructosyl amino acid oxidase derived from *Ulocladium* sp., and glutamine at position 249 in the case of the fructosyl amino acid oxidase derived from *Penicillium janthinellum*.

(Corresponding Positions of Deletions for Improvement of Heat Stability)

The term "positions corresponding to 3 amino acid residues from the carboxyl terminus of the amadoriase sequence as shown in SEQ ID NO: 1" used herein refers to 3 amino acid residues from the carboxyl terminus of the amino acid sequence as shown in SEQ ID NO: 1, when the amino acid sequence of an amadoriase is compared with the amino acid sequence of an amadoriase derived from the genus *Coniochaeta* as shown in SEQ ID NO: 1. A sequence comprising 3 residues at this position in the amadoriase sequence derived from the genus *Coniochaeta* comprises proline at position 435, lysine at position 436, and leucine at position 437, and the amino acid sequence at positions corresponding thereto can be identified based on FIG. 1 showing the amino acid sequences aligned in the manner described above.

Specifically, 3 amino acid residues at the carboxyl terminus are alanine at position 435, histidine at position 436, and leucine at position 437 in the case of the amadoriase derived from *Eupenicillium terrenum*, 3 amino acid residues at the carboxyl terminus are alanine at position 438, lysine at position 439, and leucine at position 440 in the case of the ketoamine oxidase derived from *Pyrenochaeta* sp., 3 amino acid residues at the carboxyl terminus are histidine at position 450, lysine at position 451, and leucine at position 452 in the case of the ketoamine oxidase derived from *Arthrinium* sp., 3 amino acid residues at the carboxyl terminus are serine at position 438, lysine at position 439, and leucine at position 440 in the case of the ketoamine oxidase derived from *Curvularia clavata*, 3 amino acid residues at the carboxyl terminus are alanine at position 435, asparagine at position 436, and leucine at position 437 in the case of the fructosyl peptide oxidase derived from *Phaeosphaeria nodorum*, 3 amino acid residues at the carboxyl terminus are alanine at position 436, lysine at position 437, and at position 438 methionine in the case of the fructosyl amino acid oxidase derived from *Aspergillus nidulans*, 3 amino acid residues at the carboxyl terminus are alanine at position 436, lysine at position 437, and methionine at position 438 in the case of the fructosyl peptide oxidase derived from *Emericella nidulans*, 3 amino acid residues at the carboxyl terminus are alanine at position 439, lysine at position 440, and leucine at position 441 in the case of the fructosyl amino acid oxidase derived from *Ulocladium* sp., and 3 amino acid residues at the carboxyl terminus are alanine at position 435, lysine at position 436, and leucine at position 437 in the case of the fructosyl amino acid oxidase derived from *Penicillium janthinellum*.

(Production of the Amadoriase of the Present Invention)

In order to produce the amadoriase of the present invention using a strain having the capability to produce such amadoriase obtained as described above, although the strain may be cultured by a conventional solid culture method, liquid culture is preferably adopted where possible.

Examples of media to culture the aforementioned strains include media prepared by adding one or more inorganic salts selected from among, for example, sodium chloride, monopotassium phosphate, dipotassium phosphate, magnesium sulfate, magnesium chloride, ferric chloride, ferric sulfate, and manganese sulfate, to one or more nitrogen sources, such as a yeast extract, tryptone, peptone, a meat extract, a corn steep liquor, and a leaching solution of soybean or wheat bran, and further adding saccharine materials, vitamins, and the like thereto, where necessary.

It is appropriate to adjust the initial pH of the media to 7 to 9.

Culture can be performed under any conditions. For example, culture can be performed at 20° C. to 42° C., preferably at about 30° C. for 4 to 24 hours, and more preferably at about 30° C. for 8 to 16 hours, by, for example, aeration spinner submerged culture, shake culture, or stationary culture.

Following the completion of culture, amadoriases may be collected from the culture products with conventional enzyme collecting means. For example, a strain may be subjected to ultrasonic disintegration treatment or grinding treatment by a conventional method, the enzyme may be extracted using a lytic enzyme such as lysozyme, or bacteriolysis may be performed via shaking or still standing in the presence of toluene to excrete the enzyme from the microorganism body. The solution is filtered or centrifuged to remove the solid content, and nucleic acid is removed with the aid of streptomycin sulfate, protamine sulfate, or manganese sulfate, according to need. Ammonium sulfate, alcohol, or acetone is added to the solution, so as to fractionate the solution, and sediments are then collected to obtain the crude enzymes of the amadoriases.

A purified amadoriase enzyme preparation can be obtained from the crude enzyme of the aforementioned amadoriase by a method appropriately selected from among: gel filtration methods using Sephadex, Superdex, or Ultrogel; adsorption-elution methods using ion exchange carriers; electrophoretic methods using polyacrylamide gels, etc.; adsorption-elution methods using hydroxyapatite; sedimentation methods such as sucrose density-gradient centrifugation; affinity chromatography methods; and fractionation methods using a molecular sieve membrane, a hollow-fiber membrane, etc. Alternatively, the aforementioned methods can adequately be performed in combination, so as to obtain a purified amadoriase enzyme preparation. Thus, the amadoriase of interest having enhanced dehydrogenase activity can be obtained.

Amadoriases contained in the kit according to the present invention can be naturally-occurring amadoriases derived from the genus *Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium,* or *Arthrobacter* or variants thereof. Such variants comprise one or more amino acid substitutions at positions corresponding to amino acids selected from the group consisting of cysteine at position 280, phenylalanine at position 267, phenylalanine at position 269, aspartic acid at position 54, and tyrosine at position 241 in the amino acid sequence as shown in SEQ ID NO: 1. A person skilled in the art can readily determine whether or not a certain type of amadoriase or a variant thereof can be used for the kit according to the present invention (i.e., whether or not such amadoriase has dehydrogenase activity of interest) by, for example, the test method described below.

(Enhanced Dehydrogenase Activity of the Amadoriase According to the Present Invention)

The amadoriase according to the present invention obtained by the means as described above has a lowered oxidase activity and/or an enhanced dehydrogenase activity compared with the amadoriase prior to modification as a result of mutation of its amino acid sequence via genetic modification or other means. More specifically, the ratio of "oxidase activity" to "dehydrogenase activity" is lower than that before modification. The term "oxidase activity" refers to an activity that transfers an electron to an oxygen molecule when oxidizing the substrate. The term "dehydrogenase activity" refers to an activity that transfers a hydride ($H^-$) to an electron acceptor when oxidizing the substrate.

Low oxidase activity is desirable in order to reduce influence of oxygen when measuring glycated hemoglobin using a sensor. On the other hand, from the perspective of reactivity with the substrate, high dehydrogenase activity is desirable. That is, a low OX/DH ratio (i.e., a ratio of oxidase activity (OX) to dehydrogenase activity (DH)) of the amadoriase is preferable and a low oxidase activity and high dehydrogenase activity (DH) of the amadoriase is preferable for the measurement of glycated hemoglobin using electron mediators. For the convenience of description, properties of an amadoriase may be described in terms of DH/OX indicating the ratio of dehydrogenase activity to oxidase activity or OX/DH indicating the ratio of oxidase activity to dehydrogenase activity herein. In one embodiment, the modified amadoriase of the present invention has an enhanced dehydrogenase activity compared with that before modification. In one embodiment, the modified amadoriase of the present invention has a lowered oxidase activity compared with that before modification. In one embodiment, the modified amadoriase of the present invention has a low ratio of oxidase activity to dehydrogenase activity (a low OX/DH ratio) compared with that before modification; that is, a high DH/OX ratio. In one embodiment, the modified amadoriase of the present invention has an enhanced dehydrogenase activity and a lowered oxidase activity, compared with those before modification. Specifically, the modified amadoriase according to the present invention preferably has a DH/OX ratio, indicating the ratio of dehydrogenase activity to oxidase activity, of 1.3 times or greater, 2 times or greater, 3 times or greater, 4 times or greater, 5 times or greater, 10 times or greater, 20 times or greater, 30 times or greater, 40 times or greater, 50 times or greater, 100 times or greater, 200 times or greater, 300 times or greater, 400 times or greater, or 450 times or greater than that before modification (i.e., 1.0 times). Further, the modified amadoriase according to the present invention preferably has a OX/DH ratio, indicating the ratio of oxidase activity to dehydrogenase activity, of less than 90%, 80%, 75%, 50%, 40%, 30%, 20%, 10%, 5%, 2%, 1%, 0.5%, or 0.2% compared to the OX/DH ratio before modification (100%).

The ratio of oxidase activity to dehydrogenase activity can be measured under any conditions using conventional methods of amadoriase activity measurement and the results can be compared with those before modification. For example, the oxidase activity measured at pH 7.0 with the addition of 1 mM of a certain type of glycated substrate, such as αFV, can be divided by the dehydrogenase activity measured with the addition of 1 mM of said glycated substrate, so as to determine the ratio. By this the ratio of oxidase activity to dehydrogenase activity can be computed, and the computed ratios before modification and after modification may be compared.

(High-Throughput Screening)

An amadoriase can further be subjected to high-throughput screening, so as to obtain a functional amadoriase variant. For example, a library of a transformant or transductant comprising the transgenic amadoriase gene may be prepared and the resulting library may then be subjected to high-throughput screening using a microtiter plate. Alternatively, the library may be subjected to ultrahigh-throughput screening based on droplet microfluidics. For example, a combinatorial library of mutant genes encoding variants can be constructed and a large population of mutant amadoriases can be subjected to screening by means of phage display (e.g., Chem. Rev., 105 (11): 4056-72, 2005), yeast display (e.g., Comb. Chem. High Throughput Screen., 2008; 11(2): 127-34), or bacterial display (e.g., Curr. Opin. Struct. Biol., 17: 474-80, 2007). A reference may be made to Agresti et al, "Ultrahigh-throughput screening in drop-based microfluidics for directed evolution," Proceedings of the National Academy of Sciences, 107 (9): 4004-4009, Mar, 2010. The description thereof concerning the technique for ultrahigh-throughput screening, which may be employed for screening of an amadoriase variant is incorporated herein by reference. For example, a library can be constructed by error-prone PCR. Alternatively, a mutation may be introduced into a target, which is a position described herein or position corresponding thereto, via saturation mutagenesis, so as to construct a library. Adequate cells, such as electrocompetent EBY-100 cells, can be transformed using a library and approximately 10' variants can be obtained. Yeast cells transformed with the library can then be subjected to cell sorting. A polydimethoxylsiloxane (PDMS) microfluidic device prepared via standard soft-lithography may be used. Monodisperse droplets can be prepared using a flow-focusing device. The prepared droplets separately comprising variants can be applied to an adequate sorting device. Cells can be selected based on dehydrogenase activity. Mutagenesis and selection may be repeated a plurality of times.

(Method for Measuring Amadoriase Activity)

Activity of an amadoriase comprises oxidase activity and dehydrogenase activity, and such activities can be measured via various techniques. An exemplary method for measuring amadoriase activity employed in the present invention is described below.

(Method for Measuring Oxidase Activity of Amadoriase)

Examples of primary methods for measuring oxidase activity of an amadoriase according to the present invention include a method in which the amount of hydrogen peroxide generated upon an enzyme reaction is measured and a method in which the amount of oxygen consumed by an enzyme reaction is measured. An example of a method for measuring the amount of hydrogen peroxide is described below.

For measurement of the oxidase activity of the amadoriase of the present invention, unless indicated otherwise, fructosyl valine is used as the substrate. In one embodiment, regarding enzyme titer, the amount of enzyme capable of generating 1 μmol of hydrogen peroxide per minute can be defined as 1 U, when measurement is carried out using fructosyl valine as the substrate. A glycated amino acid, such as fructosyl valine, and a glycated peptide, such as fructosyl-valyl-histidine, can be synthesized and purified using the method of Sakaue et al. (JP 2001-95598 A). It should be noted that the description above is merely provided for convenience of description of the method of measurement and that substrate specificity of the amadoriase used in the present invention is not limited to fructosyl valine.

A: Preparation of Reagents (1) Reagent 1: POD-4-AA Solution

Peroxidase (4.0 kU, manufactured by Kikkoman Corporation) and 100 mg of 4-aminoantipyrine (manufactured by Tokyo Chemical Industry Co., Ltd.) are dissolved in a 0.1 M potassium phosphate buffer (pH 7.0), and the volume of the solution is fixed to 1 liter.

(2) Reagent 2: TOOS Solution

TOOS (500 mg, N-ethyl-N-(2-hydroxy-3-sulfopropyl)-m-toluidine sodium, manufactured by Dojindo Laboratories) is dissolved in ion-exchange water, and the volume of the solution is fixed to 100 ml.

(3) Reagent 3: Substrate Solution (30 mM; Final Concentration: 1 mM)

Fructosyl valine (83 mg) is dissolved in ion-exchange water, and the volume of the solution is fixed to 10 ml.

B: Method for Measurement

Reagent 1 (2.7 ml), 100 μl of Reagent 2, and 100 μl of Reagent 3 are mixed, and the mixture is preliminarily heated at 37° C. for 5 minutes. Subsequently, 100 μl of the enzyme solution is added, the resultant is thoroughly mixed, and the absorbance at 555 nm is measured using a spectrophotometer (U-3010, manufactured by Hitachi High-Technologies). The measurement value is the change in absorbance per minute at 555 nm from 1 minute later to 3 minutes later after the initiation of measurement. A control solution is prepared in the manner as described, with the proviso that 100 μl of ion-exchange water is added instead of 100 μl of Reagent 3. The number of micromoles of hydrogen peroxide generated per minute at 37° C. is calculated using the equation shown below in terms of the unit of activity (U) in the enzyme solution.

$$\text{Activity (U/ml)} = \{(\Delta As - \Delta A0) \times 3.0 \times df\}/(39.2 \times 0.5 \times 0.1)$$

$\Delta As$: the change in absorbance of the reaction solution per minute $\Delta A0$: the change in absorbance of the control solution per minute 39.2: the millimole absorbance index of the quinoneimine dye generated by the reaction ($mM^{-1} \cdot cm^{-1}$)

0.5: the number of moles of the quinoneimine dye generated by 1 mol of hydrogen peroxide df: the dilution factor (Method for Measurement of Dehydrogenase Activity of Amadoriase)

Examples of major methods for measurement of dehydrogenase activity of an amadoriase according to the present invention include methods in which an electron mediator other than oxygen is used as the electron acceptor and the amount of oxidized electron mediator consumed is measured as well as methods in which the amount of a formazan dye generated by enzyme reaction is measured. An example of a method in which the amount of a formazan dye generated is measured is described below.

For measurement of the dehydrogenase activity of the amadoriase of the present invention, unless indicated otherwise, fructosyl valine is used as the substrate. Regarding the enzyme titer, the amount of enzyme capable of generating 1 μmol of a formazan dye per minute is defined as 1 U, when measurement is carried out using fructosyl valine as the substrate.

C: Preparation of Reagents (4) Reagent 4: WST-3 Solution

WST-3 (700 mg, 2-(4-iodophenyl)-3-(2,4-dinitrophenyl)-5-(2,4-disulfophenyl)-2H-tetrazolium, monosodium salt, manufactured by Dojindo Laboratories) is dissolved in ion-exchange water (pH 7.0), and the volume of the solution is fixed to 100 ml.

(5) Reagent 5: Methoxy PMS (mPMS) Solution mPMS (50 mg, 1-methoxy-5-methylphenazinium methylsulfate, manufactured by Dojindo Laboratories) is dissolved in ion-exchange water, and the volume of the solution is fixed to 10 ml.

D: Method for Measurement

Reagent 4 (150 μl), Reagent 5 (9 μl), and an enzyme solution (25 μl) are mixed into 541 μl of 95 mM potassium phosphate buffer (pH 7.0), and the mixture is preliminarily heated at 37° C. for 5 minutes. Subsequently, 25 μl of Reagent 3 is added, the resultant is thoroughly mixed, and the absorbance at 433 nm is then measured using a spectrophotometer (U-3010, manufactured by Hitachi High-Technologies) to determine the change in absorbance per minute at 433 nm from 1 minute later to 2 minutes later after the initiation of measurement. A control solution is prepared in the manner as described above, with the proviso that 25 μl of ion-exchange water is added instead of 25 μl of Reagent 3. The number of micromoles of the formazan dye of WST-3 generated per minute at 37° C. is calculated using the equation shown below in terms of the unit of activity (U) in the enzyme solution.

$$\text{Activity (U/ml)} = \{(\Delta As - \Delta A0) \times 0.75 \times df\}/(31 \times 0.025)$$

$\Delta As$: the change in absorbance of the reaction solution per minute $\Delta A0$: the change in absorbance of the control solution per minute 31: the millimole absorbance index of the formazan dye generated by the reaction ($mM^{-1} \cdot cm^{-1}$)

df: the dilution factor (Reagent Kit and Sensor for Measurement)

In one embodiment, the present invention provides a kit for measurement of HbA1c and an apparatus for measurement of HbA1c comprising the amadoriase according to the present invention having an enhanced dehydrogenase activity. This kit or apparatus may optionally comprise an electron mediator.

In one embodiment, the present invention provides an enzyme electrode comprising an amadoriase according to the present invention with an enhanced dehydrogenase activity fixed thereto. According to an embodiment, the amadoriase according to the present invention with an enhanced dehydrogenase activity may be applied, adsorbed, or fixed onto the enzyme electrode. According to another embodiment, an electron mediator may also be applied, adsorbed, or fixed onto the electrode. Examples of electrodes that can be used include carbon electrodes and metal electrodes made of platinum, gold, silver, nickel, and palladium. Examples of materials constituting carbon electrodes include pyrolytic graphite carbon (PG), glassy carbon (GC), carbon paste, and plastic formed carbon (PFC). The measurement system may be a two-electrode system or a three-electrode system. For example, an enzyme can be fixed onto a working electrode. Examples of reference electrodes include standard hydrogen electrodes, reversible hydrogen electrodes, silver-silver chloride electrodes (Ag/AgCl), palladium-hydrogen electrodes, and saturated calomel electrodes. From the perspective of stability and reproducibility, Ag/AgCl is preferable.

An enzyme can be fixed onto an electrode via crosslinking, coating with the use of a dialysis membrane, embedding into a polymeric matrix, using a photocrosslinkable polymer, using an electroconductive polymer, using an oxidation-reduction polymer, or via other means. Alternatively, an enzyme may be fixed into a polymer or adsorbed and fixed onto an electrode together with an electron mediator. These techniques may be adopted in combination.

The amadoriase according to the present invention can be used for various types of electrochemical measurement techniques using, for example, a potentiostat or galvanostat. Examples of electrochemical measurement techniques include various techniques, such as amperometry, potentiometry, and coulometry. For example, a current generated upon oxidation of the reduced mediator by an applied voltage can be measured via amperometry, so as to determine the concentration of the glycated substrate in the sample. While an applied voltage varies depending on the conditions of a mediator or an apparatus, for example, it can be −1000 to +1000 mV (v.s., Ag/AgCl).

Glycated substrate (e.g., αFVH) concentration can be measured in the manner as described below. For example, a buffer is introduced into a temperature-controlled cell and the temperature is maintained at a constant level. Examples of mediators that can be used include potassium ferricyanide and phenazine methosulfate. As a working electrode, an electrode comprising the modified amadoriase of the present invention fixed thereon is used, and a counter electrode (e.g., a platinum electrode) and reference electrode (e.g., an Ag/AgCl electrode) are used. A certain level of voltage is applied to a carbon electrode, a sample comprising a glycated substrate (e.g., αFVH) is added after the current is stabilized, and an increased current is then measured. In accordance with a calibration curve prepared from glycated substrate (e.g., αFVH) solutions at standard concentrations, the concentration of the glycated substrate (e.g., αFVH) in the sample can be calculated.

Further, in order to reduce the amount of a solution necessary for measurement, a printed electrode can be used. In such case, an electrode is preferably formed on an insulated substrate. Specifically, an electrode is preferably formed on a substrate by means of photolithography or printing techniques, such as screen printing, gravure printing, or flexography. Examples of materials constituting insulated substrates include silicon, glass, ceramics, polyvinyl chloride, polyethylene, polypropyrene, and polyester. Use of materials exhibiting high tolerance against various solvents or chemicals is more preferable.

In one embodiment the present invention provides a sensor comprising said enzyme electrode.

In another embodiment, the concentration of the amadori compound in a sample can be determined by measuring a current generated upon an enzyme reaction using the enzyme electrode according to the present invention. For example, an enzyme electrode is used as a working electrode, and it is used together with a counter electrode and a reference electrode. A counter electrode can, for example, be a platinum electrode, and a reference electrode can, for example, be an Ag/AgCl electrode. While maintaining the temperature at a constant level, electrodes are introduced into a buffer containing a mediator. A voltage is applied to the working electrode, a sample is added thereto, and a change in the current is then measured.

Mediators used for the method, the kit, the apparatus, and the sensor for measurement according to the present invention (also referred to as an "artificial electron mediator," an "artificial electron acceptor," or an "electron mediator") are not limited, provided that such mediators are capable of receiving electrons from the amadoriase according to the present invention with an enhanced dehydrogenase activity. Examples of mediators include, but are not limited to, quinones, phenazines, viologens, cytochromes, phenoxazines, phenothiazines, ferricyanides such as potassium ferricyanide, ferredoxins, ferrocenes, osmium complexes, and derivatives thereof, and examples of phenazine compounds include, but are not limited to, PMS and methoxy PMS.

In one embodiment, the modified amadoriase according the present invention has enhanced dehydrogenase activity. In one embodiment, the modified amadoriase of the present invention has lowered oxidase activity. In one embodiment, the modified amadoriase of the present invention has a lowered ratio of oxidase activity/dehydrogenase activity (OX/DH). In one embodiment, the modified amadoriase of the present invention has enhanced dehydrogenase activity and lowered oxidase activity. The enzyme reaction catalyzed by such modified amadoriase according to the present invention is not influenced by oxygen, not substantially influenced by oxygen, or it is less likely to be influenced by oxygen. The modified amadoriase according to the present invention can be used for the same applications (same use) as those of conventional amadoriases. Further, the amadoriase according to the present invention can be used for measurement of the concentration of the glycated substrate in a sample, and this can be utilized, for example, for diagnosis of diabetes. The amadoriase according to the present invention can also be used as an enzyme electrode. This can be utilized in various types of electrochemical measurement techniques. The amadoriase according to the present invention can further be used as an enzyme sensor. Furthermore, the amadoriase according to the present invention can be used for a kit for measuring a diabetes marker. It should be noted that the applications described above are examples and that the use of the modified amadoriase according to the present invention are not limited thereto.

Example 1

(Mutation that Enhance Dehydrogenase Activity)
(1) Preparation of DNA of Recombinant Plasmid pKK223-3-CFP-T7

A strain of E. coli JM109 comprising the recombinant plasmid comprising the CFP-T7 gene (SEQ ID NO: 2) (pKK223-3-CFP-T7) (WO 2007/125779) was inoculated into 2.5 ml of LB-amp media (1% (w/v) bactotrypton, 0.5% (w/v) peptone, 0.5% (w/v) NaCl, and 50 μg/ml ampicillin) and shake culture was carried out at 37° C. for 20 hours to obtain a culture product.

The culture product was centrifuged at 7,000×g for 5 minutes to collect the cells. Subsequently, the recombinant plasmid pKK223-3-CFP-T7 was extracted and purified therefrom using QIAGEN tip-100 (manufactured by QIA- GEN), and 2.5 µl of DNA of the recombinant plasmid pKK223-3-CFP-T7 was obtained.

(2) Site-Directed Modification Procedure of DNA of Recombinant Plasmid pKK223-3-CFP-T7

PCR was carried out under conditions described below using DNA of the recombinant plasmid pKK223-3-CFP-T7 as the template, synthetic oligonucleotides of SEQ ID NOs: 14 and 15, and KOD-Plus- (Toyobo Co., Ltd.).

That is, 5 µl of 10× KOD-Plus-buffer, 5 µl of a dNTPs mixture in which each dNTP was adjusted at 2 mM, 2 µl of a 25 mM MgSO$_4$ solution, 50 ng of DNA of pKK223-3-CFP-T7 as the template, 15 pmol each of the synthetic oligonucleotides, and 1 unit of KOD-Plus were mixed, and sterilized water was added thereto in order to bring the total amount of the solution to 50 µl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 30 times.

A part of the reaction solution was subjected to electrophoresis on 1.0% agarose gel, and specific amplification of a DNA of about 6,000 bp was confirmed. The DNA obtained in such a manner was treated with a restriction enzyme DpnI (manufactured by New England Biolabs), the remaining template DNA was cleaved, strains of *E. coli* JM109 were transformed, and the transformants were then spread on LB-amp agar media. The grown colonies were inoculated into LB-amp media and shake-cultured therein, and plasmid DNA was isolated in the same manner as in (1) above. The nucleotide sequence of the DNA encoding the amadoriase in the plasmid was determined using a multi-capillary DNA analysis system (Applied Biosystems 3130xl Genetic Analyzer; manufactured by Life Technologies). Thus, the recombinant plasmid encoding the modified amadoriase resulting from substitution of cysteine at position 280 with glutamine in the amino acid sequence as shown in SEQ ID NO: 1 was obtained (pKK223-3-CFP-T7-280Q).

In order to substitute cysteine at position 280 with serine in the amino acid sequence as shown in SEQ ID NO: 1, in the same manner as described above, PCR was carried out under the same conditions as described above using DNA of the recombinant plasmid pKK223-3-CFP-T7 as the template, synthetic oligonucleotides of SEQ ID NOs: 15 and 16, and KOD-Plus- (Toyobo Co., Ltd.), strains of *E. coli* JM109 were transformed, and nucleotide sequence of the DNA encoding the amadoriase in the plasmid DNA harbored by the grown colonies was determined. As a result, the recombinant plasmid encoding the modified amadoriase resulting from substitution of cysteine at position 280 with serine in the amino acid sequence as shown in SEQ ID NO: 1 was obtained (pKK223-3-CFP-T7-280S).

The recombinant plasmid encoding the modified amadoriase resulting from substitution of cysteine at position 280 with aspartic acid in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 15 and 17 (pKK223-3-CFP-T7-280D.

The recombinant plasmid encoding the modified amadoriase resulting from substitution of cysteine at position 280 with glutamic acid in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 15 and 18 (pKK223-3-CFP-T7-280E).

The recombinant plasmid encoding the modified amadoriase resulting from substitution of cysteine at position 280 with methionine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 15 and 19 (pKK223-3-CFP-T7-280M).

The recombinant plasmid encoding the modified amadoriase resulting from substitution of cysteine at position 280 with lysine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 15 and 20 (pKK223-3-CFP-T7-280K).

The recombinant plasmid encoding the modified amadoriase resulting from substitution of cysteine at position 280 with arginine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 15 and 21 (pKK223-3-CFP-T7-280R).

The recombinant plasmid encoding the modified amadoriase resulting from substitution of cysteine at position 280 with valine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 15 and 22 (pKK223-3-CFP-T7-280V).

The recombinant plasmid encoding the modified amadoriase resulting from substitution of cysteine at position 280 with asparagine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 15 and 23 (pKK223-3-CFP-T7-280N).

The recombinant plasmid encoding the modified amadoriase resulting from substitution of phenylalanine at position 267 with tyrosine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 24 and 25 (pKK223-3-CFP-T7-267Y).

The recombinant plasmid encoding the modified amadoriase resulting from substitution of phenylalanine at position 269 with tyrosine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 26 and 27 (pKK223-3-CFP-T7-269Y).

The recombinant plasmid encoding the modified amadoriase resulting from substitution of aspartic acid at position 54 with asparagine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 28 and 29 (pKK223-3-CFP-T7-54N).

The recombinant plasmid encoding the modified amadoriase resulting from substitution of aspartic acid at position 54 with alanine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 29 and 30 (pKK223-3-CFP-T7-54A).

The recombinant plasmid encoding the modified amadoriase resulting from substitution of tyrosine at position 241 with glutamic acid in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 31 and 32 (pKK223-3-CFP-T7-241E).

The recombinant plasmid encoding the modified amadoriase resulting from substitution of tyrosine at position 241 with glutamine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 32 and 33 (pKK223-3-CFP-T7-241Q).

The recombinant plasmid encoding the modified amadoriase resulting from substitution of tyrosine at position 241 with lysine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 32 and 34 (pKK223-3-CFP-T7-241K).

The recombinant plasmid encoding the modified amadoriase resulting from substitution of cysteine at position 280 with histidine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 35 and 36 (pKK223-3-CFP-T7-280H).

The recombinant plasmid encoding the modified amadoriase resulting from substitution of cysteine at position 280 with threonine in the amino acid sequence as shown in SEQ ID NO: 1 was obtained using DNA of the recombinant plasmid pKK223-3-CFP-T7 as the template in the same manner as described above except for the use of synthetic oligonucleotides of SEQ ID NOs: 35 and 37 (pKK223-3-CFP-T7-280T).

PCR was carried out using DNA of the recombinant plasmid pKK223-3-CFP-T7 as the template in the same manner as described above except for the use of synthetic oligonucleotides of SEQ ID NOs: 38 and 39, the resultant was treated with DpnI, 2 µl of the DpnI-treated DNA, 5 µl of Ligation high ver.2 (manufactured by Toyobo Co., Ltd.), and 1 µl of 5 U/µl T4 polynucleotide kinase were added, the total amount of the mixture was adjusted to 15 µl with sterilized water, and the mixture was subjected to the reaction at 16° C. for 1 hour. Thereafter, strains of E. coli JM109 were transformed using the reaction solution, and the E. coli JM109 strain carrying the recombinant plasmid encoding the modified amadoriase resulting from substitution of phenylalanine at position 267 with leucine in the amino acid sequence as shown in SEQ ID NO: 1 was obtained (pKK223-3-CFP-T7-267L).

PCR was carried out using DNA of the recombinant plasmid pKK223-3-CFP-T7 as the template in the same manner as described above except for the use of synthetic oligonucleotides of SEQ ID NOs: 38 and 40, the resultant was treated with DpnI, 2 µl of the DpnI-treated DNA, 5 µl of Ligation high ver.2 (manufactured by Toyobo Co., Ltd.), and 1 µl of 5 U/µl T4 polynucleotide kinase were added, the total amount of the mixture was adjusted to 15 µl with sterilized water, and the mixture was subjected to the reaction at 16° C. for 1 hour. Thereafter, strains of E. coli JM109 were transformed using the reaction solution, and the recombinant plasmid encoding the modified amadoriase resulting from substitution of phenylalanine at position 267 with methionine in the amino acid sequence as shown in SEQ ID NO: 1 was obtained (pKK223-3-CFP-T7-267M).

PCR was carried out using DNA of the recombinant plasmid pKK223-3-CFP-T7 as the template in the same manner as described above except for the use of synthetic oligonucleotides of SEQ ID NOs: 41 and 42, the resultant was treated with DpnI, 2 µl of the DpnI-treated DNA, 5 µl of Ligation high ver.2 (manufactured by Toyobo Co., Ltd.), and 1 µl of 5 U/µl T4 polynucleotide kinase were added, the total amount of the mixture was adjusted to 15 µl with sterilized water, and the mixture was subjected to the reaction at 16° C. for 1 hour. Thereafter, strains of E. coli JM109 were transformed using the reaction solution, and the recombinant plasmid encoding the modified amadoriase resulting from substitution of phenylalanine at position 269 with leucine in the amino acid sequence as shown in SEQ ID NO: 1 was obtained (pKK223-3-CFP-T7-269L).

PCR was carried out using DNA of the recombinant plasmid pKK223-3-CFP-T7 as the template in the same manner as described above except for the use of synthetic oligonucleotides of SEQ ID NOs: 41 and 43, the resultant was treated with DpnI, 2 µl of the DpnI-treated DNA, 5 µl of Ligation high ver.2 (manufactured by Toyobo Co., Ltd.), and 1 µl of 5 U/µl T4 polynucleotide kinase were added, the total amount of the mixture was adjusted to 15 µl with sterilized water, and the mixture was subjected to the reaction at 16° C. for 1 hour. Thereafter, strains of E. coli JM109 were transformed using the reaction solution, and the recombinant plasmid encoding the modified amadoriase resulting from substitution of phenylalanine at position 269 with methionine in the amino acid sequence as shown in SEQ ID NO: 1 was obtained (pKK223-3-CFP-T7-269M).

PCR, transformation, and nucleotide sequencing were carried out in the same manner as described above.

(3) Production of Various Types of Modified Amadoriases

Strains of E. coli JM109 carrying the recombinant plasmids obtained in the manner described above were cultured in 3 ml of LB-amp media supplemented with 0.1 mM IPTG at 30° C. for 16 hours. Thereafter, the resulting cultured strains were washed with a 0.01 M phosphate buffer (pH 7.0), the washed strains were ultrasonically disrupted, and the resultants were centrifuged at 15,000 rpm for 10 minutes to prepare 1.5 ml each of crude enzyme solution.

(4) Evaluation of Oxidase Activity and Dehydrogenase Activity of Various Types of Modified Amadoriases The various types of crude enzyme solutions thus prepared were designated as samples, and oxidase activity and dehydrogenase activity of various types of modified amadoriases were evaluated using the method for measurement of oxidase activity and the method for measurement of dehydrogenase activity described above. Examples of the results are shown in Table 1.

In Table 1, "CFP-T7" indicates an amadoriase derived from the strain E. coli JM109 (pKK223-3-CFP-T7). In this example, CFP-T7, which is an amadoriase derived from the strain E. coli JM109 (pKK223-3-CFP-T7), is employed as the original enzyme for mutation. Therefore, descriptions concerning "Amino acid mutations" in the table do not include various points of mutations that have already been introduced into CFP-T7. In the table, oxidase activity (%)

and dehydrogenase activity (%) are expressed in percentage terms relative to the oxidase activity (U/ml) of the original enzyme CFP-T7 designated to be 100. In the table, "OX/DH (%)" is expressed in percentage terms relative to the OX/DH ratio of the original enzyme CFP-T7 designated to be 100.

TABLE 1

| Plasmid | Amino acid mutation | Oligo-nucleotide No. | Oxidase activity (%) | Dehydrogenase activity (%) | OX/DH | OX/DH (%) |
|---|---|---|---|---|---|---|
| pKK223-3-CFP-T7 | None | None | 100.00 | 3.84 | 26.0 | 100.00 |
| pKK223-3-CFP-T7-280Q | C280Q | 14, 15 | 0.69 | 12.05 | 0.057 | 0.22 |
| pKK223-3-CFP-T7-280S | C280S | 15, 16 | 50.00 | 16.88 | 3.00 | 11.54 |
| pKK223-3-CFP-T7-280D | C280D | 15, 17 | 0.19 | 0.07 | 2.80 | 10.77 |
| pKK223-3-CFP-T7-280E | C280E | 15, 18 | 0.82 | 0.57 | 1.40 | 5.38 |
| pKK223-3-CFP-T7-280M | C280M | 15, 19 | 1.96 | 1.25 | 1.60 | 6.15 |
| pKK223-3-CFP-T7-280K | C280K | 15, 20 | 0.16 | 0.07 | 2.40 | 9.23 |
| pKK223-3-CFP-T7-280R | C280R | 15, 21 | 0.19 | 0.05 | 3.70 | 14.23 |
| pKK223-3-CFP-T7-280V | C280V | 15, 22 | 11.52 | 0.36 | 32.0 | 123.08 |
| pKK223-3-CFP-T7-280N | C280N | 15, 23 | 0.65 | 0.21 | 3.20 | 12.31 |
| pKK223-3-CFP-T7-280H | C280H | 41, 42 | 0.42 | 1.25 | 0.33 | 1.27 |
| pKK223-3-CFP-T7-280T | C280T | 41, 43 | 27.41 | 2.5 | 11.0 | 42.31 |
| pKK223-3-CFP-T7-267Y | F267Y | 24, 25 | 20.54 | 7.95 | 2.60 | 10.00 |
| pKK223-3-CFP-T7-267L | F267L | 35, 36 | 4.02 | 9.64 | 0.41 | 1.58 |
| pKK223-3-CFP-T7-267M | F267M | 35, 37 | 5.54 | 18.13 | 0.31 | 1.19 |
| pKK223-3-CFP-T7-269Y | F269Y | 26, 27 | 15.54 | 5.54 | 2.80 | 10.77 |
| pKK223-3-CFP-T7-269L | F269L | 38, 39 | 9.38 | 25.54 | 0.37 | 1.42 |
| pKK223-3-CFP-T7-269M | F269M | 38, 40 | 20.98 | 24.20 | 0.87 | 3.35 |
| pKK223-3-CFP-T7-54N | D54N | 28, 29 | 0.93 | 0.59 | 1.60 | 6.15 |
| pKK223-3-CFP-T7-54A | D54A | 29, 30 | 2.14 | 1.61 | 1.30 | 5.00 |
| pKK223-3-CFP-T7-241E | Y241E | 31, 32 | 3.84 | 0.64 | 6.00 | 23.08 |
| pKK223-3-CFP-T7-241Q | Y241Q | 32, 33 | 76.52 | 7.95 | 9.60 | 36.92 |
| pKK223-3-CFP-T7-241K | Y241K | 32, 34 | 205.36 | 10.89 | 19.0 | 73.08 |

As shown in Table 1, CFP-T7 was found to exhibit a ratio of oxidase activity to dehydrogenase activity (OX/DH) of 26.0 under the conditions of the present example and it was found to be strongly influenced by oxygen. In contrast, among the 22 mutants obtained via site-directed mutagenesis, all mutants except for mutant C280V; that is, the amadoriases resulting from substitution of cysteine at position 280 of CFP-T7 with glutamine, serine, aspartic acid, glutamic acid, methionine, lysine, arginine, asparagine, histidine, or threonine, phenylalanine at position 267 with tyrosine, leucine, or methionine, phenylalanine at position 269 with tyrosine, leucine, or methionine, aspartic acid at position 54 with asparagine or alanine, and tyrosine at position 241 with glutamic acid, glutamine, or lysine, exhibited an improvement in OX/DH of 19 or less. For significant mutants, the OX/DH was improved to 10 or less, and for further significant mutants, the OX/DH was improved to 3.7 or less. In particular, C280Q, C280S, F267Y, F267L, F267M, F269Y, F269L, F269M, and Y241Q (mutants) were found to have enhanced dehydrogenase activity compared with CFP-T7; and yet, oxidase activity thereof was found to be lowered (decreased). Accordingly, it was demonstrated that these points of mutations improve the dehydrogenase activity of the amadoriase.

As a result of substitution of position 280 with glutamine, serine, or asparagine, satisfactory results were obtained. It was thus considered that similar results could be obtained via substitution of position 280 with threonine, which is also a polar amino acid, and this was confirmed as described above.

As a result of substitution of position 280 with aspartic acid, glutamic acid, lysine, or arginine, satisfactory results were obtained. It was thus considered that similar results could be obtained via substitution of position 280 with histidine, which is also a charged amino acid, and this was confirmed as described above.

As a result of substitution of position 280 with methionine, satisfactory results were obtained. It was thus considered that similar results could be obtained via substitution of position 280 with phenylalanine, tyrosine, tryptophane, or proline, which is also a bulky amino acid.

As a result of substitution of position 267 and 269 with tyrosine, methionine, or leucine, satisfactory results were obtained. It was thus considered that similar results could be obtained via substitution of position 267 and 269 with isoleucine, tryptophane, valine, or alanine, which are also hydrophobic amino acid residues.

As a result of substitution of position 54 with asparagine, satisfactory results were obtained. It was thus considered that similar results could be obtained via substitution of position 54 with glutamine, which is also a polar amino acid residue. Further, satisfactory results were obtained as a result of substitution of position 54 with a polar amino acid. It was thus considered that similar results could be obtained as a result of substitution with histidine, which is a charged amino acid.

As a result of substitution of position 54 with alanine, also, satisfactory results were obtained. It was thus considered that similar results could be obtained as a result of substitution with glycine or valine, which are also non-polar amino acids with relatively short side chain.

As a result of substitution of position 241 with glutamine, satisfactory results were obtained. It was thus considered that similar results could be obtained via substitution with asparagine, which is also a polar amino acid residue.

As a result of substitution of position 241 with lysine or glutamic acid, also, satisfactory results were obtained. It was thus considered that similar results could be obtained via substitution with arginine, aspartic acid, or histidine, which are also charged amino acid residues.

Example 2

(Purification of CFP-T7 and CFP-T7-280Q)

The crude enzyme solutions prepared using the crude enzymes CFP-T7 and CFP-T7-280Q obtained in Example 1 were allowed to adsorb to 4 ml of Q Sepharose Fast Flow resin (manufactured by GE Healthcare) equilibrated with a 20 mM potassium phosphate buffer (pH 8.0), the resin was washed with 80 ml of the same buffer, the proteins that were adsorbed to the resin was eluted with the aid of a 20 mM potassium phosphate buffer (pH 8.0) containing 100 mM NaCl, and fractions exhibiting amadoriase activity were then collected.

The fractions exhibiting amadoriase activity were concentrated using Amicon Ultra-15 (NMWL: 30K, manufactured by Millipore). Thereafter, the resultant was applied to the HiLoad 26/60 Superdex 200 pg column (manufactured by GE Healthcare) equilibrated with a 20 mM potassium phosphate buffer (pH 7.0) containing 150 mM NaCl so as to carry out elution with the same buffer, fractions exhibiting amadoriase activity were collected, and purified samples of wild-type and modified amadoriases were then obtained. The purified samples were analyzed via SDS-PAGE and confirmed that the fractions had been purified to the extent that a single band was obtained.

(Evaluation of Oxidase Activity and Dehydrogenase Activity)

The purified enzymes CFP-T7 and CFP-T7-280Q obtained in the manner described above were evaluated in terms of oxidase activity and dehydrogenase activity. Evaluation was carried out using the methods for measurement of oxidase activity and dehydrogenase activity described in Example 1, except that 30 mM αFVH was used as the substrate and the enzyme activity relative to 1 absorbance unit of the enzyme used for measurement at 280 nm was determined (U/A280). Examples of the results are shown in Table 2. In the table, "OX/DH (%)" indicates a percentage relative to the OX/DH ratio of the original enzyme CFP-T7 designated to be 100.

TABLE 2

| Plasmid | Oxidase activity (U/A280) | Dehydrogenase activity (U/A280) | OX/DH | OX/DH (%) |
|---|---|---|---|---|
| pKK223-3-CFP-T7 | 6.24 | 0.63 | 9.90 | 100.00 |
| pKK223-3-CFP-T7-C280Q | 0.03 | 0.84 | 0.037 | 0.37 |

As shown in Table 2, the ratio of oxidase activity to dehydrogenase activity of CFP-T7 (OX/DH) is 9.9 under the conditions employed in this example, and CFP-T7 would be strongly affected by oxygen when measuring αFVH. In contrast, CFP-T7-280Q exhibited OX/DH of 0.037, which was remarkably improved. The C280Q variant according to the present invention exhibited oxidase activity lowered by 208 times (fold), and dehydrogenase activity improved by 1.3 times. That is, αFVH can be measured without being substantially influenced by oxygen.

[Example 3] (Site-Directed Modification of Various Amadoriases)

(Preparation of DNA of Recombinant Plasmid pUTE100K'-EFP-T5)

SEQ ID NO: 44 shows the amino acid sequence of a modified enzyme of fructosyl peptide oxidase derived from Eupenicillium terrenum (EFP-T5), and it can be prepared by E. coli strains carrying the recombinant plasmid pUTE100K'-EFP-T5 into which the gene (SEQ ID NO: 45) encoding the amino acid sequence as shown in SEQ ID NO: 44 has been inserted (see WO 2007/125779 A). The E. coli JM109 strain carrying pUTE100K'-EFP-T5 was cultured using the method described in "Example 1 (1) Preparation of DNA of recombinant plasmid pK223-3-CFP-T7 DNA," and pUTE100K'-EFP-T5 was extracted and purified.

(Introduction of Point Mutation into the Gene of Fructosyl Peptide Oxidase Derived from Eupenicillium terrenum)

In order to introduce a mutation to improve (alter) the ratio of oxidase activity to dehydrogenase activity into EFP-T5, in the same manner as in Example 1, PCR was carried out using the recombinant plasmid pUTE100K'-EFP-T5 as the template, synthetic oligonucleotides as shown in SEQ ID NOs: 46 and 47, and KOD-Plus- (manufactured by TOYOBO CO., LTD.), strains of E. coli JM109 were transformed, and the nucleotide sequence of DNA encoding the EFP-T5 variant in the plasmid DNA carried on the grown colonies was determined. As a result, the recombinant plasmid encoding the EFP-T5 gene comprising the amino acid sequence derived from the amino acid sequence as shown in SEQ ID NO: 44 by substitution of cysteine at position 280 with glutamine was obtained (pUTE100K'-EFP-T5-280Q).

The recombinant plasmid encoding the modified amadoriase resulting from substitution of cysteine at position 280 with serine in the amino acid sequence as shown in SEQ ID NO: 44 was obtained using the recombinant plasmid pUTE100K'-EFP-T5 as the template in the same manner as described above except for the use of synthetic oligonucleotides of SEQ ID NOs: 35 and 36 (pUTE100K'-EFP-T5-280S).

(Preparation of DNA of Recombinant Plasmid pET22b-PnFX)

SEQ ID NO: 9 shows the amino acid sequence of fructosyl peptide oxidase derived from Phaeosphaeria nodorum (PnFX), and it can be prepared by E. coli strains carrying the recombinant plasmid pET22b-PnFX into which the gene (SEQ ID NO: 49) encoding the amino acid sequence as shown in SEQ ID NO: 9 has been inserted (see WO 2013/162035 A). The E. coli JM109 strain carrying pET22b-PnFX was cultured using the method described in "Example 1 (1) Preparation of DNA of recombinant plasmid pK223-3-CFP-T7 DNA," and pET22b-PnFX was extracted and purified.

(Introduction of Point Mutation into Gene of Fructosyl Peptide Oxidase Derived from Phaeosphaeria nodorum)

In order to introduce a mutation to improve (alter) the ratio of oxidase activity to dehydrogenase activity into PnFX, in the same manner as in Example 1, PCR was carried out using the recombinant plasmid pET22b-PnFX prepared in the manner as described above as the template, synthetic oligonucleotides of SEQ ID NOs: 50 and 51, and KOD-Plus- (manufactured by TOYOBO CO., LTD.), strains of E. coli JM109 were transformed, and the nucleotide sequence of DNA encoding the PnFX variant in the plasmid DNA carried on the grown colonies was determined. As a result, a recombinant plasmid encoding the PnFX gene comprising an amino acid sequence derived from the amino acid sequence as shown in SEQ ID NO: 9 by substitution of cysteine at position 276 with glutamine was obtained (pET22b-PnFX-276Q).

Subsequently, in the same manner as described above, a recombinant plasmid encoding the PnFX gene comprising an amino acid sequence derived from the amino acid sequence as shown in SEQ ID NO: 9 by substitution of cysteine at position 276 with serine was obtained using pET22b-PnFX as the template and synthetic oligonucleotides of SEQ ID NOs: 50 and 52 (pET22b-PnFX-276S).

Strains of *E. coli* BL21 (DE3) were transformed under the same conditions as in Example 1 to obtain strains of *E. coli* BL21 (DE3) (pET22b-PnFX-276Q) and strains of *E. coli* BL21 (DE3) (pET22b-PnFX-276S).
(Preparation of DNA of Recombinant Plasmid pET22b-AnFX)

SEQ ID NO: 53 shows the amino acid sequence of fructosyl amino acid oxidase derived from *Aspergillus nidulans* (AnFX) resulting from substitution of serine at position 59 with glycine in order to impart fructosyl peptide oxidase activity, and it can be prepared by *E. coli* strains carrying the recombinant plasmid pET22b-AnFX into which the gene (SEQ ID NO: 54) encoding the amino acid sequence as shown in SEQ ID NO: 53 has been inserted (see WO 2012/018094 A). The *E. coli* JM109 strain carrying pET22b-AnFX was cultured in accordance with the method described in "Example 1 (1) Preparation of DNA of recombinant plasmid pK223-3-CFP-T7 DNA," and pET22b-AnFX was extracted and purified.
(Introduction of Point Mutation into Gene of Fructosyl Peptide Oxidase Derived from *Aspergillus nidulans*)

In order to introduce a mutation to improve (alter) the ratio of oxidase activity to dehydrogenase activity into AnFX, in the same manner as in Example 1, PCR was carried out using the recombinant plasmid pET22b-AnFX as the template, synthetic oligonucleotides of SEQ ID NOs: 55 and 56, and KOD-Plus- (manufactured by TOYOBO CO., LTD.), strains of *E. coli* JM109 were transformed, and the nucleotide sequence of DNA encoding the AnFX variant in the plasmid DNA carried on the grown colonies was determined. As a result, a recombinant plasmid encoding the AnFX gene comprising an amino acid sequence derived from the amino acid sequence as shown in SEQ ID NO: 53 by substitution of cysteine at position 280 with glutamine was obtained (pET22b-AnFX-280Q).

Subsequently, in the same manner as described above, a recombinant plasmid encoding the AnFX gene comprising an amino acid sequence derived from the amino acid sequence as shown in SEQ ID NO: 53 by substitution of cysteine at position 280 with serine was obtained using pET22b-AnFX as the template and synthetic oligonucleotides of SEQ ID NOs: 55 and 57 (pET22b-AnFX-280S).

Strains of *E. coli* BL21 (DE3) were transformed under the same conditions as in Example 1 to obtain strains of *E. coli* BL21 (DE3) (pET22b-AnFX-280Q) and strains of *E. coli* BL21 (DE3) (pET22b-AnFX-280S).
(Preparation of DNA of Recombinant Plasmid pKK223-3-CcFX)

SEQ ID NO: 6 shows the amino acid sequence of ketoamine oxidase derived from *Curvularia clavata* (CcFX) (WO WO2004/104203). It can be prepared by *E. coli* strains carrying the recombinant plasmid pKK223-3-CcFX into which the gene (SEQ ID NO: 58) encoding the amino acid sequence as shown in SEQ ID NO: 6 has been inserted (see WO 2015/020200). The *E. coli* JM109 strain carrying pKK223-3-CcFX was cultured in accordance with the method described in "Example 1 (1) Preparation of DNA of recombinant plasmid pK223-3-CFP-T7 DNA," and pKK223-3-CcFX was extracted and purified.
(Introduction of Point Mutation into Gene of Ketoamine Oxidase Derived from *Curvularia clavata*)

In order to introduce a mutation to improve (alter) the ratio of oxidase activity to dehydrogenase activity into CcFX, in the same manner as in Example 1, PCR was carried out using the recombinant plasmid pKK223-3-CcFX as the template, synthetic oligonucleotides of SEQ ID NOs: 59 and 60, and KOD-Plus- (manufactured by TOYOBO CO., LTD.), strains of *E. coli* JM109 were transformed, and the nucleotide sequence of DNA encoding the CcFX variant in the plasmid DNA carried on the grown colonies was determined. As a result, the recombinant plasmid encoding the CcFX gene comprising the amino acid sequence derived from the amino acid sequence as shown in SEQ ID NO: 6 by substitution of cysteine at position 278 with glutamine was obtained (pKK223-3-CcFX-278Q).

Subsequently, in the same manner as described above, a recombinant plasmid encoding the CcFX gene comprising an amino acid sequence derived from the amino acid sequence as shown in SEQ ID NO: 6 by substitution of cysteine at position 278 with serine was obtained using pKK223-3-CcFX as the template and synthetic oligonucleotides of SEQ ID NOs: 59 and 61 (pKK223-3-CcFX-278S).

Subsequently, in the same manner as described above, PCR was carried out using pKK223-3-CcFX as the template and synthetic oligonucleotides of SEQ ID NOs: 62 and 63, the resultant was treated with DpnI, 2 μl of the DpnI-treated DNA, 5 μl of Ligation high ver.2 (manufactured by Toyobo Co., Ltd.), and 1 μl of 5 U/μl T4 polynucleotide kinase were added, the total amount of the mixture was adjusted to 15 μl with sterilized water, and the mixture was subjected to the reaction at 16° C. for 1 hour. Thereafter, strains of *E. coli* JM109 were transformed using the reaction solution, and the recombinant plasmid encoding the CcFX gene comprising the amino acid sequence derived from the amino acid sequence as shown in SEQ ID NO: 6 by substitution of phenylalanine at position 265 with leucine was obtained (pKK223-3-CcFX-265L).

Subsequently, in the same manner as described above, PCR was carried out using pKK223-3-CcFX as the template and synthetic oligonucleotides of SEQ ID NOs: 62 and 64, the resultant was treated with DpnI, 2 μl of the DpnI-treated DNA, 5 μl of Ligation high ver.2 (manufactured by Toyobo Co., Ltd.), and 1 μl of 5 U/μl T4 polynucleotide kinase were added, the total amount of the mixture was adjusted to 15 μl with sterilized water, and the mixture was subjected to the reaction at 16° C. for 1 hour. Thereafter, strains of *E. coli* JM109 were transformed using the reaction solution, and the recombinant plasmid encoding the CcFX gene comprising the amino acid sequence derived from the amino acid sequence as shown in SEQ ID NO: 6 by substitution of phenylalanine at position 265 with methionine was obtained (pKK223-3-CcFX-265M).

Subsequently, in the same manner as described above, PCR was carried out using pKK223-3-CcFX as the template and synthetic oligonucleotides of SEQ ID NOs: 65 and 66, the resultant was treated with DpnI, 2 μl of the DpnI-treated DNA, 5 μl of Ligation high ver.2 (manufactured by Toyobo Co., Ltd.), and 1 μl of 5 U/μl T4 polynucleotide kinase were added, the total amount of the mixture was adjusted to 15 μl with sterilized water, and the mixture was subjected to the reaction at 16° C. for 1 hour. Thereafter, strains of *E. coli* JM109 were transformed using the reaction solution, and the recombinant plasmid encoding the CcFX gene comprising the amino acid sequence derived from the amino acid sequence as shown in SEQ ID NO: 6 by substitution of phenylalanine at position 267 with leucine was obtained (pKK223-3-CcFX-267L).

Subsequently, in the same manner as described above, PCR was carried out using pKK223-3-CcFX as the template and synthetic oligonucleotides of SEQ ID NOs: 65 and 82, the resultant was treated with DpnI, 2 μl of the DpnI-treated DNA, 5 μl of Ligation high ver.2 (manufactured by Toyobo Co., Ltd.), and 1 μl of 5 U/μl T4 polynucleotide kinase were added, the total amount of the mixture was adjusted to 15 μl with sterilized water, and the mixture was subjected to the reaction at 16° C. for 1 hour. Thereafter, strains of E. coli JM109 were transformed using the reaction solution, and the recombinant plasmid encoding the CcFX gene comprising the amino acid sequence derived from the amino acid sequence as shown in SEQ ID NO: 6 by substitution of phenylalanine at position 267 with methionine was obtained (pKK223-3-CcFX-267M).

(Introduction of Point Mutation into Gene of Ketoamine Oxidase Derived from *Emericella nidulans*)

SEQ ID NO: 67 shows the amino acid sequence of glycated hexapeptide oxidase derived from *Emericella nidulans* (En42FX) (WO 2015/005258). The gene (SEQ ID NO: 68) encoding the amino acid sequence as shown in SEQ ID NO: 67 was obtained by a conventional technique of total synthesis of cDNA via PCR of a gene fragment (including the termination codon TAA). In order to express the gene comprising the sequence as shown in SEQ ID NO: 69 in *E. coli*, subsequently, the process described below was carried out. First, a fragment comprising the gene comprising the sequence as shown in SEQ ID NO: 68 was amplified using synthetic oligonucleotides of SEQ ID NOs: 69 and 70 in accordance with the users' manual of the In-Fusion HD Cloning Kit (manufactured by Clontech Laboratories, Inc.). At the same time, a fragment containing pET22b was amplified using synthetic oligonucleotides of SEQ ID NOs: 71 and 72. Subsequently, a fragment comprising the gene comprising the sequence as shown in SEQ ID NO: 68 was subcloned into a fragment comprising pET22b via the in-fusion reaction, the recombinant plasmid was obtained (pET22b-En42FX), strains of E. coli JM109 were transformed under the same conditions as described above, and strains of E. coli JM109 were obtained (pET22b-En42FX).

In order to introduce a mutation to improve (alter) the ratio of oxidase activity to dehydrogenase activity into En42FX, in the same manner as in Example 1, PCR was carried out using the recombinant plasmid pET22b-En42FX as the template, synthetic oligonucleotides of SEQ ID NOs: 73 and 74, and KOD-Plus- (manufactured by TOYOBO CO., LTD.), 2 μl of the DpnI-treated DNA, 5 μl of Ligation high ver.2 (manufactured by Toyobo Co., Ltd.), and 1 μl of 5 U/μl T4 polynucleotide kinase were added, the total amount of the mixture was adjusted to 15 μl with sterilized water, and the mixture was subjected to the reaction at 16° C. for 1 hour. Thereafter, strains of E. coli JM109 were transformed using the reaction solution, and the nucleotide sequence of DNA encoding the En42FX variant in the plasmid DNA carried on the grown colonies was determined. As a result, a recombinant plasmid encoding the En42FX gene comprising an amino acid sequence derived from the amino acid sequence as shown in SEQ ID NO: 67 by substitution of cysteine at position 280 with glutamine was obtained (pET22b-En42FX-280Q).

Subsequently, in the same manner as described above, a recombinant plasmid encoding the En42FX gene comprising an amino acid sequence derived from the amino acid sequence as shown in SEQ ID NO: 67 by substitution of cysteine at position 280 with serine was obtained using pET22b-En42FX as the template and synthetic oligonucleotides of SEQ ID NOs: 73 and 75 (pET22b-En42FX-280S).

Subsequently, in the same manner as described above, a recombinant plasmid encoding the En42FX gene comprising an amino acid sequence derived from the amino acid sequence as shown in SEQ ID NO: 67 by substitution of phenylalanine at position 267 with leucine was obtained using pET22b-En42FX as the template and synthetic oligonucleotides of SEQ ID NOs: 76 and 77 (pET22b-En42FX-267L).

Subsequently, in the same manner as described above, a recombinant plasmid encoding the En42FX gene comprising an amino acid sequence derived from the amino acid sequence as shown in SEQ ID NO: 67 by substitution of phenylalanine at position 267 with methionine was obtained using pET22b-En42FX as the template and synthetic oligonucleotides of SEQ ID NOs: 76 and 78 (pET22b-En42FX-267M).

Subsequently, in the same manner as described above, a recombinant plasmid encoding the En42FX gene comprising an amino acid sequence derived from the amino acid sequence as shown in SEQ ID NO: 67 by substitution of isoleucine at position 269 with leucine was obtained using pET22b-En42FX as the template and synthetic oligonucleotides of SEQ ID NOs: 79 and 80 (pET22b-En42FX-269L).

Subsequently, in the same manner as described above, a recombinant plasmid encoding the En42FX gene comprising an amino acid sequence derived from the amino acid sequence as shown in SEQ ID NO: 67 by substitution of isoleucine at position 269 with methionine was obtained using pET22b-En42FX as the template and synthetic oligonucleotides of SEQ ID NOs: 79 and 81 (pET22b-En42FX-269M).

Strains of E. coli BL21 (DE3) were transformed under the same conditions as in Example 1 to obtain strains of E. coli BL21 (DE3) (pET22b-En42FX-280Q), strains of E. coli BL21 (DE3) (pET22b-En42FX-280S), strains of E. coli BL21 (DE3) (pET22b-En42FX-267L), strains of E. coli BL21 (DE3) (pET22b-En42FX-267M), strains of E. coli BL21 (DE3) (pET22b-En42FX-269L), and strains of E. coli BL21 (DE3) (pET22b-En42FX-269M).

(Production of Various Types of Modified Amadoriases)

Strains of E. coli JM109 or strains of E. coli BL21 (DE3) carrying the recombinant plasmids obtained in the manner described above were cultured in 3 ml of LB-amp media supplemented with 0.1 mM IPTG at 25° C. for 16 hours. Thereafter, the resulting cultured strains were washed with a 0.01 M phosphate buffer (pH 7.0), the washed strains were ultrasonically disintegrated, and the resultants were centrifuged at 15,000 rpm for 10 minutes to prepare 1.5 ml each of crude enzyme solutions.

(Evaluation of Oxidase Activity and Dehydrogenase Activity of Various Types of Modified Amadoriases)

The crude enzyme solutions thus prepared were designated as samples, and oxidase activity and dehydrogenase activity of various types of modified amadoriases were evaluated in accordance with the method for measurement of oxidase activity and the method for measurement of dehydrogenase activity described above. The results are shown in Tables 3 to 7. In Tables 4, 5, and 6, oxidase activity (%) and dehydrogenase activity (%) are expressed in percentage terms relative to the oxidase activity (U/ml) of the wild-type enzymes or the original enzyme designated to be 100. In Tables 3 to 7, "OX/DH (%)" is expressed in percentage terms relative to the OX/DH ratio of the wild-type enzyme or the original enzyme designated to be 100.

TABLE 3

| Plasmid | Amino acid mutation | Oligonucleotide No. | OX/DH | OX/DH (%) |
|---|---|---|---|---|
| UTE100K'-EFP-T5 | None | None | 1.44 | 100.00 |
| UTE100K'-EFP-T5-280Q | C280Q | 46, 47 | 0.24 | 16.67 |
| UTE100K'-EFP-T5-280S | C280S | 46, 48 | 0.91 | 63.19 |

TABLE 4

| Plasmid | Amino acid mutation | Oligo-nucleotide No. | Oxidase activity (%) | Dehydro-genase activity (%) | OX/DH | OX/DH (%) |
|---|---|---|---|---|---|---|
| pET22b-PnFX | None | None | 100 | 46.01 | 2.17 | 100.00 |
| pET22b-PnFX-276Q | C276Q | 50, 51 | 0.46 | 12.32 | 0.037 | 1.71 |
| pET22b-PnFX-276S | C276S | 50, 52 | 35.06 | 52.69 | 0.67 | 30.88 |

TABLE 5

| Plasmid | Amino acid mutation | Oligo-nucleotide No. | Oxidase activity (%) | Dehydro-genase activity (%) | OX/DH | OX/DH (%) |
|---|---|---|---|---|---|---|
| pET22b-AnFX | None | None | 100 | 6.67 | 15.0 | 100.00 |
| pET22b-AnFX-280Q | C280Q | 55, 56 | 4.35 | 13.95 | 0.31 | 2.07 |
| pET22b-AnFX-280S | C280S | 55, 57 | 38.36 | 10.16 | 3.77 | 25.13 |

TABLE 6

| Plasmid | Amino acid mutation | Oligonucleotide No. | Oxidase activity (%) | Dehydrogenase activity (%) | OX/DH | OX/DH (%) |
|---|---|---|---|---|---|---|
| pKK223-3-CcFX | None | None | 100.00 | 5.32 | 18.8 | 100.00 |
| pKK223-3-CcFX-278Q | C278Q | 59, 60 | 0.47 | 9.90 | 0.047 | 0.25 |
| pKK223-3-CcFX-278S | C278S | 59, 61 | 26.85 | 9.21 | 2.91 | 15.48 |
| pKK223-3-CcFX-265L | F265L | 62, 63 | 3.30 | 9.26 | 0.36 | 1.91 |
| pKK223-3-CcFX-265M | F265M | 62, 64 | 40.92 | 178.31 | 0.23 | 1.22 |
| pKK223-3-CcFX-267L | F267L | 65, 66 | 8.39 | 17.41 | 0.48 | 2.55 |
| pKK223-3-CcFX-267M | F267M | 65, 82 | 74.21 | 128.62 | 0.58 | 3.09 |

TABLE 7

| Plasmid | Amino acid mutation | Oligonucleotide No. | OX/DH | OX/DH (%) |
|---|---|---|---|---|
| pET22b-EnFX42 | None | None | 0.81 | 100.00 |
| pET22b-EnFX42-280Q | C280Q | 73, 74 | 0.38 | 46.91 |
| pET22b-EnFX42-280S | C280S | 73, 75 | 0.24 | 29.63 |
| pET22b-EnFX42-267L | F267L | 76, 77 | 0.77 | 95.1 |
| pET22b-EnFX42-267M | F267M | 76, 78 | 0.045 | 5.56 |
| pET22b-EnFX42-269L | I269L | 79, 80 | 0.48 | 59.3 |
| pET22b-EnFX42-269M | I269M | 79, 81 | 0.57 | 70.4 |

As shown in Tables 3 to 7, all of the modified amadoriases, in which the amino acid at the position corresponding to cysteine at position 280 in the amadoriase sequence as shown in SEQ ID NO: 1 was substituted with glutamine or serine, exhibited improved OX/DH values compared to those of wild-type enzymes prior to the amino acid substitutions described above. This indicates that the effects of substitution resulting in improved OX/DH values can be exerted regardless of the origin of the amadoriase.

Example 4

(Quantification of αFVH Using a Printed Electrode)

With the purified enzymes of CFP-T7 and CFP-T7-280Q obtained in Example 2, αFVH was quantified using printed electrodes. That is, 15 μl of a solution comprising mPMS (final concentration: 3.75 mM or 7.5 mM), phosphate buffer (final concentration: about 10 mM; pH: 7.0), and 50 mU purified enzyme solution dissolved therein relative to 1 mM αFVH was applied onto the DEP Chip electrode on which a carbon working electrode and a silver-silver chloride reference electrode is printed (i.e., DEP-EP-PP, round, with ring and dam; manufactured by BioDevice Technology, Ltd.). Thereafter, the DEP chip was attached to the compact potentiostat BDT miniSTAT 100 (manufactured by BioDevice Technology, Ltd.) using the DEP-Chip-exclusive connector. A voltage of +200 mV (v.s. Ag/AgCl) was applied, 5 μl each of the αFVH solutions at a given concentration was applied onto the electrodes, the reaction was allowed to occur, and the current level was measured 120 seconds later. FIG. 3 shows the results of plotting the current responses at relevant concentration of αFVH subjected to the reaction using CFP-T7, and FIG. 4 shows the results of plotting the current responses at relevant concentration of αFVH subjected to the reaction using CFP-T7-280Q.

Figures 1, 4:
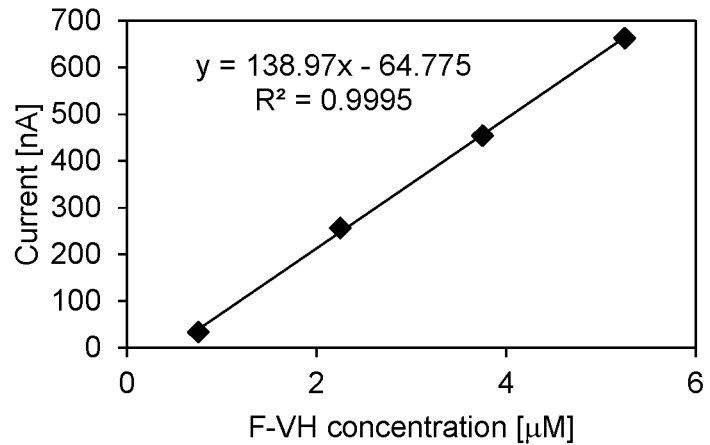
Figures 2, 4:
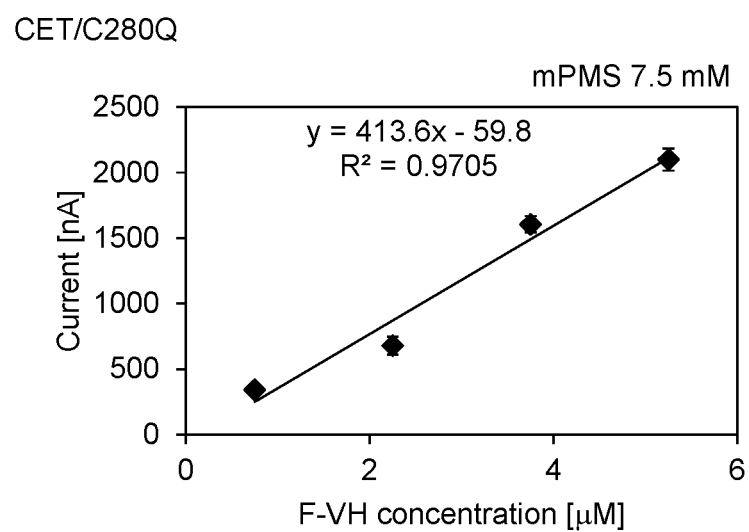

As shown in FIGS. 3-1 and 4-1, CFP-T7-280Q was found to be capable of quantification of αFVH with higher accuracy than CFP-T7 in the reaction system supplemented with 3.75 mM mPMS. Further, as shown in FIGS. 3-2 and 4-2, CFP-T7-280Q was found to be capable of quantification of αFVH with higher accuracy than CFP-T7 in the reaction system supplemented with 7.5 mM mPMS.

All publications, patents, and patent applications cited herein are incorporated herein by reference in their entirety.

Brief Description of Sequences

SEQ ID NO: 1: the amino acid sequence of CFP-T7
SEQ ID NO: 2: the gene sequence of CFP-T7
SEQ ID NO: 3: the amadoriase derived from *Eupenicillium terrenum*
SEQ ID NO: 4: the ketoamine oxidase derived from *Pyrenochaeta* sp.
SEQ ID NO: 5: the ketoamine oxidase derived from *Arthrinium* sp.
SEQ ID NO: 6: the ketoamine oxidase derived from *Curvularia clavata*
SEQ ID NO: 7: the ketoamine oxidase derived from *Neocosmospora vasinfecta*
SEQ ID NO: 8: the fructosyl amino acid oxidase derived from *Cryptococcus neoformans*

SEQ ID NO: 9: the fructosyl peptide oxidase derived from *Phaeosphaeria nodorum*
SEQ ID NO: 10: the fructosyl amino acid oxidase derived from *Aspergillus nidulans*
SEQ ID NO: 11: the fructosyl peptide oxidase derived from *Emericella nidulans*
SEQ ID NO: 12: the fructosyl amino acid oxidase derived from *Ulocladium* sp.
SEQ ID NO: 13: the fructosyl amino acid oxidase derived from *Penicillium janthinellum*
SEQ ID NO: 14: C280Q-Fw
SEQ ID NO: 15: C280Q-Rv
SEQ ID NO: 16: C280S-Fw
SEQ ID NO: 17: C280D-Fw
SEQ ID NO: 18: C280E-Fw
SEQ ID NO: 19: C280M-Fw
SEQ ID NO: 20: C280K-Fw
SEQ ID NO: 21: C280R-Fw
SEQ ID NO: 22: C280V-Fw
SEQ ID NO: 23: C280N-Fw
SEQ ID NO: 24: F267Y-Fw
SEQ ID NO: 25: F267X-Rv
SEQ ID NO: 26: F269Y-Fw
SEQ ID NO: 27: F269X-Rv
SEQ ID NO: 28 D54N-Fw
SEQ ID NO: 29 D54X-Rv
SEQ ID NO: 30 D54A-Fw
SEQ ID NO: 31 Y241E-Fw
SEQ ID NO: 32 Y241X-Rv
SEQ ID NO: 33 Y241Q-Fw
SEQ ID NO: 34 Y241K-Fw
SEQ ID NO: 35: CFP-T7 C280X r
SEQ ID NO: 36: CFP-T7 C280H f
SEQ ID NO: 37: CFP-T7 C280T f
SEQ ID NO: 38: CFP-T7 F267X r
SEQ ID NO: 39: CFP-T7 F267L f
SEQ ID NO: 40: CFP-T7 F267M f
SEQ ID NO: 41: CFP-T7 F269X r
SEQ ID NO: 42: CFP-T7 F269L f
SEQ ID NO: 43: CFP-T7 F269M f
SEQ ID NO: 44: EFP-T5 protein
SEQ ID NO: 45: EFP-T5 gene
SEQ ID NO: 46: EFP C280X r
SEQ ID NO: 47: EFP C280Q f
SEQ ID NO: 48: EFP C280S f
SEQ ID NO: 49: PnFX gene
SEQ ID NO: 50: Pn C276X r
SEQ ID NO: 51: Pn C276Q f
SEQ ID NO: 52: Pn C276S r
SEQ ID NO: 53: AnFX protein
SEQ ID NO: 54: AnFX gene
SEQ ID NO: 55: An C280X r
SEQ ID NO: 56: An C280Q f
SEQ ID NO: 57: An C280S f
SEQ ID NO: 58: CcFX gene
SEQ ID NO: 59: Cc C278X r
SEQ ID NO: 60: Cc C278Q f
SEQ ID NO: 61: Cc C278S f
SEQ ID NO: 62: Cc F265X r
SEQ ID NO: 63: Cc F265L f
SEQ ID NO: 64: Cc F265M f
SEQ ID NO: 65: Cc F267X r
SEQ ID NO: 66: Cc F267L f
SEQ ID NO: 67: En42FX protein
SEQ ID NO: 68: En42FX gene
SEQ ID NO: 69: In-fusion En42X insert
SEQ ID NO: 70: In-fusion En42X insert
SEQ ID NO: 71: In-fusion pET22b vector
SEQ ID NO: 72: In-fusion pET22b vector
SEQ ID NO: 73: En C280X r
SEQ ID NO: 74: En C280Q f
SEQ ID NO: 75: En C280S f
SEQ ID NO: 76: En F267X r
SEQ ID NO: 77: En F267L f
SEQ ID NO: 78: En F267M f
SEQ ID NO: 79: En I269X r
SEQ ID NO: 80: En I269L f
SEQ ID NO: 81: En I269M f
SEQ ID NO: 82: Cc F267M f

The invention claimed is:

1. A modified amadoriase having oxidase activity and dehydrogenase activity, said modified amadoriase comprising an amino acid sequence having 92% or higher sequence identity with the amino acid sequence of SEQ ID NO: 1 over the full length and comprising, when aligned with the amino acid sequence of SEQ ID NO: 1, substitution of one or more amino acids at positions corresponding to positions selected from the group consisting of positions 280, 269, 54, and 241 of the amino acid sequence of SEQ ID NO: 1,
wherein:
(i) when said substitution is at the position corresponding to position 280 of SEQ ID NO: 1 the amino acid to substitute with is glutamine, serine, threonine, asparagine, aspartic acid, glutamic acid, lysine, arginine, histidine, methionine, proline, phenylalanine, tyrosine, or tryptophan;
(ii) when said substitution is at the position corresponding to position 269 of SEQ ID NO:1, the amino acid to substitute with is methionine, leucine, tyrosine, tryptophan, valine, or alanine;
(iii) when said substitution is at the position corresponding to position 54 of SEQ ID NO: 1, the amino acid to substitute with is asparagine, alanine, glutamine, histidine, glycine, or valine; and
(iv) when said substitution is at the position corresponding to position 241 of SEQ ID NO:1, the amino acid to substitute with is glutamine, lysine, glutamic acid, asparagine, arginine, aspartic acid, or histidine.

2. The modified amadoriase according to claim 1, further comprising an amino acid substitution at the position corresponding to position 267 of SEQ ID NO: 1, wherein the amino acid to substitute with is methionine, leucine, isoleucine, tryptophan, valine, or alanine.

3. The modified amadoriase according to claim 1, wherein the amino acid at the position corresponding to position 280 of the amino acid sequence of SEQ ID NO: 1 has been substituted with glutamine, serine, histidine, threonine, asparagine, aspartic acid, glutamic acid, lysine, arginine, or methionine;
the amino acid at the position corresponding to position 269 of the amino acid sequence of SEQ ID NO: 1 has been substituted with methionine, leucine, tyrosine, or tryptophan;
the amino acid at the position corresponding to position 54 of the amino acid sequence of SEQ ID NO: 1 has been substituted with asparagine or alanine; or
the amino acid at the position corresponding to position 241 of the amino acid sequence of SEQ ID NO: 1 has been substituted with glutamine, glutamic acid, or lysine.

4. The modified amadoriase according to claim 3, wherein the amino acid at the position corresponding to position 280 of the amino acid sequence of SEQ ID NO: 1 has been substituted with glutamine, serine, histidine, threonine, asparagine, aspartic acid, glutamic acid, lysine, arginine, or methionine;
the amino acid at the position corresponding to position 269 of the amino acid sequence of SEQ ID NO: 1 has been substituted with methionine, leucine, or tyrosine;
the amino acid at the position corresponding to position 54 of the amino acid sequence of SEQ ID NO: 1 has been substituted with asparagine or alanine; or the amino acid at the position corresponding to position 241 of the amino acid sequence of SEQ ID NO: 1 has been substituted with glutamine, glutamic acid, or lysine.

5. The modified amadoriase according to claim 3, wherein the amino acid at the position corresponding to position 280 of the amino acid sequence of SEQ ID NO: 1 has been substituted with glutamine or serine;

the amino acid at the position corresponding to position 269 of the amino acid sequence of SEQ ID NO: 1 has been substituted with methionine, leucine, or tyrosine; or the amino acid at the position corresponding to position 241 of the amino acid sequence of SEQ ID NO: 1 has been substituted with glutamine.

6. The modified amadoriase according to claim 3, wherein the amino acid at the position corresponding to position 280 of the amino acid sequence of SEQ ID NO: 1 has been substituted with glutamine or histidine; or the amino acid at the position corresponding to position 269 of the amino acid sequence of SEQ ID NO: 1 has been substituted with methionine or leucine.

7. The modified amadoriase according to claim 3, wherein the amino acid at the position corresponding to position 280 of the amino acid sequence of SEQ ID NO: 1 has been substituted with glutamine; or the amino acid at the position corresponding to position 269 of the amino acid sequence of SEQ ID NO: 1 has been substituted with methionine or leucine.

8. The modified amadoriase according to claim 1, wherein the amadoriase before modification is derived from the genus *Coniochaeta*.

9. A reagent kit for measurement of HbA1c comprising the modified amadoriase according to claim 1.

10. An enzyme electrode comprising the modified amadoriase according to claim 1.

11. An enzyme sensor comprising the enzyme electrode according to claim 10 as a working electrode.

12. A method for measuring HbA1c, the method comprising contacting the modified amadoriase of claim 1 with a sample comprising glycated hemoglobin and an electron mediator.

13. A method for measuring HbA1c, the method comprising contacting the enzyme electrode of claim 10 with a sample comprising glycated hemoglobin and an electron mediator.

14. A method for measuring HbA1c, the method comprising contacting the enzyme sensor of claim 11 with a sample comprising glycated hemoglobin and an electron mediator.

* * * * *

SEQUENCE LISTING

```
<160> NUMBER OF SEQ ID NOS: 82

<210> SEQ ID NO 1
<211> LENGTH: 437
<212> TYPE: PRT
<213> ORGANISM: Coniochaeta sp.

<400> SEQUENCE: 1

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
```

```
            100                 105                 110
Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
                180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
        210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
                260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
        290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 2
<211> LENGTH: 1314
<212> TYPE: DNA
<213> ORGANISM: Coniochaeta sp.

<400> SEQUENCE: 2
atgacgtcga atcgtgcaga tacaaggggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
```

```
atacgactgc gcaacaaggt ggacctgcaa atgagtctag aggctagaca gatgtggaag    240
gaggatgagt tattccagcc cttctttcac aataccggca gaatggactg cgaacacacg    300
cctgagggta tcgaggacct gaaaaagcag taccaggcac tgcacgatgc cggtgcgggt    360
ctggagaaga ctcatgcctg gttggacaac gaggatgaga tcttatccaa gatgccgttg    420
cttcaacgtg accaaataca aggatggaaa gcaatatgga gtcaagatgg cggctggtta    480
gctgcggcaa aggccatcaa tgcgatcgga cagttcttga agaacgtggt gtaaagttc     540 ggattcggcg cgctggatcc cttcaagcaa ccccttttcg acgatgaagg cacaacttgc    600
attggcgttg agacggcaga tggtaccaaa tattacgctg acaaggtggt cttagcagct    660
ggcgcatgga gcccaacccct ggtggacctg aagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc cgcttcaag gaacatcaac cctatggcgc cccatctccg    900
aaacggatat cagtaccacg atcgcacgcc aagcatccca cagacactta tccgacgca    960 tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca atggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa          1314
```

<210> SEQ ID NO 3
<211> LENGTH: 437
<212> TYPE: PRT
<213> ORGANISM: Eupenicillium terrenum

<400> SEQUENCE: 3

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

```
Gly Val Lys Phe Gly Phe Gly Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
            245                 250                 255

Val Pro Val Val Tyr Asp Gly Glu Tyr Gly Phe Phe Glu Pro Asn
        260                 265                 270

Glu Tyr Gly Val Ile Lys Val Cys Asp Glu Phe Pro Gly Phe Ser Arg
    275                 280                 285

Phe Lys Leu His Gln Pro Tyr Gly Ala Ala Ser Pro Lys Met Ile Ser
290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
            325                 330                 335

Lys Asp Lys Glu Leu Phe Asn Arg Thr Met Cys Trp Cys Thr Asp Thr
        340                 345                 350

Ala Asp Ala Asn Leu Leu Ile Cys Glu His Pro Lys Trp Lys Asn Phe
    355                 360                 365

Ile Leu Ala Thr Gly Asp Ser Gly His Ser Phe Lys Leu Leu Pro Asn
370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
            405                 410                 415

Arg Arg Gly Ala Pro Ala Lys Asp Leu Ala Glu Met Pro Gly Trp Lys
        420                 425                 430

His Asp Ala His Leu
        435

<210> SEQ ID NO 4
<211> LENGTH: 440
<212> TYPE: PRT
<213> ORGANISM: Pyrenochaeta sp.

<400> SEQUENCE: 4

Met Ala Ala Ser Arg Ala Lys Thr Thr Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Pro Ser Asn Ile Thr Val Leu Asp Thr Tyr Pro Ile Pro Ser Leu
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110
```

Thr Leu Leu Asp Ala Asn Ala Gly Leu Glu Glu Thr Asn Glu Trp Leu
            115                 120                 125

Asp Ser Glu Asp Glu Ile Leu Ala Arg Met Pro Leu Leu Ser Arg Glu
        130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Ala Gly Ser Phe Gln Gln Pro Leu
            180                 185                 190

Leu Ala Glu Gly Ile Cys Ile Gly Val Glu Thr Thr Asp Gly Thr Arg
            195                 200                 205

Tyr Tyr Ala Asp Lys Val Val Leu Ala Ala Gly Ala Trp Ser Pro Ala
        210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Phe Glu Pro Asn Glu His
            260                 265                 270

Gly Val Ile Lys Val Cys Asp Glu Phe Pro Gly Phe Thr Arg Phe Lys
            275                 280                 285

Lys His Gln Pro Phe Gly Ala Arg Ala Pro Lys Arg Ile Ser Val Pro
            290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
        355                 360                 365

Ala Thr Gly Asp Ser Gly His Ser Phe Lys Leu Leu Pro Asn Ile Gly
    370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
            420                 425                 430

Asp Glu Ser Pro Arg Ala Lys Leu
        435                 440

<210> SEQ ID NO 5
<211> LENGTH: 452
<212> TYPE: PRT
<213> ORGANISM: Arthrinium sp.

<400> SEQUENCE: 5

Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Ala Thr Asn Ile Thr Val Leu Asp Thr Tyr Pro Ile Pro Ser Ala

```
            35                  40                  45
Gln Ser Ala Gly Asn Asp Leu Asn Lys Ile Met Gly Ile Arg Leu Arg
 50                  55                  60

Asn Pro Val Asp Lys Gln Leu Ser Leu Glu Ala Gln Asp Met Trp Cys
 65                  70                  75                  80

His Asp Glu Leu Phe Lys Pro Tyr Phe His Asn Thr Gly Arg Met Asp
                 85                  90                  95

Cys Glu Gly Thr Glu Lys Gly Ile Ala Ala Leu Lys Gln Gln Tyr Gln
                100                 105                 110

Thr Leu Leu Asp Ala Asp Val Gly Leu Glu Lys Thr Thr Glu Trp Leu
                115                 120                 125

Asp Ser Glu Asp Ala Ile Leu Ala Lys Met Pro Leu Leu Glu Arg Asp
130                 135                 140

Gln Ile Lys Gly Trp Lys Ala Ile Phe Ser Gln Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Gly Ala Gly Ala Phe Lys Lys Pro Leu
                180                 185                 190

Phe Ala Pro Asp Gly Ser Thr Cys Ile Gly Val Glu Thr Val Asp Gly
                195                 200                 205

Thr Lys Tyr Tyr Gly Asp Lys Val Val Leu Ala Ala Gly Ala Trp Ser
210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
                260                 265                 270

Glu His Gly Val Ile Lys Val Cys Asp Glu Phe Pro Gly Phe Thr Arg
                275                 280                 285

Phe Leu Glu Gln His Gln Ser Tyr Gly Ala Pro Ala Pro Thr Arg Val
290                 295                 300

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
                325                 330                 335

Phe Gln Ser Lys Glu Leu Phe Asn Arg Ala Met Cys Trp Cys Thr Asp
                340                 345                 350

Thr Ala Asp Ala Ala Leu Leu Ile Cys Glu His Pro Arg Trp Arg Asn
                355                 360                 365

Phe Ile Leu Ala Thr Gly Asp Ser Gly His Ser Phe Lys Leu Leu Pro
                370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gln Gly Asp Ala Leu
                405                 410                 415

Lys Ser Arg Arg Ala Ala Pro Ala Lys Asp Leu Ala Asp Met Pro Gly
                420                 425                 430

Trp Asn His Asp Gly Asp Ser Gly Asn Ala Thr Ser Gly Thr Ser Ser
                435                 440                 445

Glu His Lys Leu
450
```

<210> SEQ ID NO 6
<211> LENGTH: 440
<212> TYPE: PRT
<213> ORGANISM: Curvularia clavata

<400> SEQUENCE: 6

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Asp Arg Glu
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Val
    210                 215                 220

Leu Val Asp Leu Glu Asp Gln Cys Val Ser Lys Ala Trp Val Tyr Ala
225                 230                 235                 240

His Ile Gln Leu Thr Pro Glu Glu Ala Glu Tyr Lys Asn Val Pro
                245                 250                 255

Val Val Tyr Asn Gly Asp Val Gly Phe Phe Phe Glu Pro Asp Glu His
            260                 265                 270

Gly Val Ile Lys Val Cys Asp Glu Phe Pro Gly Phe Thr Arg Phe Lys
        275                 280                 285

Gln His Gln Pro Tyr Gly Ala Lys Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
```

```
            370                 375                 380
Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
                420                 425                 430

Asp Asp Val Val Lys Ser Lys Leu
                435                 440

<210> SEQ ID NO 7
<211> LENGTH: 441
<212> TYPE: PRT
<213> ORGANISM: Neocosmospora vasinfecta

<400> SEQUENCE: 7

Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
                20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95

Cys Glu Ser Ser Ala Glu Gly Val Glu Gly Leu Arg Arg Glu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Ala Gly Ser Phe Lys Arg Pro Leu
            180                 185                 190

Phe Ala Asp Asp Gly Thr Thr Cys Ile Gly Val Glu Thr Val Asp Gly
            195                 200                 205

Thr Gln Tyr His Ala Asp Lys Val Val Leu Ala Ala Gly Ala Trp Ser
        210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Phe Glu Pro Asn
            260                 265                 270

Glu Asn Gly Val Ile Lys Val Cys Asp Glu Phe Pro Gly Phe Thr Arg
        275                 280                 285

Phe Lys Gln His Gln Pro Tyr Gly Ala Pro Ala Pro Lys Pro Val Ser
        290                 295                 300
```

```
Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
        355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
            435                 440

<210> SEQ ID NO 8
<211> LENGTH: 477
<212> TYPE: PRT
<213> ORGANISM: Cryptococcus neoformans

<400> SEQUENCE: 8

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240
```

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Glu Pro Asn
            260                 265                 270

Glu Lys Gly Val Ile Lys Val Cys Asp Glu Phe Pro Gly Phe Thr Arg
            275                 280                 285

Phe Lys Gln His Gln Pro Tyr Gly Ala Ser Ser Thr Lys His Ile Ser
            290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Ile Leu Pro Asn
            370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Met Asp Val Lys Asp Val Ala
            435                 440                 445

Val Ser Leu Ala Ser Val Lys Ile Gly Glu Asn Ile Gly Glu Lys Val
            450                 455                 460

Val Glu Asp Gly Ala Arg Val Gly Val Lys Val Leu Ala
465                 470                 475

<210> SEQ ID NO 9
<211> LENGTH: 437
<212> TYPE: PRT
<213> ORGANISM: Phaeosphaeria nodorum

<400> SEQUENCE: 9

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
            35                  40                  45

Gln Ser Ala Gly Asn Asp Leu Asn Lys Ile Met Gly Val Ser Leu Arg
50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
            85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
            115                 120                 125

Glu Asp Glu Ile Leu Lys Arg Met Pro Leu Leu Ser Arg Asp Gln Ile

```
            130                 135                 140
Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
                195                 200                 205

Ala Asp Lys Val Val Leu Ala Ala Gly Ala Trp Ser Pro Thr Leu Val
            210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Glu Pro Asn Glu His Gly Val
            260                 265                 270

Ile Lys Val Cys Asp Glu Phe Pro Gly Phe Thr Arg Phe Lys Met His
            275                 280                 285

Gln Pro Phe Gly Ala Lys Ala Pro Lys Arg Ile Ser Val Pro Arg Ser
        290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
            355                 360                 365

Gly Asp Ser Gly His Ser Phe Lys Leu Leu Pro Asn Ile Gly Lys His
        370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Ser
                405                 410                 415

Ala Pro Ala Lys Asp Leu Ala Asp Met Pro Gly Trp Asn His Asp Lys
            420                 425                 430

Pro Arg Ala Asn Leu
        435

<210> SEQ ID NO 10
<211> LENGTH: 438
<212> TYPE: PRT
<213> ORGANISM: Aspergillus nidulans

<400> SEQUENCE: 10

Met Thr Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Cys Pro Ile Pro Ser Ala Gln
            35                  40                  45

Ser Ala Gly Tyr Asp Leu Asn Lys Ile Met Ser Ile Arg Leu Arg Asn
        50                  55                  60
```

```
Lys Pro Asp Leu Gln Leu Ser Leu Glu Ala Leu Asp Met Trp Lys Asn
 65                  70                  75                  80

Asp Pro Leu Phe Lys Pro Phe Phe His Asn Val Gly Met Ile Asp Val
                 85                  90                  95

Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Gly Ala Trp Ser
210                 215                 220

Ser Thr Leu Val Asp Leu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Ala Pro Lys Pro Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 11
<211> LENGTH: 438
<212> TYPE: PRT
<213> ORGANISM: Emericella nidulans

<400> SEQUENCE: 11
```

```
Met Ala Pro Arg Ala Asn Thr Lys Ile Ile Val Val Gly Gly Gly
 1               5                  10                 15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Arg Leu Arg Asn
50                  55                  60

Lys Pro Asp Leu Gln Leu Tyr Leu Glu Ala Leu Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415
```

Ser Arg Arg Ala Ala Pro Ala Lys Asp Leu Ala Asp Met Pro Gly Trp
            420                 425                 430
Arg Asn Glu Ala Lys Met
            435

<210> SEQ ID NO 12
<211> LENGTH: 441
<212> TYPE: PRT
<213> ORGANISM: Ulocladium sp.

<400> SEQUENCE: 12

Met Ala Pro Asn Arg Ala Asn Ile Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Asp Gly Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Ala Gly Ser Phe Lys Gln Pro Leu
            180                 185                 190

Leu Ala Glu Gly Val Cys Val Gly Val Glu Thr Val Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
                245                 250                 255

Val Val Tyr Asn Gly Asp Val Gly Phe Phe Phe Glu Pro Asp Glu Tyr
            260                 265                 270

Gly Val Ile Lys Val Cys Asp Glu Phe Pro Gly Phe Thr Arg Phe Lys
        275                 280                 285

Gln His Gln Pro Phe Gly Ala Ser Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
                325                 330                 335

Lys Glu Val Phe Asn Arg His Leu Cys Trp Cys Thr Asp Thr Ala Asp
            340                 345                 350

```
Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
                405                 410                 415

Arg Ala Ala Arg Ala Lys Asp Leu Ala Asp Met Pro Gly Trp Asn His
                420                 425                 430

Asp Gly Glu Ala Pro Arg Ala Lys Leu
        435                 440

<210> SEQ ID NO 13
<211> LENGTH: 437
<212> TYPE: PRT
<213> ORGANISM: Penicillium janthinellum

<400> SEQUENCE: 13

Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
50                  55                  60

Asn Gly Pro Asp Leu Gln Leu Ser Leu Glu Ala Leu Asp Met Trp Lys
65                  70                  75                  80

Asn Asp Pro Leu Phe Lys Pro Phe His Asn Val Gly Met Leu Asp
                85                  90                  95

Cys Ser Ser Ser Gln Glu Gly Ile Ala Ser Leu Arg Arg Lys His Gln
                100                 105                 110

Asp Leu Ile Asp Ala Asn Ile Gly Leu Glu Lys Thr Asn Ile Trp Leu
            115                 120                 125

Glu Ser Glu Asp Asp Ile Leu Ala Lys Ala Pro His Phe Thr Arg Glu
130                 135                 140

Gln Ile Lys Gly Trp Lys Gly Leu Phe Cys Gly Asp Gly Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
        195                 200                 205

Thr Lys Tyr Phe Ala Asp Lys Val Val Leu Ala Ala Gly Ala Trp Ser
    210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Phe Glu Pro Asn
            260                 265                 270

Glu His Gly Val Ile Lys Val Cys Asp Glu Phe Pro Gly Phe Ser Arg
```

-continued

```
              275                 280                 285
Phe Lys Leu His Gln Pro Tyr Gly Ala Thr Ser Pro Lys Leu Ile Ser
    290                 295                 300
Val Pro Arg Ser His Ala Lys His Pro Thr Asp Thr Tyr Pro Asp Ser
305                 310                 315                 320
Ser Glu Glu Thr Ile Arg Lys Ala Ile Ala Arg Phe Met Pro Arg Phe
                325                 330                 335
Lys Asp Lys Glu Leu Phe Asn Arg Ser Met Cys Trp Cys Thr Asp Thr
            340                 345                 350
Ala Asp Ala Asn Leu Leu Ile Cys Glu His Pro Lys Trp Lys Asn Phe
        355                 360                 365
Ile Leu Ala Thr Gly Asp Ser Gly His Ser Phe Lys Val Leu Pro Asn
    370                 375                 380
Ile Gly Lys His Val Val Glu Leu Ile Glu Gly Arg Leu Pro Gln Asp
385                 390                 395                 400
Leu Ala Gly Ala Trp Arg Trp Arg Pro Gly Gly Asp Ala Leu Lys Ser
                405                 410                 415
Lys Arg Ser Ala Pro Ala Lys Asp Leu Ala Glu Met Pro Gly Trp Lys
            420                 425                 430
His Asp Ala Lys Leu
        435

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
gtaataaagg tgcaggacga attcccagga                                    30

<210> SEQ ID NO 15
<211> LENGTH: 27
<212> TYPE: DNA
<213> ORGANISM: Artificial
<220> FEATURE:
<223> OTHER INFORMATION: primer

<400> SEQUENCE: 15
gaagcgcgag aatcctggga attcgtc                                       27

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
gtaataaagg tgagcgacga attcccagga                                    30

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
gtaataaagg tggatgacga attcccagga                                    30
```

```
<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
gtaataaagg tggaagacga attcccagga                                    30

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
gtaataaagg tgatggacga attcccagga                                    30

<210> SEQ ID NO 20
<211> LENGTH: 30
<212> TYPE: DNA
<213> ORGANISM: Artificial
<220> FEATURE:
<223> OTHER INFORMATION: primer

<400> SEQUENCE: 20
gtaataaagg tgaaagacga attcccagga                                    30

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
gtaataaagg tgcgtgacga attcccagga                                    30

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
gtaataaagg tggtggacga attcccagga                                    30

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
gtaataaagg tgaacgacga attcccagga                                    30

<210> SEQ ID NO 24
<211> LENGTH: 30
<212> TYPE: DNA
<213> ORGANISM: Artificial
<220> FEATURE:
```

```
<223> OTHER INFORMATION: primer

<400> SEQUENCE: 24
ggcgaatttg gctatttctt cgaacctgat                                    30

<210> SEQ ID NO 25
<211> LENGTH: 30
<212> TYPE: DNA
<213> ORGANISM: Artificial
<220> FEATURE:
<223> OTHER INFORMATION: primer

<400> SEQUENCE: 25 tattcacacca aactcatcag gttcgaagaa                                   30

<210> SEQ ID NO 26
<211> LENGTH: 27
<212> TYPE: DNA
<213> ORGANISM: Artificial
<220> FEATURE:
<223> OTHER INFORMATION: primer

<400> SEQUENCE: 26
ggcttcttct atgaacctga tgagttt                                       27

<210> SEQ ID NO 27
<211> LENGTH: 27
<212> TYPE: DNA
<213> ORGANISM: Artificial
<220> FEATURE:
<223> OTHER INFORMATION: primer

<400> SEQUENCE: 27
ctttattaca ccaaactcat caggttc                                       27

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
tcagccggcc ataacctcaa caagatcatg                                    30

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29
gcgcagtcgt attcccatga tcttgttgag                                    30

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30
tcagccggcc atgcgctcaa caagatcatg                                    30
```

```
<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
aaggcttggg tggaagctca tattcagttg                              30

<210> SEQ ID NO 32
<211> LENGTH: 30
<212> TYPE: DNA
<213> ORGANISM: Artificial
<220> FEATURE:
<223> OTHER INFORMATION: primer

<400> SEQUENCE: 32
ggcctcttca ggcgtcaact gaatatgagc                              30

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
aaggcttggg tgcaggctca tattcagttg                              30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
aaggcttggg tgaaagctca tattcagttg                              30

<210> SEQ ID NO 35
<211> LENGTH: 30
<212> TYPE: DNA
<213> ORGANISM: Artificial
<220> FEATURE:
<223> OTHER INFORMATION: primer

<400> SEQUENCE: 35
cacctttatt acaccaaact catcaggctc                              30

<210> SEQ ID NO 36
<211> LENGTH: 30
<212> TYPE: DNA
<213> ORGANISM: Artificial
<220> FEATURE:
<223> OTHER INFORMATION: primer

<400> SEQUENCE: 36
tgtaataaag gtgcacgacg agttcccagg                              30

<210> SEQ ID NO 37
<211> LENGTH: 30
<212> TYPE: DNA
<213> ORGANISM: Artificial
<220> FEATURE:
<223> OTHER INFORMATION: primer
```

```
<400> SEQUENCE: 37
tgtaataaag gtgaccgacg agttcccagg                              30

<210> SEQ ID NO 38
<211> LENGTH: 30
<212> TYPE: DNA
<213> ORGANISM: Artificial
<220> FEATURE:
<223> OTHER INFORMATION: primer

<400> SEQUENCE: 38
gccaaattcg ccattataca caactgggac                              30

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
ttattctttg agcctgatga gtttggtgta                              30

<210> SEQ ID NO 40
<211> LENGTH: 30
<212> TYPE: DNA
<213> ORGANISM: Artificial
<220> FEATURE:
<223> OTHER INFORMATION: primer

<400> SEQUENCE: 40
atgttctttg agcctgatga gtttggtgta                              30

<210> SEQ ID NO 41
<211> LENGTH: 30
<212> TYPE: DNA
<213> ORGANISM: Artificial
<220> FEATURE:
<223> OTHER INFORMATION: primer

<400> SEQUENCE: 41
gaagaagcca aattcgccat tatacacaac                              30

<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42
ttagagcctg atgagtttgg tgtaataaag                              30

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
atggagcctg atgagtttgg tgtaataaag                              30

<210> SEQ ID NO 44
<211> LENGTH: 437
```

<212> TYPE: PRT
<213> ORGANISM: Eupenicillium terrenum

<400> SEQUENCE: 44

```
Met Ala His Ser Arg Ala Ser Thr Lys Val Val Val Gly Gly Gly
1               5                  10                  15
Gly Thr Ile Gly Ser Ser Thr Ala Leu His Leu Ile Arg Ser Gly Tyr
                20                  25                  30
Thr Pro Ser Asn Ile Thr Val Leu Asp Val Tyr Lys Thr Pro Ser Leu
            35                  40                  45
Gln Ser Ala Gly His Asp Leu Asn Lys Ile Met Gly Ile Arg Leu Arg
        50                  55                  60
Asn Gly Pro Asp Leu Gln Leu Ser Leu Glu Ser Leu Asp Met Trp Gln
65                  70                  75                  80
Asn Asp Glu Leu Phe Lys Pro Phe Phe His Gln Val Gly Met Ile Asp
                85                  90                  95
Cys Ser Ser Lys Glu Gly Ile Glu Asn Leu Arg Arg Lys Tyr Gln
            100                 105                 110
Thr Leu Leu Asp Ala Gly Ile Gly Leu Glu Lys Thr Asn Val Trp Leu
        115                 120                 125
Glu Ser Glu Asp Glu Ile Leu Ala Lys Ala Pro Asn Phe Thr Arg Glu
130                 135                 140
Gln Val Lys Gly Trp Lys Gly Leu Phe Cys Thr Asp Gly Gly Trp Leu
145                 150                 155                 160
Ala Ala Ala Lys Ala Ile Asn Ala Ile Gly Ile Phe Leu Gln Asp Lys
                165                 170                 175
Gly Val Lys Phe Gly Phe Gly Asp Ala Gly Thr Phe Gln Gln Pro Leu
            180                 185                 190
Phe Ala Ala Asp Gly Lys Thr Cys Ile Gly Leu Glu Thr Thr Asp Gly
        195                 200                 205
Thr Lys Tyr Phe Ala Asp Lys Val Val Leu Ala Ala Gly Ala Trp Ser
210                 215                 220
Pro Thr Leu Val Asp Leu Glu Asp Gln Cys Val Ser Lys Ala Trp Val
225                 230                 235                 240
Phe Ala His Ile Gln Leu Thr Pro Lys Glu Ala Asp Ala Tyr Lys Asn
                245                 250                 255
Val Pro Val Val Tyr Asp Gly Glu Tyr Gly Phe Phe Phe Glu Pro Asp
            260                 265                 270
Glu Tyr Gly Val Ile Lys Val Cys Asp Glu Phe Pro Gly Phe Ser Arg
        275                 280                 285
Phe Lys Leu His Gln Pro Tyr Gly Ala Ala Ser Pro Lys Met Ile Ser
290                 295                 300
Val Pro Arg Ser His Ala Lys His Pro Thr Asp Thr Tyr Pro Asp Ala
305                 310                 315                 320
Ser Glu Val Thr Ile Arg Lys Ala Ile Ala Arg Phe Leu Pro Glu Phe
                325                 330                 335
Lys Asp Lys Glu Leu Phe Asn Arg Thr Met Cys Trp Cys Thr Asp Thr
            340                 345                 350
Ala Asp Ala Asn Leu Leu Ile Cys Glu His Pro Lys Trp Lys Asn Phe
        355                 360                 365
Ile Leu Ala Thr Gly Asp Ser Gly His Ser Phe Lys Leu Leu Pro Asn
370                 375                 380
Ile Gly Lys Tyr Val Val Glu Leu Leu Glu Gly Ser Leu Ser Gln Glu
385                 390                 395                 400
```

Met Ala Gly Ala Trp Arg Trp Arg Pro Gly Gly Asp Ala Leu Arg Ser
            405                 410                 415

Arg Arg Gly Ala Pro Ala Lys Asp Leu Ala Glu Met Pro Gly Trp Lys
        420                 425                 430

His Asp Ala His Leu
        435

<210> SEQ ID NO 45
<211> LENGTH: 1314
<212> TYPE: DNA
<213> ORGANISM: Eupenicillium terrenum

<400> SEQUENCE: 45

| | | | | | |
|---|---|---|---|---|---|
| atggctcatt | cgcgtgcaag | caccaaagtc | gtcgtggttg | ggggaggtgg | tacgatcggg | 60 |
| tcttcgacgg | ctctgcactt | aatccgctct | ggatataccc | cctcaaatat | caccgtgctt | 120 |
| gacgtataca | agacccttc | attgcaatct | gcaggacatg | atttgaacaa | gatcatgggc | 180 |
| attcgattgc | gcaacgggcc | tgacttgcag | ctttcgctgg | aatcactcga | catgtggcaa | 240 |
| aacgatgagt | tgttcaagcc | attctttcac | caagtgggca | tgattgattg | ttcgtcatcc | 300 |
| aaagagggta | ttgaaaatct | tcgacgaaaa | taccagaccc | tcctcgatgc | gggcattggg | 360 |
| ctggagaaga | cgaacgtttg | gctggaatct | gaagatgaga | tcctcgccaa | agcgccgaat | 420 |
| ttcacgcgtg | aacaagtcaa | ggggtggaaa | ggcttatttt | gcactgatgg | aggctggctt | 480 |
| gctgcagcca | aggctatcaa | tgcgatcgga | attttcctcc | aggacaaagg | tgtcaagttt | 540 |
| ggctttggag | atgctggtac | ctttcagcaa | cctctgttcg | ccgctgatgg | aaaaacttgc | 600 |
| atcggacttg | aaactacaga | cggaaccaag | tactttgctg | acaaggttgt | cttggctgct | 660 |
| ggtgcgtgga | gtcccacctt | ggtggatcta | aagatcagt | gtgtttcaaa | ggcctgggtt | 720 |
| ttcgctcata | ttcaactcac | acccaaagaa | gcggacgcgt | acaagaatgt | gcctgtggtc | 780 |
| tatgatggtg | aatatgggtt | cttttttcgaa | cccgacgagt | atggggtgat | caaagtctgt | 840 |
| gacgagttcc | tggtttctc | tcgcttcaaa | ctgcatcaac | cgtacggggc | tgcatctccc | 900 |
| aagatgatat | ccgtaccgcg | atcacacgcc | aagcatccca | cagataccta | ccctgatgcc | 960 |
| tccgaagtca | ccatacgcaa | agcgatcgca | aggttcctgc | agaatttaa | agacaaggag | 1020 |
| ctcttcaacc | gtaccatgtg | ctggtgtaca | gatacggccg | atgctaactt | attgatttgc | 1080 |
| gaacacccga | agtggaagaa | tttcattctg | gccactggag | atagcggaca | ttccttcaag | 1140 |
| ctgttgccaa | acatcgggaa | atacgtagtt | gagcttttag | agggatctct | atcgcaggaa | 1200 |
| atggctggtg | cctggagatg | gagacccgga | ggtgatgctc | ttagatctag | acgcggtgct | 1260 |
| ccggcaaagg | atcttgctga | gatgccggga | tggaagcatg | atgcacattt | gtga | 1314 |

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46
gactttgatc accccatact cgtcgggctc                                           30

<210> SEQ ID NO 47
<211> LENGTH: 30
<212> TYPE: DNA
<213> ORGANISM: Artificial

```
<220> FEATURE:
<223> OTHER INFORMATION: primer

<400> SEQUENCE: 47
ggtgatcaaa gtccaggacg agttccctgg                                          30

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
ggtgatcaaa gtcagtgacg agttccctgg                                          30

<210> SEQ ID NO 49
<211> LENGTH: 1314
<212> TYPE: DNA
<213> ORGANISM: Phaeosphaeria nodorum

<400> SEQUENCE: 49
atggccccgt cgcgtgctaa tacgtcggtc attgtggttg gtggtggtgg tacgattggc         60
tcatctacgg ctctgcatct ggtccgctca ggctataccc cgtcgaacgt gacggttctg        120
gatgcatacc cgattccgag ctctcagagc gctggcaacg acctgaataa aatcatgggt        180
gtctctctgc gtaatccggt ggatctgcag ctggctctgg aagcgcgcca aatgtggaac        240
gaagacgaac tgttcaagaa gttttttccat aacaccggcc gtctggattg cgcgcacggt       300
gaaaaagata ttgccgacct gaagagcggc tatcaggctc tggtggatgc gggtctggac        360
gccacgaacg aatggctgga tagtgaagac gaaatcctga acgtatgcc gctgctgtcc         420 cgcgatcaaa ttaaaggctg aaggcgatc ttttcaaaag acggtggttg ctggcagca          480 gcaaaggcaa ttaatgcagt tggtgaatat ctgcgtgatc agggcgtccg cttcggtttt        540
tacggcgccg gttctttcaa agcaccgctg ctggctgaag gcgtctgcat cggtgtcgaa        600
accgtggatg gcacgcgcta ttacgcagac aaagtggttc tggctgcagg tgcatggtcg        660
ccgaccctgg ttgaactgca tgaacagtgt gtgagcaaag cgtgggttta cggccacatt        720
caactgacgc cggaagaagc cgcacgttat aagaacagcc cggtcgtgta caatggcgat        780
gtgggctttt tctttgaacc gaacgaacat ggcgttatca aagtctgcga tgaatttccg        840
ggttttaccc gcttcaagat gcaccagccg tttggtgcca aagcaccgaa gcgtattagt        900
gtgccgcgct cccatgccaa acacccgacc gatacgatcc cggatgcaag tgacgtttcc        960
attcgtcgcg ctatcgcgac ctttatgccg cagttcaaga acaaaaagat gttcaaccaa       1020
gcgatgtgct ggtgtaccga tacggccgac gctgcgctgc tgatttgtga acatccggaa       1080
tggaaaaact tgttctggc gaccggcgat tcaggtcatt cgttcaaact gctgccgaat        1140
atcggcaagc acgttgtcga actgctggag ggtacgctgg cagatgacct ggcacacgca       1200
tggcgttggc gtccgggtag tggtgatgca ctgaaaagcc gtcgctctgc tccggcgaaa       1260
gacctggctg atatgccggg ctggaaccat gacaaaccgc gtgctaatct gtaa            1314

<210> SEQ ID NO 50
<211> LENGTH: 30
<212> TYPE: DNA
<213> ORGANISM: Artificial
<220> FEATURE:
<223> OTHER INFORMATION: primer
```

<400> SEQUENCE: 50
gactttgata acgccatgtt cgttcggttc                               30

<210> SEQ ID NO 51
<211> LENGTH: 30
<212> TYPE: DNA
<213> ORGANISM: Artificial
<220> FEATURE:
<223> OTHER INFORMATION: primer

<400> SEQUENCE: 51
cgttatcaaa gtccaggatg aatttccggg                               30

<210> SEQ ID NO 52
<211> LENGTH: 30
<212> TYPE: DNA
<213> ORGANISM: Artificial
<220> FEATURE:
<223> OTHER INFORMATION: primer

<400> SEQUENCE: 52
cgttatcaaa gtcagcgatg aatttccggg                               30

<210> SEQ ID NO 53
<211> LENGTH: 438
<212> TYPE: PRT
<213> ORGANISM: Aspergillus nidulans

<400> SEQUENCE: 53

Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Gly Ile Arg Leu Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Met Ile Asp Val
                85                  90                  95

Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val

```
            225                 230                 235                 240
        Phe Ala His Ile Gln Leu Thr Pro Ala Glu Ala Ala Tyr Lys Asn
                        245                 250                 255

Thr Pro Val Ile Tyr Asp Gly Asp Tyr Gly Phe Phe Glu Pro Asn
                        260                 265                 270

Glu Asn Gly Ile Ile Lys Val Cys Asp Glu Phe Pro Gly Phe Thr His
                        275                 280                 285

Phe Lys Met His Gln Pro Tyr Gly Ser Pro Ala Pro Lys Pro Ile Ser
                290                 295                 300

Val Pro Arg Ser His Ala Lys His Pro Thr Asp Thr Tyr Pro His Ala
        305                 310                 315                 320

Ser Glu Val Thr Ile Lys Lys Ala Ile Asn Arg Phe Leu Pro Arg Phe
                        325                 330                 335

Asn Asp Lys Glu Leu Phe Asn Arg Ala Met Cys Trp Cys Thr Asp Thr
                        340                 345                 350

Ala Asp Ala Asn Leu Leu Val Cys Glu His Pro Arg Trp Lys Gly Phe
                        355                 360                 365

Tyr Leu Ala Thr Gly Asp Ser Gly His Ser Phe Lys Leu Leu Pro Asn
                370                 375                 380

Ile Gly Lys His Val Val Glu Leu Leu Glu Glu Arg Leu Glu Ser Val
        385                 390                 395                 400

Phe Lys Asp Ala Trp Arg Trp Arg Pro Gly Ser Gly Asp Ala Leu Lys
                        405                 410                 415

Ser Arg Arg Ala Ala Pro Ala Lys Asp Leu Ala Asp Met Pro Gly Trp
                        420                 425                 430

Arg Asn Glu Ala Lys Met
                        435

<210> SEQ ID NO 54
<211> LENGTH: 1317
<212> TYPE: DNA
<213> ORGANISM: Aspergillus nidulans

<400> SEQUENCE: 54
atgacgcccc gagccaacac caaaatcatt gtcgtcggcg gcggcggcac aatgggctcg         60
tcgacagccc tacacctcct gcgcgccggc tacgccgt ccaacattac agtgctcgac         120
acgtgcccta tccctccgc acagtctgca ggctacgacc tgaacaaaat catggggatc         180
cgtctgcgca caagcctga tttacagctc tctcttgagg cgctggacat gtggaaaaat         240
gatcctctct tcaagccgtt tttccacaat gttggaatga tcgacgtctc ttcaacagag         300
gaaggcatcg agggtcttcg gaagaaatac cagtctcttc tcgacgcagg cattgggctc         360
gagaagacga atttcatgct ggaaagtgaa gacgagatcc tggctaaagc gccgcatttc         420
acgcaggagc agattaaagg ctggaaaggc ctgttctgtg gcgacggcgg ctggctcgct         480
gcagccaaag ccatcaatgc cattgggcag ttcctcaagg aacagggcgt caagtttgga         540
ttcggcggcg ccggcacgtt caaaaagcca ctcttcgccg atgcccacga agacgtgc         600 atcggcgtcg agactgtaga cggcacaaag tactacgccg acaaggtcgt tctagcagct         660
ggtgcctgga gttcgacgtt ggtcgatctg gaggagcagt gcgtttcaaa ggcctgggtc         720 tttgccccaca tccaactgac gcccgctgaa gcagccgcgt ataagaacac tcctgtttata         780 tacgacggtg actatgggtt tttctttgag ccgaatgaaa acggcatcat aaaagtctgt         840
gacgaattcc ctggcttcac gcatttcaaa atgcaccagc cgtacggctc gccggcgccc         900
```

| | |
|---|---|
| aaacccatct ctgtgcctcg ttcccatgcg aagcacccca cagatacata cccgcacgcg | 960 |
| tcggaggtca cgatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagtgggca ttcgttcaag | 1140 |
| ttgctgccga atattggaaa gcatgttgtc gagttattgg aggagaggct ggaaagtgtg | 1200 |
| tttaaggatg cttggaggtg gaggcctggc agtggggatg cattaaaaag tagacgggct | 1260 |
| gcgcctgcga aggacctggc ggatatgccg gggtggagga atgaggcaaa gatgtag | 1317 |

<210> SEQ ID NO 55
<211> LENGTH: 30
<212> TYPE: DNA
<213> ORGANISM: Artificial
<220> FEATURE:
<223> OTHER INFORMATION: primer

<400> SEQUENCE: 55

| | |
|---|---|
| gacttttatg atgccgtttt cattcggctc | 30 |

<210> SEQ ID NO 56
<211> LENGTH: 30
<212> TYPE: DNA
<213> ORGANISM: Artificial
<220> FEATURE:
<223> OTHER INFORMATION: primer

<400> SEQUENCE: 56

| | |
|---|---|
| catcataaaa gtccaggacg aattccctgg | 30 |

<210> SEQ ID NO 57
<211> LENGTH: 30
<212> TYPE: DNA
<213> ORGANISM: Artificial
<220> FEATURE:
<223> OTHER INFORMATION: primer

<400> SEQUENCE: 57

| | |
|---|---|
| catcataaaa gtcagtgacg aattccctgg | 30 |

<210> SEQ ID NO 58
<211> LENGTH: 1323
<212> TYPE: DNA
<213> ORGANISM: Curvularia clavata

<400> SEQUENCE: 58

| | |
|---|---|
| atggccccga gtcgcgctaa cacgagcgtc attgtggtgg gtggtggtgg cacgattggt | 60 |
| tcctcaacgg cactgcatct ggtccgtagc ggctataccc cgtctaacat taccgtgctg | 120 |
| gacacgtacc cgatcccgag cgcccagtct gcaggcaacg atctgaataa aattatgggt | 180 |
| atccgtctgc gcaacaaagt tgatctgcag ctgtcactgg aagcccgtca aatgtggcgc | 240 |
| gaagatgacc tgtttaaaga atacttccat aacaccggcc gtctggattg cgcacacggt | 300 |
| gaagaaggtc tggccgacct gcgccaggct taccaagcgc tgctggatgc caacgcaggt | 360 |
| ctggaagaaa ccacggaatg gctggattca gaagacgaaa ttctgaagaa aatgccgctg | 420 |
| ctggatcgtg aacagatcaa aggttggaaa gccgtgtatt cgcaagatgg cggttggctg | 480 |
| gcggccgcaa aagccattaa tgcaatcggc gaatacctgc gcgcgcaggg cgttaaattc | 540 |
| ggttttggcg gtgctggttc ctttaaacag ccgctgctgg cagaaggcgt ctgcattggt | 600 |
| gtcgaaaccg tggatggcac gcgttattac gcggacaaag tggttctggc tgcaggtgca | 660 |

```
tggagtccgg tgctggttga tctggaagac cagtgtgtgt ccaaagcgtg ggtttatgcg      720
catatccaac tgaccccgga agaagccgca gaatataaaa acgtcccggt cgtgtacaat      780
ggcgatgtgg gcttttctt tgaaccggac gaacatggcg ttattaaagt ctgcgatgaa       840
tttccgggtt ttacccgctt caaacagcac caaccgtatg gcgctaaagc gccgaaacgt      900
atctcagtgc gcgttcggc tgcaaaacac ccgaccgata cgtacccgga cgcgagtgaa      960
aaatccattc gtaaagccat cgcaaccttt ctgccgaaat tcacggaaaa agaactgttt     1020
aatcgccatc tgtgctggtg taccgatacg gccgacgccg cactgctgat gtgtgaacac     1080
ccggaatgga aaactttgt tctggcgacc ggcgatagcg gtcatacgtt caaactgctg      1140
ccgaatattg gcaaacacgt tgtcgaactg ctggaaggta ccctggcaga agacctggct     1200
catgcgtggc gttggcgtcc gggtacgggt gatgcactga atctcgtcg cgctgcgccg      1260 gcgaaagacc tggcggatat gccgggctgg aaacacgacg atgtggtgaa aagcaaactg     1320
taa                                                                    1323
```

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59
gactttaata acgccatgtt cgtccggttc      30

<210> SEQ ID NO 60
<211> LENGTH: 29
<212> TYPE: DNA
<213> ORGANISM: Artificial
<220> FEATURE:
<223> OTHER INFORMATION: primer

<400> SEQUENCE: 60
cgttattaaa gtccaggatg aatttccgg      29

<210> SEQ ID NO 61
<211> LENGTH: 29
<212> TYPE: DNA
<213> ORGANISM: Artificial
<220> FEATURE:
<223> OTHER INFORMATION: primer

<400> SEQUENCE: 61
cgttattaaa gtcagcgatg aatttccgg      29

<210> SEQ ID NO 62
<211> LENGTH: 30
<212> TYPE: DNA
<213> ORGANISM: Artificial
<220> FEATURE:
<223> OTHER INFORMATION: primer

<400> SEQUENCE: 62
gcccacatcg ccattgtaca cgaccgggac      30

<210> SEQ ID NO 63
<211> LENGTH: 30
<212> TYPE: DNA
<213> ORGANISM: Artificial
<220> FEATURE:

<223> OTHER INFORMATION: primer

<400> SEQUENCE: 63
ttattctttg aaccggacga acatggcgtt    30

<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64
atgttctttg aaccggacga acatggcgtt    30

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
gaaaaagccc acatcgccat tgtacacgac    30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
ttagaaccgg acgaacatgg cgttattaaa    30

<210> SEQ ID NO 67
<211> LENGTH: 438
<212> TYPE: PRT
<213> ORGANISM: Emericella nidulans

<400> SEQUENCE: 67

Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

```
Ala Ala Lys Ala Ile Asn Ala Ile Gly Gln Phe Leu Lys Glu Gln Gly
            165                 170                 175

Val Lys Phe Gly Phe Gly Glu Ala Gly Thr Phe Lys Lys Pro Leu Phe
        180                 185                 190

Ala Asp Ala Asp Glu Lys Thr Cys Ile Gly Val Glu Thr Val Asp Gly
    195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
        260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 68
<211> LENGTH: 1317
<212> TYPE: DNA
<213> ORGANISM: Emericella nidulans

<400> SEQUENCE: 68
atggctccgc gtgcgaatac gaaaatcatt gttgtcggtg gtggtggtac gatgggttca      60
agtacggctc tgcatctgct gcgtgcgggc tataccccga gcaacattac cgtgctggat     120
acgtatccga tcccgtcagc gcagtcggcc ggttacgacc tgaacaaaat ttttggtatc     180
agcggtgcaa ataaacatga tctgcaactg tctctggaag cgtttgatat gtggaaaaac     240
gacccgctgt ttaaaccgtt tttccacaat gtgggccaga tggatgttag ctctaccgaa     300
gaaggtatta aacgcctgcg tcgccgttac caaagtctgc tgcgtgccgg catcggtctg     360
gaaaaaacca acttcctgct ggaatccgaa gatgaaattc tggcgaaagc cccgcatttc     420
acgcgcgaac agatcaaagg ctggaaaggt ctgttttgcg gtgatggcgg ttggctggcc     480
```

```
gcagcaaaag caattaatgc tatcggccag tttctgaaag aacaaggtgt gaaatttggc      540
ttcggtgaag cgggtacctt caaaaaaccg ctgtttgcag atgctgacga aaaaacgtgc      600
attggcgttg aaaccgtcga tggtacgaaa tattacgcag acaaagtggt tctggctgcg      660
ggcgcttgga gttccaccct ggttgatctg gaagaacagt gtgtcagcaa agcgtgggtg      720
tttgcccaca tccaactgac cccggccgaa gccgcagctt ataaaaacac gccggtgatt      780
tatgatggcg actacggctt tttcatcgaa ccggatgaaa atggcattat caaagtttgc      840
gacgaatttc cgggttttcac ccattttaaa atgcaccagc cgtatggctc accggttccg      900
aaactgatta gtgtcccgcg ttcccatgca aacacccga ccgatacgta cccgcatgca       960
tcggaagtca cgattaagaa agcgatcaac cgcttcctgc cgcgttttaa cgacaaagaa     1020
ctgttcaatc gcgcgatgtg ctggtgtacc gatacggccg acagcaatct gctggtttgt     1080
gaacacccgc gttggaaagg tttctatctg gcgaccggcg atagcggtca ttcttttaaa     1140
ctgctgccga atattggcaa acacgtcgtg gaactgctgg aaggtcgcct ggaatctgtg     1200
tttaaagatg cgtggcgctg gcgtccgggc tcaggtgatg cactgaaatc gcgtcgcgca     1260
gcaccggcga aagacctggc ggatatgccg ggttggcgta atgaagcgaa aatgtaa       1317
```

```
<210> SEQ ID NO 69
<211> LENGTH: 35
<212> TYPE: DNA
<213> ORGANISM: Artificial
<220> FEATURE:
<223> OTHER INFORMATION: primer

<400> SEQUENCE: 69
gaaggagata tacatatggc tccgcgtgcg aatac                                 35

<210> SEQ ID NO 70
<211> LENGTH: 35
<212> TYPE: DNA
<213> ORGANISM: Artificial
<220> FEATURE:
<223> OTHER INFORMATION: primer

<400> SEQUENCE: 70
ctcgaattcg gatccttaca ttttcgcttc attac                                 35

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
ggatccgaat tcgagctccg tcgacaagct                                       30

<210> SEQ ID NO 72
<211> LENGTH: 30
<212> TYPE: DNA
<213> ORGANISM: Artificial
<220> FEATURE:
<223> OTHER INFORMATION: primer

<400> SEQUENCE: 72
atgtatatct ccttcttaaa gttaaacaaa                                       30

<210> SEQ ID NO 73
<211> LENGTH: 30
```

```
<212> TYPE: DNA
<213> ORGANISM: Artificial
<220> FEATURE:
<223> OTHER INFORMATION: primer

<400> SEQUENCE: 73
aactttgata atgccatttt catccggttc                                    30

<210> SEQ ID NO 74
<211> LENGTH: 30
<212> TYPE: DNA
<213> ORGANISM: Artificial
<220> FEATURE:
<223> OTHER INFORMATION: primer

<400> SEQUENCE: 74
caggacgaat ttccgggttt cacccatttt                                    30

<210> SEQ ID NO 75
<211> LENGTH: 30
<212> TYPE: DNA
<213> ORGANISM: Artificial
<220> FEATURE:
<223> OTHER INFORMATION: primer

<400> SEQUENCE: 75
agcgacgaat ttccgggttt cacccatttt                                    30

<210> SEQ ID NO 76
<211> LENGTH: 30
<212> TYPE: DNA
<213> ORGANISM: Artificial
<220> FEATURE:
<223> OTHER INFORMATION: primer

<400> SEQUENCE: 76
gccgtagtcg ccatcataaa tcaccggcgt                                    30

<210> SEQ ID NO 77
<211> LENGTH: 30
<212> TYPE: DNA
<213> ORGANISM: Artificial
<220> FEATURE:
<223> OTHER INFORMATION: primer

<400> SEQUENCE: 77
ttattcatcg aaccggatga aaatggcatt                                    30

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
atgttcatcg aaccggatga aaatggcatt                                    30

<210> SEQ ID NO 79
<211> LENGTH: 30
<212> TYPE: DNA
<213> ORGANISM: Artificial
<220> FEATURE:
<223> OTHER INFORMATION: primer

<400> SEQUENCE: 79
```

-continued

```
gaaaaagccg tagtcgccat cataaatcac                                        30

<210> SEQ ID NO 80
<211> LENGTH: 30
<212> TYPE: DNA
<213> ORGANISM: Artificial
<220> FEATURE:
<223> OTHER INFORMATION: primer

<400> SEQUENCE: 80
ctcgaaccgg atgaaaatgg cattatcaaa                                        30

<210> SEQ ID NO 81
<211> LENGTH: 30
<212> TYPE: DNA
<213> ORGANISM: Artificial
<220> FEATURE:
<223> OTHER INFORMATION: primer

<400> SEQUENCE: 81
atggaaccgg atgaaaatgg cattatcaaa                                        30

<210> SEQ ID NO 82
<211> LENGTH: 30
<212> TYPE: DNA
<213> ORGANISM: Artificial
<220> FEATURE:
<223> OTHER INFORMATION: primer

<400> SEQUENCE: 82
atggaaccgg acgaacatgg cgttattaaa                                        30
```